United States Patent [19]

Shiosaki et al.

[11] Patent Number: 5,340,802
[45] Date of Patent: Aug. 23, 1994

[54] PEPTIDE ANALOG TYPE-B CCK RECEPTOR LIGANDS

[75] Inventors: Kazumi Shiosaki, Libertyville, Ill.; Alex M. Nadzan, San Diego, Calif.; David S. Garvey, Lake Forest, Ill.; Youe-Kong Shue, Vernon Hills, Ill.; Mark S. Brodie, Glenview, Ill.; Mark W. Holladay, Libertyville, Ill.; John Y.-L. Chung, Edison, N.J.; Michael D. Tufano, Chicago, Ill.; Paul D. May, Richland, Mich.

[73] Assignee: Abbott Laboratories, Abbott Park, Ill.

[21] Appl. No.: 11,055

[22] Filed: Jan. 29, 1993

Related U.S. Application Data

[63] Continuation-in-part of Ser. No. 791,805, Nov. 13, 1991, abandoned, which is a continuation-in-part of Ser. No. 531,771, Jun. 6, 1990, abandoned, which is a continuation-in-part of Ser. No. 375,107, Jun. 30, 1989, abandoned.

[51] Int. Cl.$^5$ ............ A61K 37/02; C07K 5/06; C07K 5/08; C07K 5/10
[52] U.S. Cl. ........................ 514/18; 514/19; 530/330; 530/331
[58] Field of Search ............ 514/18, 19; 530/330, 530/331

[56] References Cited

U.S. PATENT DOCUMENTS

| | | | |
|---|---|---|---|
| 4,294,825 | 10/1981 | Knoll et al. | 514/21 |
| 4,481,138 | 11/1984 | Tachibana et al. | 530/326 |
| 4,490,364 | 10/1984 | Rivier et al. | 514/16 |
| 4,618,598 | 10/1986 | Conn | 514/12 |

OTHER PUBLICATIONS

McLaughlin et al. "Effect of CCK Antibodies on Food Intake and Weight in Zuckerrats", Physiol. Behav, 34:227–282 (1985).
D. Horwell et al., J. Med. Chem. 30:725–732 (1987).

Primary Examiner—Lester L. Lee
Attorney, Agent, or Firm—Richard A. Elder; Steven R. Crowley; Steven F. Weinstock

[57] ABSTRACT

Peptide analog type-B CCK receptor ligands or pharmaceutically-acceptable salts thereof, which are useful for treating central nervous system disorders, substance abuse, gastrointestinal disorders, endocrine disorders, eating-related disorders and for the treatment of shock, respiratory and cardiocirculatory insufficiencies.

11 Claims, No Drawings

PEPTIDE ANALOG TYPE-B CCK RECEPTOR LIGANDS

This is a continuation-in-part of copending U.S. patent application Ser. No. 791,805, filed Nov. 13, 1991 and now abandoned, which is a continuation-in-part of U.S. patent application Ser. No. 531,771, filed Jun. 6, 1990, now abandoned, which is a continuation-in-part of U.S. patent application Ser. No. 375,107, filed Jun. 30, 1989, now abandoned.

TECHNICAL FIELD

The present invention relates to peptide compounds and compositions thereof which have biological activity as cholecystokinin receptor ligands, to processes for preparing such compounds, to synthetic intermediates employed in these processes and to a method of treating central nervous system, gastrointestinal, endocrine and eating-related disorders, substance abuse, respiratory and cardiocirculatory insufficiencies, and shock with such compounds.

BACKGROUND OF THE INVENTION

Cholecystokinin (CCK) and related molecules constitute a family of polypeptide hormones that are widely distributed in various parts of the body including the gastrointestinal tract and endocrine glands as well as peripheral and central nervous systems. A 33-amino acid fragment of CCK (CCK-33) was first isolated from hog intestines (Mutt and Jorpes, *Biochem. J.*, 1971, 125: 628) and has subsequently been identified as a neurotransmitter (Rehfeld, *J. Neurochem.*, 1985, 448: 1–8). CCK-33 and two smaller fragments, CCK-8 and CCK-4, also have been identified in the brain (Dockray, *Nature*, 1979, 264: 402), with CCK-8 being the predominant form there.

In the periphery, CCK plays a variety of regulatory roles, including stimulation of gallbladder contraction, pancreatic enzyme secretion and insulin secretion, and inhibition of gastric emptying. In addition, the high concentrations of CCK and CCK receptors found in the brain support the idea that a major brain function exists for this peptide. CCK has been suggested to have central actions in appetite control, schizophrenia, memory and cognition. Also, modulators of CCK actions may have potential as therapeutic agents for drug abuse.

Two sub-types of CCK receptors have been identified. Type-A receptors are found predominantly in the periphery and have high affinity for CCK-8 and low affinity for desulfated CCK-8 and CCK-4. Type-B receptors are found predominantly in the brain and have high affinity for CCK-8, desulfated CCK-8 and CCK-4. CCK-8 and desulfated CCK-8 were shown to be equipotent in enhancing learning and memory in mice and monkeys (Pietrusiak et al., *Soc. Neurosci. Abstr.*, 1988, 13: 1030), which suggests that these actions are mediated by Type-B CCK receptors. Moreover, Hughes et al. (*Proc. Natl. Acad. Sci., U.S.A.*, 1990, 87: 6728–6732) reported the potent and selective activity of two non-peptide CCK-B antagonists, PD134308 and PD135158, as anxiolytic agents. This finding suggests that the CCK-B receptor plays an important role in anxiety states.

Tetragastrin, the C-terminal tetrapeptide of the hormone gastrin, is fully active in stimulation of gastric acid release when compared to the native hormone and is identical to CCK-4, the C-terminal tetrapeptide of cholecystokinin. In addition, gastrin receptors and CCK-type-B receptors share many similarities with respect to ligand binding profiles. They have not yet been clearly demonstrated to be distinct, although their environments are distinctly different, i.e., gastric mucosa vs. brain cortex.

Considerable literature exists on structure-activity relationships of tetragastrin and related analogs with respect to gastric acid release. Morley et al. have synthesized a large number of tetragastrin analogs that explore C-terminal, N-terminal, and single amino acid modifications (*Nature*, 1965, 207: 1356; *Proc Roy. Soc B.* 1968, 170:97–111; *Fed Proc.* 1968, 27:1314; *J. Chem. Soc. C.* 1969, 5:809–13; U.S. Pat. No. 3,896,103 (1975)).

Cipens et al. (*Khim Prir. Soedin.* 6:117–119 (1970)) report Trp replacements in tetragastrin comprising 1-naphthylpropionic acid, 2-naphthylpropionic acid, naphthylacrylic acid and $N^{in}$-Me-Trp, and Japanese Patent 71009454 (1971) reports Ala-Gly-Asp-Phe-$NH_2$ and amino-protected derivatives of tetragastrin that inhibit gastric acid secretion. Japanese Patent 71016743 (1971) reports tetragastrin analogs, in which Gly is substituted for Asp, that inhibit gastric acid secretion and possess antitumor activity, and Japanese Patent 71017234 (1971) reports tetragastrin analogs in which beta-methylAsp is substituted for Asp, which stimulate gastric acid secretion.

Japanese Patent Application JA7138992 (1971) discloses the preparation of protected forms of Trp-Met-Asp-Phe-$NH_2$, and German Patent Application DE2245459 (1973), discloses the preparation of N-protected forms of that peptide. Higaki et al. (*Pharmacometrics* 1974, 8:147–155) reported on structure-activity relationships of various N-acylated and amino acid-substituted analogs of tetragastrin with respect to gastric acid secretion in the rat, with tri-, tetra- and pentapeptides being tested, of which only peptides with Leu and Val substituted for Met and those with hydrazide substituted for C-terminal amide had significant activity.

Kisfaludy et al. (U.S. Pat. No. 4,183,909 (1980)) report tetragastrin analogs wherein Phe is replaced by phenylglycine and Met is replaced by Leu, Ile, Nva or 2-aminodecanoic acid, and Zarandi et al. (*Peptides* 1982, Walter de Gruyter & Co., Berlin & N.Y., 1983, pp 577–581) report biological activity in tetragastrin analogs wherein Trp is substituted by FMOC (9-fluorenylmethyloxycarbonyl).

Romanovski et al. (Russian patent SU624911 (1978)) report N-acylated pentapeptide analogs with succinyl-sarcosine in the N-terminal position that stimulate gastric acid secretion., and U.S. Pat. No. 4,172,130 (1979) reports analogs with novel N-protecting groups in which Met is substituted by Leu, Ile, Nle, Nva or 2-aminodecanoyl, which also have gastric acid stimulating activity. Charon et al. (U.S. Pat. No. 4,530,837 (1975)) report new pentapeptide analogs with Asp substituted by other dicarboxylic acids or substituted with various amides at the omega carboxyl group for use as gastric secretion inhibitors.

European Patent Application EP0239716, to Bertolini et al. (1987), discloses fragments of gastrin containing the peptide Trp-Met-Asp-Phe-$NH_2$ for the therapy of shock and of respiratory and cardiocirculatory insufficiencies. The interaction of several CCK-4-related peptides with CCK-B receptors was reported by Horwell (*J. Med. Chem.*, 1987, 30: 729), and a pentapeptide analog of CCK-5 with an N-methylnorleucine residue in place of Met was recently reported to have high affinity and selectivity for CCK-B receptors (Hruby et al., *Intl. J. Peptide Protein Res.*, 1990, 35:566-573).

Larger peptides related to CCK are known to interact non-selectively with CCK-A and CCK-B receptors. U.S. Pat. No. 4,490,364 (Rivier et al., 1984), discloses heptapeptide, octapeptide and nonapeptide analogs of CCK-8 as agents for stimulating gallbladder contractions, arresting the secretion of gastric acid and treating convulsions. Recently, larger peptides selective for the CCK-B receptor have been reported (Charpentier et al., *Peptides* 1988 (1989) 9:835; Charpentier et al., *Proc. Natl. Acad. Sci. USA*, 1988, 85:1968; Rodriguez et al., *Int. J. Peptide Protein Res.* 1990, 35:566; Hruby et al., *Int. J. Peptide Protein Res.* 1990, 35:441).

A review that discusses CCK agonists and antagonists has recently appeared (Nadzan and Kerwin, *Annual Reports in Medicinal Chemistry* 1991, 26:191-200, Academic Press, N.Y.).

SUMMARY OF THE INVENTION

The present invention is directed to Type-B-selective cholecystokinin ligands of the formula:

W—Y—Z    (I)

or pharmaceutically-acceptable salts thereof, wherein W is selected from

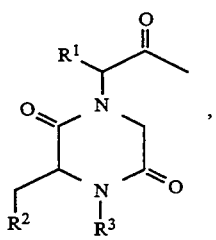    (1)

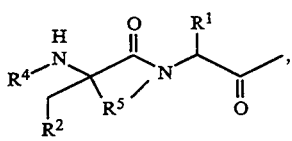    (2)

, and (3) A-B, wherein
A is selected from

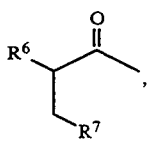    (a)

$R^2$—$R^8$—D—,    (b)

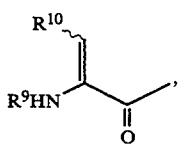    (c)

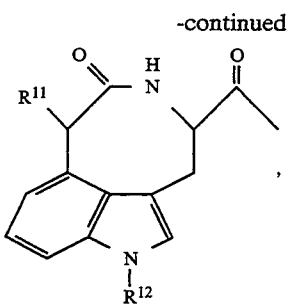    (d)

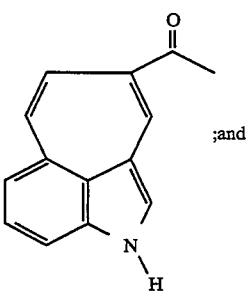    (e)

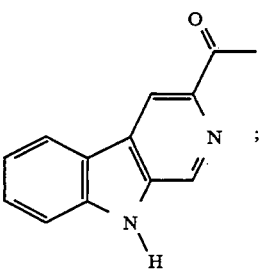    (f)

and
B is selected from

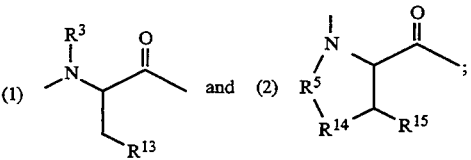

(1)    and    (2)

Y is

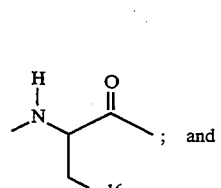    ; and

Z is selected from

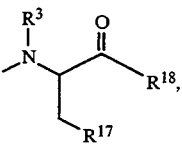    (1)

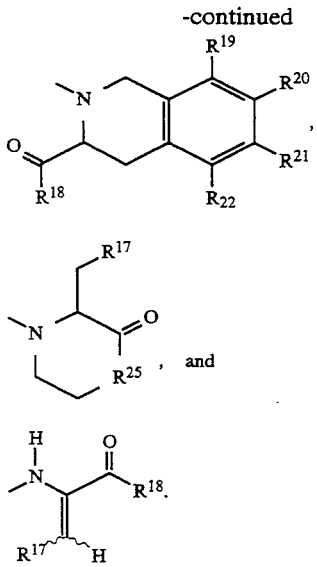

The present invention is also directed to pharmaceutical compositions comprising a therapeutically-effective amount of a compound of formula (I) and a pharmaceutically-acceptable carrier or diluent, as well as to a method of treating CCK-related central nervous system, gastrointestinal, endocrine and eating-related disorders, respiratory and cardiocirculatory insufficiencies, substance abuse and shock with a compound of formula (I).

DETAILED DESCRIPTION OF THE INVENTION

This invention relates to novel peptide analog type-B CCK receptor ligands, which have selective affinity for type-B CCK receptors and, therefore, may be used in the treatment of CCK-related central nervous system, gastrointestinal, endocrine and eating-related disorders, substance abuse, respiratory and cardiocirculatory insufficiencies and shock.

In particular, the present invention relates to Type-B-selective cholecystokinin ligands of the formula:

$$W-Y-Z \qquad (I)$$

or a pharmaceutically-acceptable salt thereof, wherein W is selected from

wherein
R$^1$ is selected from
(i) C$_1$-C$_6$-alkyl, as defined below,
(ii) mono-substituted C$_1$-C$_4$-alkylene, as defined below, wherein the substituent is C$_1$-C$_6$-alkoxy or thio-C$_1$-C$_6$-alkoxy, as defined below, or sulfhydryl, and
(iii) hydroxy-C$_1$-C$_6$-alkyl, as defined below;

R$^2$ is naphthyl, substituted naphthyl, as defined below, benzohet, as defined below, or mono- or di-substituted benzohet, as defined below; and
R$^3$ is hydrogen or C$_1$-C$_6$-alkyl;

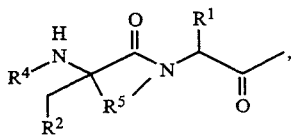

wherein
R$^1$ and R$^2$ are as defined above;
R$^4$ is hydrogen or an N-protecting group, as defined below; and
R$^5$ is C$_2$-C$_4$-alkylene; and $$A-B, \qquad (3)$$

wherein
A is selected from the group consisting of

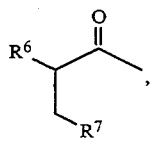

wherein
R$^6$ is selected from the group consisting of
(i) hydrogen,
(ii) halogen,
(iii) hydroxy,
(iv) C$_1$-C$_6$-alkoxy,
(v) thio-C$_1$-C$_6$-alkoxy,
(vi) amino,
(vii) (N-protected)amino, as defined below,
(viii) C$_1$-C$_6$-alkylamino, as defined below,
(ix) (N-protected)-C$_1$-C$_6$-alkylamino, wherein N-protected is as defined below,
(x) di-C$_1$-C$_6$-alkylamino,
(xi) di-C$_1$-C$_6$-alkylamino-C$_1$-C$_6$-alkyl, as defined below,
(xii) monosubstituted C$_1$-C$_8$-alkyl or monosubstituted C$_2$-C$_{12}$-alkenyl, wherein the substituent is selected from (N-protected)amino, C$_1$-C$_6$-alkylamino, and di-C$_1$-C$_6$-alkylamino,
(xiii) R$^{23}$—R$^8$—C(O)—N(R$^3$)—, wherein
R$^3$ is as defined above;
R$^{23}$ is selected from phenyl, substituted phenyl, as defined below, amino, (N-protected)amino, C$_1$-C$_6$-alkylamino, and di-(C$_1$-C$_6$-alkyl)amino; and
R$^8$ is C$_1$-C$_6$-alkylene or C$_2$-C$_6$-alkenylene;
R$^7$ is selected from the group consisting of
(i) naphthyl,
(ii) substituted naphthyl,
(iii) phenyl,
(iv) substituted phenyl,
(v) benzohet,
(vi) mono- or disubstituted benzohet,
(vii) heterotricycle, as defined below, and
(viii) carbotricycle, as defined below;

$$R^2-R^8-D-, \qquad (b)$$

wherein $R^2$ is as defined above; and
$R^8$ is absent or is as defined above; and
D is absent or —C(O)—;

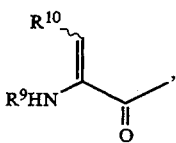

wherein
$R^9$ is selected from the group consisting of
(i) naphthoyl,
(ii) substituted naphthoyl, as defined below,
(iii) —C(O)-benzohet,
(iv) mono- or disubstituted benzohet; and
$R^{10}$ is phenyl or substituted phenyl;

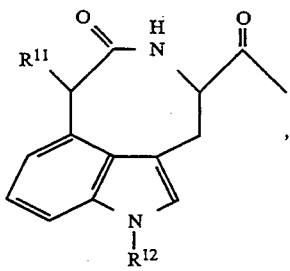

wherein
$R^{11}$ is selected from the group consisting of
(i) hydrogen,
(ii) hydroxy,
(iii) halogen,
(iv) $C_1-C_6$-alkyl,
(v) amino,
(vi) $C_1-C_6$-alkylamino,
(vii) di-$C_1-C_6$-alkylamino,
(viii) mono-substituted $C_1-C_4$-alkylene, wherein the substituent is $C_1-C_6$-alkoxy or thio-$C_1-C_6$-alkoxy; and
$R^{12}$ is hydrogen, $C_1-C_6$-alkyl or $C_1-C_6$-alkanoyl, as defined below;

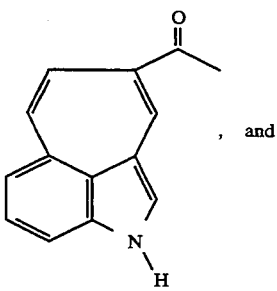

, and

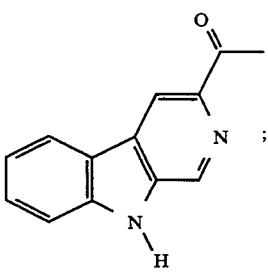

;

B is selected from

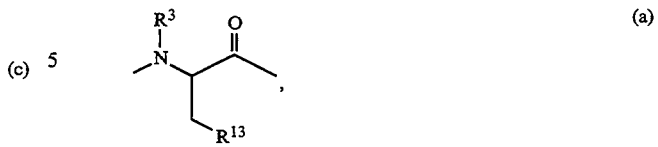

wherein
$R^3$ is as defined above; and
$R^{13}$ is selected from the group consisting of
(i) $C_1-C_6$-alkyl,
(ii) mono-substituted $C_1-C_4$-alkylene, wherein the substituent is $C_1-C_6$-alkoxy or thio-$C_1-C_6$-alkoxy; and

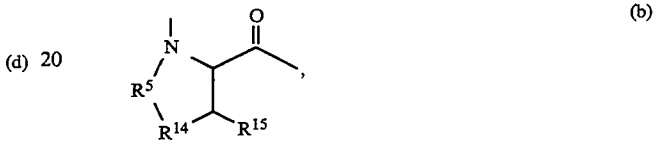

wherein
$R^5$ is as defined above;
$R^{14}$ is absent or is oxygen or sulfur; and
$R^{15}$ is selected from the group consisting of
(i) hydrogen,
(ii) $C_1-C_6$-alkyl,
(iii) $C_1-C_6$-alkoxy,
(iv) thio-$C_1-C_6$-alkoxy, and
(v) mono-substituted $C_1-C_4$-alkylene, wherein the substituent is $C_1-C_6$-alkoxy or thio-$C_1-C_6$-alkoxy; and Y is

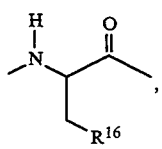

wherein
$R^{16}$ is carboxy or tetrazolyl; and
Z is selected from the group consisting of

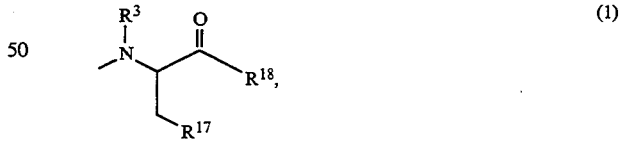

wherein
$R^3$ is as defined above;
$R^{17}$ is selected from the group consisting of
(i) $C_1-C_6$-alkyl,
(ii) cyclo-$C_3-C_8$-alkyl,
(iii) Het, as defined below,
(iv) mono- or disubstituted Het, as defined below,
(v) naphthyl,
(vi) substituted naphthyl,
(vii) phenyl,
(viii) substituted phenyl,
(ix) benzohet, and
(x) mono- or disubstituted benzohet; and
$R^{18}$ is selected from (i) —NHR²⁴, wherein R²⁴ is hydrogen, hydroxy, C₁–C₆-alkyl, or C₁–C₆-alkoxy; and
(ii) —NHNHR³, wherein R³ is as defined above;

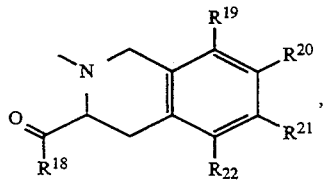
(2)

wherein
R¹⁸ is as defined above;
R¹⁹, R²⁰, R²¹ and R²² are independently selected from the group consisting of
(i) hydrogen,
(ii) C₁–C₆-alkyl,
(iii) halogen,
(iv) halo-C₁–C₆-alkyl,
(v) C₁–C₆-alkoxy,
(vi) thio-C₁–C₆-alkoxy,
(vii) hydroxy,
(viii) C₁–C₆-alkoxycarbonyl, as defined below,
(ix) carboxy,
(x) amino,
(xi) C₁–C₆-alkylamino,
(xii) di-C₁–C₆-alkylamino,
(xiii) nitro, and
(xiv) —OSO₃H; or
R²⁰ and R²¹ and R²² taken together with the carbon atoms to which they are attached form a benzene ring, and R¹⁹ and R²² or R¹⁹ and R²⁰ are independently selected from alternatives (i)-(xiv), as defined immediately above;

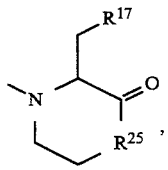
(3)

wherein
R¹⁷ is as defined above; and
R²⁵ is selected from
(i) —NR²⁴, wherein R²⁴ is hydrogen, hydroxy, C₁–C₆-alkyl, or C₁–C₆-alkoxy; and
(ii) —NNHR³, wherein R³ is as defined above;

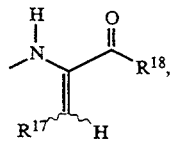
(4)

wherein R¹⁷ and R¹⁸ are as defined above;
with the proviso that when W is A—B and A is selected from either option (a) for A above where R⁶ is hydrogen, amino, (N-protected)amino or R²³—R⁸—C(O)—NR³, or option (b) for A above, then B must be selected from option (b) for B above or Z must be selected from options (2), (3) or (4) for Z above.

In one embodiment of the invention are compounds represented by formula (Ia):

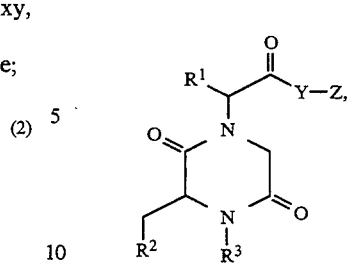
(Ia)

wherein R¹, R², R³, Y and Z are as defined above.

In another embodiment of the invention are compounds represented by formula (Ib):

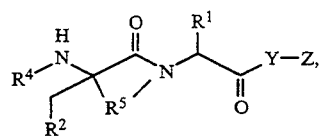
(Ib)

wherein R¹, R², R⁴, R⁵, Y and Z are as defined above.

In a further embodiment of the invention are compounds represented by formula (Ic):

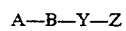
A—B—Y—Z (Ic), wherein A, B, Y and Z are as defined above. In a preferred embodiment of (Ic), A is selected from options (a) and (d) for A above and B is selected from options (b) for B above, or A is selected from option (d) for A above and B is selected from options (a) or (b) for B above. In particularly preferred embodiments of (Ic) A is selected from option (a) above with R⁶ being (N-protected)amino or A is selected from option (d) above with R¹¹ being hydrogen and B is selected from option (b) above with R⁵ being C₂–C₄-alkylene, R¹⁴ being absent, and R¹⁵ being C₁–C₆-alkyl.

The following are representative compounds within the scope of the present invention:
Ctp-Leu-Asp-Phe-NH₂;
BOC-Trp-Leu-Asp-Tiq-NH₂;
β-Carboline-3-carbonyl-Leu-Asp-Phe-NH₂;
Nct-Leu-Asp-Phe-NH₂;
Ctp-Leu-Asp-(NMe)Phe-NH₂;
{2(S)-[3-(BOC-amino)-3-(1H-indol-3-ylmethyl)-2-oxo-1-pyrrolidinyl]-4-methylpentanoyl}-Asp-Phe-NH₂;
(2H-2-aza-benzo[cd]azulene-8-carboxyl)-Leu-Asp-Phe-NH₂
D-Ctp-Leu-Asp-Phe-NH₂;
2-Naphthoyl-(dehydro)Phe-Leu-Asp-Phe-NH₂;
1-Naphthoyl-(dehydro)Phe-Leu-Asp-Phe-NH₂;
BOC-Trp-Leu-Asp-(dehydro)Phe-NH₂;
Ctp-Leu-Asp-(dehydro)Phe-NH₂;
BOC-Trp-Tpp-Asp-(NMe)Phe-NH₂;
BOC-Trp-Nle-Asp-(dehydro)Phe-NH₂;
Nᵅ-BOC-Nⁱⁿ-formyl-Trp-Leu-Asp-Phe-NH₂;
(2′,3′-Dihydro)Trp-Leu-Asp-Phe-NH₂;
BOC-[5-amino-2-(1H-indol-3-ylmethyl)pentanoyl]-Leu-Asp-Phe-NH₂;
BOC-[5-amino-2-(1H-indol-3-ylmethyl)-2-pentenoyl]-Leu-Asp-Phe-NH₂;
Nᵅ-BOC-(Nⁱⁿ-propionyl)Trp-Leu-Asp-Phe-NH₂;
BOC-[8-amino-2-(1H-indol-3-ylmethyl)-2-octenoyl]-Leu-Asp-Phe-NH₂;
BOC-Glyψ(CH=CH)Trp-Leu-Asp-Phe-NH₂;
Ctp-Leu-Asp-Phe-NHNH₂;

BOC-Trp-Leu-Asp-Trp-NH$_2$;
BOC-Trp-Leu-Asp-$\beta$-Nal-NH$_2$;
BOC-Trp-Leu-Asp-$\alpha$-Nal-NH$_2$;
BOC-Trp-Pro-Asp-Phe-NH$_2$;
BOC-Trp-Tpp-Asp-Phe-NH$_2$;
Ctp-Tpp-Asp-Phe-NH$_2$;
BOC-$\alpha$-Nal-Leu-Asp-Phe-NH$_2$;
BOC-$\beta$-Nal-Leu-Asp-Phe-NH$_2$;
BOC-Trp-Leu-Asp-[3(S)-benzyl-2-oxo-4-piperazine];
Ctp-Tpp-Asp-(NMe)Phe-NH$_2$;
Ctp-Cpp-Asp-Phe-NH$_2$;
BOC-Trp-Tpp-Asp-Trp-NH$_2$;
BOC-$\beta$-Nal-Tpp-Asp-$\alpha$-Nal-NH$_2$;
BOC-$\beta$-Nal-Tpp-Asp-$\beta$-Nal-NH$_2$;
Ctp-Tpp-Asp-$\alpha$-Nal-NH$_2$;
Ctp-Tpp-Asp-$\beta$-Nal-NH$_2$;
Ctp-Tpp-Asp-Cha-NH$_2$;
Ctp-(1,4-thiazane-3-carbonyl)-Asp-Phe-NH$_2$;
Ctp-Pip-Asp-Phe-NH$_2$;
BOC-Trp-(1,4-thiazepine-3-carbonyl)-Asp-Phe-NH$_2$
2-[3-(1h-indo-3-ylmethyl)-2,5-dioxo-1-piperazinyl]valeryl-Asp-Phe-NH$_2$;
2-[3-(1H-indol-3-ylmethyl)-2,5-dioxo-1-piperazinyl]isocaproyl-Asp-Phe-NH$_2$;
2-[3-(1H-indol-3-ylmethyl)-2,5-dioxo-1-piperazinyl]-caproyl-Asp-Phe-NH$_2$; and
2-[3-(2-Naphthylmethyl)-2,5-dioxo-1-piperazinyl]isocaproyl-Asp-Phe-NH$_2$;
as well as their pharmaceutically-acceptable salts.

The preferred compounds according to the present invention are represented by the formula (Ic), A-B-Y-Z, as defined above, and include the following representative compounds:
Ctp-Leu-Asp-Phe-NH$_2$;
BOC-Trp-Leu-Asp-Tiq-NH$_2$;
Ctp-Leu-Asp-(NMe)Phe-NH$_2$;
Ctp-Leu-Asp-(dehydro)Phe-NH$_2$;
BOC-Trp-Tpp-Asp-Phe-NH$_2$;
Ctp-Tpp-Asp-Phe-NH$_2$;
Ctp-Tpp-Asp-(NMe)Phe-NH$_2$;
Ctp-Cpp-Asp-Phe-NH$_2$;
BOC-Trp-Tpp-Asp-Trp-NH$_2$;
Ctp-Tpp-Asp-$\alpha$-Nal-NH$_2$;
Ctp-Tpp-Asp-$\beta$-Nal-NH$_2$;
Ctp-Tpp-Asp-Cha-NH$_2$;
Ctp-(1,4-thiazane-3-carbonyl)-Asp-Phe-NH$_2$; and
Ctp-Pip-Asp-Phe-NH$_2$;
as well as their pharmaceutically-acceptable salts.

As used throughout this specification and the appended claims, every use of a variable in a structure is independent of every other appearance of that variable.

"Alkyl" refers to a monovalent group of specified length derived from a straight- or branched-chain saturated hydrocarbon by the removal of a single hydrogen atom, and is exemplified by methyl, ethyl, n- and iso-propyl, n-, sec-, iso- and tert-butyl, and the like.

"Alkanoyl" represents an alkyl group, as defined above, attached to the parent molecular moiety through a carbonyl group, and is exemplified by acetyl, propionyl, butanoyl, and the like.

"Alkenyl" refers to a straight- or branched-chain of carbon atoms of specified length which contains a carbon-carbon double bond, including, but not limited to, vinyl, allyl, methallyl, propenyl, butenyl, isoprenyl, and the like.

"Alkenylene" refers to a spacer group of straight- or branched-chain carbon atoms containing a carbon-carbon double bond, including, but not limited to —CH=CH—, —C(CH$_3$)=CH—, —CH=CH—CH$_2$—, and the like.

"Alkoxy" refers to an alkyl group, as defined above, attached to the parent molecular moiety through an oxygen atom, and is exemplified by methoxy, ethoxy, iso-propoxy, butoxy, and the like.

"Alkoxycarbonyl" represents an ester group, i.e., an alkoxy group, attached to the parent molecular moiety through a carbonyl group such as methoxycarbonyl, ethoxycarbonyl, and the like.

"Alkylamino" refers to an alkyl group, as defined above, attached to the parent molecular moiety through a nitrogen atom and is represented by methylamino, ethylamino, and the like.

"Alkylene" refers to a spacer group of specified length derived from a straight- or branched-chain saturated hydrocarbon, including, but not limited to methylene, ethylene, iso-propylene, and the like.

"Alkylsulfonyl" refers to an alkyl group, as defined above, attached to the parent molecular moiety through a —SO$_2$— group.

"Aminoalkyl" refers to an alkyl group, as defined above, substituted by an amino group, including, but not limited to, 2-aminoethyl, 2-aminopropyl, 3-aminopropyl, 2-aminobutyl, and the like. "Benzohet", as used herein, refers to a 5- or 6-membered heterocyclic ring to which is fused a benzene ring, including, but not limited to, indolyl, indolinyl, benzofuryl, benzothienyl, benzimidazolyl, quinolyl, isoquinolyl, dihydroisoquinolyl, tetrahydroisoquinolyl, and the like.

"Carbotricyclic", as used herein, refers to a system of three fused carbocyclic rings, each ring containing five or six carbon atoms and each ring being unsaturated or saturated, including, but not limited to, adamantyl, phenanthryl, acenaphthyl, fluorenyl, dibenzosuberyl and 9,10-dihydrophenanthryl.

"Cyclo-C$_3$–C$_8$-alkyl" refers to a monocyclic alkyl radical having from three to eight carbon atoms, including, but not limited to, cyclopropyl, cyclobutyl, cyclopentyl, cyclohexyl, adamantyl, and the like.

"Dialkylamino" refers to two independently-selected alkyl groups attached to the parent molecular moiety through a nitrogen atom and is represented by dimethylamino, diethylamino, methylethylamino, and the like.

"Halo" or "halogen" refers to chloro, bromo, iodo or fluoro.

"Haloalkyl" denotes an alkyl group, as defined above, having one, two, or three halogen atoms attached thereto and is exemplified by such groups as chloromethyl, dichloromethyl, bromoethyl, fluoromethyl, 2-fluoroethyl, trifluoromethyl, and the like.

"Het", as used herein, refers to a 5- or 6-membered heterocyclic ring containing carbon atoms and: one or two nitrogen atoms; one sulfur or one oxygen atom; one nitrogen and one sulfur atom; or one nitrogen and one oxygen atom; wherein the 5-membered ring has 0–2 double bonds and the 6-membered ring has 0–3 double bonds; and wherein the nitrogen heteroatom may optionally be quaternized. Such heterocycles include, but are not limited to, pyridyl, pyrimidinyl, furyl, thienyl, pyrazolyl, oxazolyl, isoxazolyl, tetrahydrofuryl, imidazolyl, piperazinyl, piperidinyl, pyrrolidinyl, thiazolyl, isoxazolinyl, and the like.

"Heterotricycle", as used herein, refers to a system of three fused rings, one ring being a Het group as defined as above, and the other two rings being independently-selected from Het, as defined above, and benzene. Heterotricycles include, but are not limited to, carbazolyl, β-carbolinyl, dibenzofuryl, xanthanyl, phenanthranyl, benzisoindolinyl, and the like.

"Hydroxyalkyl" represents an alkyl group, as defined above, substituted by one hydroxyl group.

"Mono- or disubstituted benzohet", as used herein, refers to one or two substituents on a benzohet group, as defined above, independently selected from $C_1$–$C_6$-alkyl, halogen, halo-$C_1$–$C_6$-alkyl, $C_1$–$C_6$-alkoxy, $C_1$–$C_6$-alkanoyl, $C_1$–$C_6$-alkoxycarbonyl, formyl, carboxy, benzyloxy, thio-$C_1$–$C_6$-alkoxy, $C_1$–$C_6$-alkylamino, di-$C_1$–$C_6$-alkylamino, hydroxy, nitro, $C_1$–$C_6$-alkylsulfonyl, as defined above, and —$OSO_3H$.

"Mono- or disubstituted Het", as used herein, refers to Het, as defined above, substituted with one or two substituents independently selected from $C_1$–$C_6$-alkyl, halogen, halo-$C_1$–$C_6$-alkyl, $C_1$–$C_6$-alkoxy, $C_1$–$C_6$-alkanoyl, $C_1$–$C_6$-alkoxycarbonyl, formyl, carboxy, benzyloxy, thio-$C_1$–$C_6$-alkoxy, $C_1$–$C_6$-alkylamino, di-$C_1$–$C_6$-alkylamino, hydroxy, nitro, $C_1$–$C_6$-alkylsulfonyl, as defined above, and —$OSO_3H$.

"N-protected" refers to an amino-nitrogen atom protected by an N-protecting group, as defined below.

"N-protecting" refers to a group intended to protect an amino group or the N-terminus of an amino acid or peptide against undesirable reactions during a synthetic procedure or to prevent the attack of exopeptidases on the compound or to increase the solubility of the compound and includes, but is not limited to, sulfonyl; acyl, such as acetyl, pivaloyl and benzoyl; alkoxycarbonyl, such as t-butyloxycarbonyl (BOC), benzyloxycarbonyl (Cbz); or an L- or D-aminoacyl residue, which may itself be N-protected. Other examples may be found in Volume 3 of *The Peptides*, E. Gross and J. Meienhofer, Academic Press, 1981.

"Pharmaceutically-acceptable salts" refers to those salts, amides and esters which are, within the scope of sound medical judgement, suitable for use in contact with the tissues of humans and lower animals without undue toxicity, irritation, allergic response and the like, and are commensurate with a reasonable benefit/risk ratio. Pharmaceutically-acceptable salts are well known in the art, see, for example, S. M Berge, et al., *J. Pharmaceutical Sciences*, 1977, 66: 1–19. These salts may be prepared according to conventional methods in situ during the final isolation and purification of the compounds of formula (I), or separately by reacting the free base with a suitable organic acid or base. Representative acid addition salts of the amine include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, gluconate, glycerophosphate, hemisulfate, heptanoate, hexanoate, hydrobromide, hydrochloride, hydroiodide, 2-hydroxy-ethanesulfonate, lactobionate, lactate, laurate, lauryl sulfate, maleate, methanesulfonate, 2-naphthalenesulfonate, nicotinate; oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts of the phenolic hydroxyl group include sodium, calcium, potassium, magnesium salts and the like.

"Mono-substituted naphthyl", as used herein, refers to a naphthyl group which is substituted with one substituent selected from $C_1$–$C_6$-alkyl, halogen, halo-$C_1$–$C_6$-alkyl, $C_1$–$C_6$-alkoxy, benzyloxy, thio-$C_1$–$C_6$-alkoxy, hydroxy, alkanoyl, carboxy, amino, $C_1$–$C_6$-alkylamino, di-$C_1$–$C_6$-alkylamino, as defined above, nitro and —$OSO_3H$.

"Substituted naphthoyl" refers to a substituted naphthyl group, as defined above, attached to the parent molecular moiety through a carbonyl group, and is exemplified by naphthoyl, 6-methylnaphthoyl, 5-chloronaphthoyl, and the like.

"Mono-substituted phenyl", as used herein, refers to a phenyl group which is substituted with one substituent selected from $C_1$–$C_6$-alkyl, halogen, halo-$C_1$–$C_6$-alkyl, $C_1$–$C_6$-alkoxy, benzyloxy, thio-$C_1$–$C_6$-alkoxy, hydroxy, $C_1$–$C_6$-alkanoyl, carboxy, amino, $C_1$–$C_6$-alkylamino, di-$C_1$–$C_6$-alkylamino, as defined above, nitro and —$OSO_3H$.

"Thioalkoxy" refers to an alkoxy group, as defined above, wherein a sulfur atom is substituted for the oxygen atom.

All amino acid residues identified herein are in the natural L-configuration unless otherwise designated with "D", (e.g., D-Trp). In keeping with standard peptide nomenclature, *J. Biol. Chem.*, 243:3557–59, (1969), abbreviations for amino acid residues are used herein. The compounds of formula (I) contain two or more asymmetric carbon atoms and thus can exist as pure diastereomers, mixtures of diastereomers, diastereomeric racemates or mixtures of diastereomeric racemates. The present invention includes within its scope all of the isomeric forms.

Other abbreviations used herein are as shown in the following Table:

TABLE OF CORRESPONDENCE

| SYMBOL | REPRESENTS |
| --- | --- |
| Tyr | L-tyrosine |
| Gly | glycine |
| Phe | L-phenylalanine |
| Ala | L-alanine |
| Ile | L-isoleucine |
| Leu | L-leucine |
| Thr | L-threonine |
| Val | L-valine |
| Lys | L-lysine |
| Gln | L-glutamine |
| Glu | L-glutamic acid |
| Trp | L-tryptophan |
| Arg | L-arginine |
| Asp | L-aspartic acid |
| Asn | L-asparagine |
| Cys | L-cysteine |
| α-Nal | 3-(1-naphthyl)alanine |
| β-Nal | 3-(2-naphthyl)alanine |
| Cha | 3-(cyclohexyl)alanine |
| Pip | pipecolinic acid |
| Ctp | 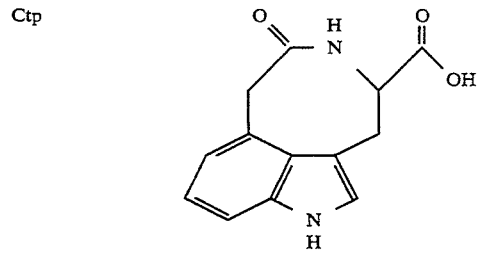 |
| Tpp | 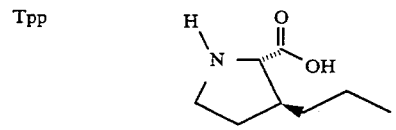 |

TABLE OF CORRESPONDENCE-continued

| SYMBOL | REPRESENTS |
| --- | --- |
| Cpp | (structure) |
| Nct | (structure) |
| (Dehydro)Phe | (structure) |

The abbreviation ψ(CH=CH) indicates that the amide (—C(O)NH—) bond of a peptide has been replaced by a double bond. For example, Trpψ(CH=CH)Leu represents a tryptophan residue bonded to a leucine residue wherein the amide bond is replaced as shown below.

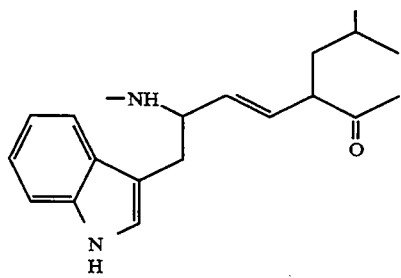

It is noted that all amino acid residue sequences are represented herein by formulae whose left to right orientation is in the conventional direction of amino-terminus to carboxy-terminus.

General Synthetic Procedures

The compounds of the present invention, represented by formula (I), can be prepared via a number of processes that are considered standard in peptide synthesis. A detailed description of these methods is contained in *The Peptides*, Vol. 1, Gross and Meienhofer, Eds., Academic Press, New York, 1979. Coupling methods that are employed include the carbodiimide method (e.g., using 1,3-dicyclohexylcarbodiimide [DCC] or 1-(3-dimethylaminopropyl-3-ethylcarbodiimide hydrochloride [EDCI]) with the option of racemization-preventing additives (1-hydroxybenzotriazole [HOBt]), the mixed anhydride method (typically using isobutyl chloroformate), the azide method, the acid chloride method, the symmetrical anhydride method, the use of bis(2-oxo-3-oxazolidinyl)phosphinic chloride (BOP-Cl), and the active ester method (e.g. N-hydroxysuccinimide esters, 4-nitrophenol esters, 2,4,5-trichlorophenol esters, and the like).

The compounds of the invention are prepared by stepwise coupling of the amino acids or by coupling together fragments of dipeptide length or greater. Thus, the free carboxylic acid moiety from one amino acid or peptide fragment is activated and allowed to condense with the free nitrogen group of the second amino acid or peptide fragment. The coupling reactions are conducted in solvents such as methylene chloride ($CH_2Cl_2$), tetrahydrofuran (THF). dimethylformamide (DMF) or other such solvents under an inert atmosphere such as nitrogen ($N_2$) or argon (Ar).

During the coupling process, the non-participating carboxylic acids or amines on the reacting set of amino acids or peptide fragments are protected by protecting groups which can be selectively removed at a later time if desired. A detailed description of these groups and their selection and chemistry is contained in *The Peptides*, Vol. 3, Gross and Meienhofer, Eds., Academic Press, New York 1981. Thus, useful protective groups for the amino groups are benzyloxycarbonyl (Cbz), t-butyloxycarbonyl (BOC), 2,2,2-trichloroethoxycarbonyl (Troc), t-amyloxycarbonyl, 4-methoxybenzyloxycarbonyl, 2-(trimethylsilyl)ethyoxycarbonyl, 9-fluorenylmethoxycarbonyl (FMOC), phthaloyl, acetyl, formyl, trifluoroacetyl, and the like.

Examples of useful protective groups for the carboxylic acid includes esters such as methyl, ethyl, cyclohexyl, benzyl, t-butyl, 2,2,2-trichloroethyl, allyl, 4-nitrobenzyl, 4-pyridylmethyl, and the like. Removal of these protecting groups can be accomplished selectively by employing hydrogenolytic, various acid or base catalyzed hydrolytic, thermal or dissolving metal conditions.

As in conventional peptide synthesis, branched chain amino and carboxyl groups at the alpha and omega positions in the amino acids may be protected and deprotected if necessary. The protecting groups for amino groups which can be used involve, for example, benzyloxycarbonyl (Cbz), o-chlorobenzyloxycarbonyl ((2-Cl)Z), p-nitrobenzyloxycarbonyl (Z($NO_2$)), p-methoxybenzyloxycarbonyl (Z(OMe)), t-butoxycarbonyl (BOC), t-amyloxycarbonyl (Aoc), isobornyloxycarbonyl, adamantyloxycarbonyl (Adoc), 2-(4-biphenyl)-2-propyloxycarbonyl (Bpoc), 9-fluorenylmethoxycarbonyl (Fmoc), methylsulfonylethoxycarbonyl (Msc), trifluoroacetyl, phthaloyl, formyl, 2-nitrophenylsulfenyl (Nps), diphenylphosphinothioyl (Ppt) and dimethylphosphinothioyl (Mpt).

For the production of a compound of the invention where any one or several of the constituent amino acids bear an N-alpha-alkyl group, specifically methyl, the corresponding N-alpha-alkyl amino acid can be prepared via the method described by Benoiton (*Can. J. Chem.*, 1977, 55: 906) or Shuman (*Peptides: Proceedings of the Seventh American Peptide Symposium*, D. Rich, E. Gross, Eds., Pierce Chemical Co., Rockford, Ill. 1982, p 617) wherein the BOC or Cbz protected amino acid is treated with a base in the presence of a chelating agent such as a crown ether and then quenched with methyl iodide. An alternative method described by Freidinger (*J. Org. Chem.*, 1983, 48:77) in which triethylsilane reduction of the oxazolidinone of an amino acid directly produces the N-alphamethyl derivative can also be utilized.

UTILITY

The compounds of formula (I) are CCK ligands selective for the Type-B receptor, which is found predominantly in the brain, and are useful in the treatment and prevention of CCK-related disorders in man or other mammals. As CCK agonists at the Type-B receptor, the compounds of the invention mimic the effects of CCK on CCK Type-B receptors. The compounds of the invention are useful in the treatment or prevention of CCK-related disorders of the central nervous and gastrointestinal systems. The compounds of the invention are useful in the treatment of substance abuse, including alcohol and nicotine addiction and also including drugs of abuse such as cocaine, amphetamines, heroin, cannabinoids (THC and the like), phencyclidine (PCP) and the like. The compounds of the invention are also useful in the treatment of disorders of memory and cognition, and treatment of shock, respiratory and cardiocirculatory insufficiencies. The compounds of the invention are also useful in the treatment of eating disorders related to appetite control.

The ability of the compounds of the invention to interact with Type-B CCK receptors has been demonstrated in vitro by radioligand binding experiments (Example 50 below), and the ability to act as CCK agonists has been demonstrated in experiments stimulating calcium mobilization at Type-B CCK receptors in small cell lung cancer cell lines (Example 51 below).

While not intending to be bound by any theoretical mechanisms of action, the ability of the compounds of this invention to treat substance abuse is thought to result from the ability of the compounds of this invention to enhance response of neurons in the brain (specifically in the ventral tegmental area of Tsai (VTA)) to substances of abuse such as ethanol, nicotine and others. Both ethanol (Gessa, et al., *Brain Research*, 1985, 348:201, Brodie, et al., *Brain Research*, 1990, 508:65 and nicotine (Mereu, et al., *Eur. J. Pharmacol.*, 1987, 141:395 and Brodie and Mueller, *Soc. Neurosci. Abstr.*, 1988, 14:1327) affect VTA neurons by increasing their firing rate. By enhancing the excitation of these neurons which is induced by the abused substance, smaller amounts of the addictive substance will be required, in the presence of the CCK agonists of this invention, to produce the same rewarding effects as in its absence. This will permit an addicted individual to ingest lessened amounts of the abused substance to achieve the accustomed reward sensation, while alleviating the deleterious side effects associated with the higher doses of these drugs. The ability of the compounds of the invention to potentiate the response of VTA neurons to ethanol has been demonstrated (Example 52 below).

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

The pharmaceutically-acceptable salts of the present invention can be synthesized from the compounds of formula (I) which contain a basic or acidic moiety by conventional chemical methods. Generally, the salts are prepared by reacting the free base or acid with stoichiometric amounts or with an excess of the desired salt forming inorganic or organic acid or base in a suitable solvent or various combinations of solvents.

Example of acids which may be employed to form pharmaceutically-acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The pharmaceutically-acceptable salts of the acids of formula (I) are also readily prepared by conventional procedures such as treating an acid of formula (I) with an appropriate amount of a base, such as an alkali or alkaline earth metal hydroxide e.g. sodium, potassium, lithium, calcium, or magnesium, or an organic base such as an amine, e.g., dibenzylethylenediamine, cyclohexylamine, dicyclohexylamine, trimethylamine, piperidine, pyrrolidine, benzylamine and the like, or a quaternary ammonium hydroxide such as tetramethylammonium hydroxide and the like.

When a compound of formula (I) is used as an agonist of CCK in a human subject, the total daily dose administered in single or divided doses may be in amounts, for Example, from 0.001 to 1000 mg a day and more usually 1 to 100 mg. Dosage unit compositions may contain such amounts of submultiples thereof to make up the daily dose.

The amount of active ingredient that may be combined with the carrier materials to produce a single dosage form will vary depending upon the host treated, the particular treatment and the particular mode of administration.

It will be understood, however, that the specific dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidentally with the specific compound employed; and like factors well known in the medical arts.

Injectable preparations, for example, sterile injectable aqueous or oleagenous suspensions, may be formulated according to the known art using suitable dispersing or wetting agents and suspending agents. The sterile injectable preparation may also be a sterile injectable solution or suspension in a nontoxic parenterally acceptable diluent or solvent, for Example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The injectable formulation may be sterilized, for example, by filtration through a bacteria-retaining filter, or by incorporating sterilizing agents in the form of sterile solid compositions which may be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms may also be made by forming microcapsule matrices of drugs and biodegradable polymers such as polylactide-polyglycolide. Depending on the ratio of drug to polymer and the composition of the polymer, the rate of drug release may be controlled. Examples of other biodegradable polymers include poly-orthoesters and polyanhydrides. The depot injectables may also be made by entrapping the drug in liposomes or microemulsions which are compatible with body tissues.

Liquid dosage forms for oral administration may include pharmaceutically-acceptable emulsion, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Suppositories for rectal administration of the drug can be prepared by mixing the drug with a suitable nonirritating excipient such as cocoa butter and polyethylene glycols which are solid at room temperatures but liquid at the rectal temperature and will therefore melt in the rectum and release the drug.

Solid dosage forms for oral administration may include capsules, tablets, pills, prills, powders, and granules. In such solid dosage form, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Solid compositions of a similar type may also be employed as fillers in soft and hard-filled gelatin capsules using such excipients as lactose or milk sugar as well as high molecular weight polyethylene glycols and the like.

The active compounds may also be in micro-encapsulated form with one or more excipients as noted above. The solid dosage forms of tablets, dragees, capsules, pills, and granules can be prepared with coatings and shells such as enteric coatings and other coatings well known in the pharmaceutical formulating art.

They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or patches. The active component is admixed under sterile conditions with a pharmaceutically-acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to the compounds of this invention, excipients such as lactose, talc, silicic acid, aluminum hydroxide, calcium silicates and polyamide powder, or mixtures of these substances. Sprays may additionally contain customary propellants such as chlorofluorohydrocarbons, or acceptable non-halogenated propellants.

Transdermal patches have the added advantage of providing controlled delivery of a compound to the body. Such dosage forms may be made by dissolving or dispersing the compound in the proper medium. Absorption enhancers may also be used to increase the flux of the compound across the skin. The rate may be controlled by either providing a rate controlling membrane or by dispersing the compound in a polymer matrix or gel.

The present agents can also be administered in the form of liposomes, As is known in the art, liposomes are generally derived from phospholipids of other lipid substances. Liposomes are formed by mono- or multi-lamellar hydrated liquid crystals that are dispersed in an aqueous medium. Any non-toxic, physiologically acceptable and metabolizable lipid capsule of forming liposomes can be used. The present compositions in liposome form can contain, in addition to the peptide of the present invention, stabilizers, preservatives, excipients, and the like. The preferred lipids are the phospholipids and the phosphatidyl cholines (lecithins), both natural and synthetic.

Methods to form liposomes are known in the art. See, for Example, Prescott, Ed., *Methods in Cell Biology*, Volume XIV, Academic Press, New York, N.Y. (1976), p 33. et seq.

The foregoing may be better understood by reference to the following Examples which are provided for illustration and not limitation of the invention.

EXAMPLE 1

CTP-Leu-Asp-Phe-NH$_2$

1a: Bromoacetyl-L-Trp-OBn

To a solution of L-Trp-OBn hydrochloride (15.0 g, 45.35 mmol) and triethylamine (9.18 g, 90.68 mmol) in absolute ethanol (200 mL) cooled to 0° C. was added bromoacetyl chloride (7.13 g, 45.34 mmol) dropwise over 10 minutes. The reaction mixture was stirred overnight with warming to ambient temperature. The solvent was removed in vacuo and the residue was partitioned between aqueous 0.1N HCl (250 mL) and ethyl acetate (250 mL). After drying over anhydrous sodium sulfate, the organic layer was concentrated in vacuo and the residue chromatographed on silica gel eluting with ethyl acetate/hexane to yield 12.60 g of the title compound as a clear colorless oil.

1b: 4-Benzyloxycarbonyl-6-oxo-3,4,5,6-tetrahydro-1H,5H-azocin[4,5,6-c,d]indole (Ctp-OBn)

The title compound was prepared by an adaptation of an original procedure reported by O. Yonemitsu et al. (J. Am. Chem. Soc., 1966, 88:3941–3945). A solution of Example 1a (6.7 g, 16.14 mmol) in 40% ethanol/water (1 L) at 80° C. was irradiated (Hanovia 450 W. Hg lamp/vycor filter) for 3 hours. The resulting mixture was concentrated in vacuo to 600 mL and the aqueous layer extracted with ethyl acetate (3×). After drying over anhydrous sodium sulfate, the solvent was removed in vacuo and the residue chromatographed (eluting with ethyl acetate) to yield a mixture of 2- and 4-substituted cyclized products (1.20 g) and unreacted starting material (4.90 g). The mixture was recrystallized (ethyl acetate/diethyl ether/hexane) to yield 0.45 g of the title compound as a white crystalline solid, mp 149°–151° C.; $^1$H NMR (DMSO-d$_6$, 300 MHz) δ3.42 (m, 3H), 4.10 (br d, 1H), 4.30 (br s, 1H), 5.25 (s, 2H), 6.75 (d, 1H), 6.94 (t, 1H), 7.12 (m, 3H), 7.30 (m, 5H). $[\alpha]_D^{23} = -75.1°$ (c 1.0; MeOH).

1c: Ctp-OH

A mixture of Example 1b (0.20 g, 0.60 mmol) and 5% palladium on barium sulfate (Pd/BaSO$_4$) (0.04 g) in methanol (10 mL) was hydrogenated under one atmosphere of hydrogen at ambient temperature for 0.5 hour. The catalyst was filtered and the solvent removed in vacuo to yield 0.13 g of free acid (Ctp-OH) as a pink solid sufficient for use without further purification.

1d: Ctp-Leu-Asp(OBn)-Phe-NH$_2$

To the acid (0.13 g, 0.55 mmol) from Example 1c above (or, alternately, from Example 49, below, after optical resolution) in DMF (8 mL) cooled to 0° C. were added Leu-Asp(OBn)-Phe-NH$_2$ hydrochloride (J. Martinez, et al, J. Med. Chem., 1985, 28:1874)(0.28 g, 0.55 mmol), diphenyl phosphoryl azide (0.18 g, 0.65 mmol) (DPPA), and N-methyl morpholine (NMM) (0.12 g, 1.20 mmol). The mixture was stirred overnight with warming to ambient temperature. The solvent was concentrated to 2 mL and the residue dissolved in ethyl acetate (50 mL). The organic layer was washed three times with saturated aqueous sodium bicarbonate (NaHCO$_3$) and three times with 0.1N hydrochloric acid (HCl). After drying over anhydrous sodium sulfate, the solvent was removed in vacuo. The residue was triturated from ethyl acetate/diethyl ether and the resulting solid collected and recrystallized from ethanol/water to yield 0.34 g of the title compound as a white solid in two crops; MS(FAB+) m/e 709 (M+H)+. $^1$H NMR (DMSO-d$_6$, 300 MHz) δ0.85 (m, 6H), 1.40 (m, 1H), 1.55 (m, 1H), 2.59 (m, 1H), 2.79 (m, 2H), 2.95 (m, 1H), 3.25–3.56 (m, 4H), 4.15 (m, 1H), 4.32 (m, 2H), 4.55 (m, 1H), 5.10 (s, 2H), 6.74 (d, 1H), 6.95 (t, 1H), 6.99 (d, 1H), 7.10 (m, 9H), 7.30 (m, 5H), 7.83 (d, 1H), 8.20 (d, 1H), 8.37 (d, 1H), 10.93 (br s, 1H).

1e: Ctp-Leu-Asp-Phe-NH$_2$

A mixture of Example 1c (0.21 g, 0.29 mol) and 5% Pd/BaSO$_4$ (0.05 g) in DMF (10 mL) was hydrogenated under one atmosphere hydrogen at ambient temperature overnight. The solvent was filtered twice through Celite® filter aid and concentrated to 1 mL. The solvent was triturated with ethyl acetate to yield 0.17 g of the title compound as a white solid, mp 236°–237.5° C. (dec). MS (FAB+) m/e 619 (M+H)+. $^1$H NMR (DMSO-d$_6$, 300 MHz) δ0.85 (m, 6H), 1.35 (m, 2H), 1.55 (m, 1H), 2.45 (m, 1H), 2.65 (m, 2H), 2.77 (m, 1H), 2.97 (m, 1H), 4.12 (m, 2H), 4.45 (q, 1H), 6.73 (d, 1H), 6.93 (t, 1H), 6.97 (d, 1H), 7.05 (m, 8H), 7.30 (br s, 1H), 7.83 (d, 1H), 8.18 (d, 1H), 8.27 (d, 1H), 10.93 (br s, 1H), 12.35 (br s, 1H). Anal calc for C$_{32}$H$_{38}$N$_6$O$_7$.H$_2$O: C, 60.35; H, 6.13; N, 13.20. Found: C, 60.71; H, 6.12; N, 13.15.

EXAMPLE 2

BOC-Trp-Leu-Asp-Tiq-NH$_2$

2a: 3(S)-1,2,3,4 Tetrahydroisoquinoline-3-carboxamide

Benzyl 3(S)-1,2,3,4-tetrahydroisoquinoline-3-carboxylate p-toluenesulfonate (11.68 g, 26.62 mmol), prepared according to the method of K. Hayashi et al., chem. Pharm. Bull., 1983, 31(1): 312–314, was partitioned between ethyl acetate (300 mL) and NaHCO$_3$ (300 mL). After drying over anhydrous sodium sulfate, the organic phase was filtered and the solvent removed in vacuo to yield 7.11 g of a slightly yellow oil. This oil (7.11 g) was dissolved in methanol and cooled to −20° C. The solution was saturated with dry gaseous ammonia, capped with a septum and allowed to stand at 0° C. overnight The solvent was removed in vacuo and the residue triturated with diethyl ether to yield 4.08 g of the title compound as a white solid, mp 157°–158° C. $[\alpha]_D^{23}$ −57° C. (c 1; MeOH).

2b: BOC-Asp(OBn)-Tiq-NH$_2$

To an ice cold suspension of Example 2a (7.0 g, 39.27 mmol) and BOC-Asp(OBn)OH (12.86 g, 39.27 mmol) in ethyl acetate (250 mL) were added 4-dimethylamino pyridine (4-DMAP) (0.97 g, 0.79 mmol), and N,N'-dicyclohexylcarbodiimide (DCCl) (9.84 g, 47.72 mmol) in ethyl acetate (20 mL). The reaction mixture was stirred at 0° C. for 4 hours and then the solution was filtered. The organics were washed with aqueous solutions of 0.1N HCl (3×) and saturated NaCHO$_3$ (3×). After drying over anhydrous sodium sulfate, the solvent was removed in vacuo and the residue chromatographed (ethyl acetate/hexanes) to yield 10.10 g of the title compound as a white amorphous solid; MS (EI) m/e 481 (M+). $^1$H NMR (CDCl$_3$, 300 MHz) δ1.39 (s, 9H), 2.78 (dd, 1H), 2.93 (dd, 1H), 3.15 (dd, 1H), 3.45 (dd, 1H), 7.48 (m, 1H), 4.95 (m, 6H), 5.30 (m, 1H), 6.63 (br s, 1H), 7.13 (m, 4H), 7.30 (m, 5H).

2c: BOC-Asp-Tiq-NH$_2$

A mixture of Example 2b (0.66 g, 1.38 mmol) and 10% palladium on carbon (Pd/C) (0.050 g) in methanol (25 mL) was hydrogenated under one atmosphere of hydrogen at ambient temperature for 0.5 hour. The catalyst was filtered and the solvent removed in vacuo to yield 0.54 g of the title compound as a white amorphous solid. $^1$H NMR (CDCl$_3$, 300 MHz) δ1.39 (br s, 9H), 2.70 (m, 1H), 2.98 (m, 2H), 3.25 (m, 1H), 4.77 , (m, 1H), 5.0 (m, 1H), 6.92 (br s, 1H), 7.12 (m, 4H), 7.30 (br s, 1H).

2d: Leu-Asp-Tiq-NH$_2$ Trifluoroacetate

A solution of Example 2c (0.54 g, 1.38 mmol) in acetic acid (5 mL) was treated with 1.4N HCl/acetic acid (10 mL) at ambient temperature for 0.5 hour. The solution was triturated with diethyl ether to yield 0.37 g of a hygroscopic white solid which was used without further purification. to a solution of the solid (0.37 g, 1.13 mmol) and BOC-Leu-N-hydroxy-succinimide ester (0.37 g, 1.13 mmol) in DMF (10 mL) cooled to 0° C. was added N,N-diisopropylethylamine (0.15 g, 1.13 mmol). The mixture was stirred overnight with warming to ambient temperature. The solvent was concentrated in vacuo to 5 mL and the residue was triturated with ethyl acetate to yield 0.42 g white solid containing diketopiperazine byproduct. The crude solid was treated with 80% trifluoroacetic acid/water for 0.3 hour and triturated with diethyl ether to yield 0.29 g of the title compound as a white solid devoid of the diketopiperazine byproduct. $^1$H NMR (DMSO-d$_6$, 300 MHz) $\delta$0.82 (m, 6H), 1.44 (m, 2H), 1.55 (m, 1H), 2.47 (m, 2H), 2.67 (m, 6H), 3.00 (dd, 1H), 3,2 (m, 1H), 3.67 (m, 1H), 4.33 (m, 1H), 4.55 (m, 1H), 7.15 (m, 5H), 7.30 (br s, 1H), 8.50 (m, 2H), 8.67 (m, 1H).

2e: BOC-Trp-Leu-Asp-Tiq-NH$_2$

To a solution of Example 2d (0.073 g, 0.14 mmol) in N,N-dimethylformamide (DMF) (3 mL) cooled to 0° C., were added BOC-Trp-2,4,5-trichlorophenyl ester (0.068 g, 1.14 mmol) and N,N-diisopropylethyl amine (0.18 g, 0.14 mmol). The mixture was stirred overnight with warming to ambient temperature. Cyclohexane (15 mL) and water (15 mL) were added and the mixture during gentle warming on a steam bath formed a turbid suspension. The solid was filtered and washed with cyclohexane (2×) to yield 0.11 g of the title compound as a white solid, mp 200°–201.5° C.; MS(EI) m/e 691 (M+). $^1$H NMR (DMSO-d$_6$, 300 MHz) $\delta$0.80 (m, 6H), 1.30 (s, 9H), 1.35 (m, 2H), 1.55 (m, 1H), 2.63 (m, 1H), 2.73 (m, 2H), 2.93 (m, 2H), 4.15 (m, 1H), 4.33 (m, 2H), 4.45 (q, 1H), 6.82 (d, 1H), 6.93 (t, 1H), 7.02 (t, 1H), 7.12 (br s, 1H), 7.15 (m, 6H), 7.55 (d, 1H), 8.82 (m, 2H), 8.25 (d, 1H), 10.78 (br s, 1H), 12.38 (br s, 1H). Anal calc for C$_{35}$H$_{45}$N$_6$O$_8$.H$_2$O: C. 60.43; H, 6.76; N, 12.09. Found: C, 60.50; H, 6.61; N, 11.95.

EXAMPLE 3

β-Carboline-3-carbonyl-Leu-Asp-Phe-NH$_2$

3a: β-Carboline-3-carbonyl-Leu-Asp(OBn)-Phe-NH$_2$

To a solution of β-carboline-3-carboxylic acid (0.15 g, 0.70 mmol) (prepared according to the method of M. Cain et al. *J. Med. Chem.*, 1982, 25, 1081–1091) in DMF (10 mL) cooled to 0° C., were added Leu-Asp(OBn)-Phe-NH$_2$ hydrochloride (0.37 g, 0.70 mmol), diphenylphosphoryl azide (0.21 g, 0.78 mmol), and triethyl amine (0.14 g, 1.41 mmol). The mixture was stirred overnight with warming to ambient temperature. Ethyl acetate (30 mL) was added and the organic phase washed with aqueous solutions of 0.10N HCl (3×) and 0.50N NaOH (3×). After drying over anhydrous sodium sulfate, the solvent was removed in vacuo and the residue triturated with cold ethyl acetate to yield 0.26 g of the title compound as a yellow solid, mp 187°–189.5° C. MS(FAB+) m/e 677 (M+H)+. $^1$H NMR(DMSO-d$_6$, 300 MHz) $\delta$0.85 (m, 6H), 1.45 (m, 3H), 2.57 (dd, 1H), 2.80 (m, 2H), 2.95 (dd, 1H), 4.33 (m, 1H), 4.60 (m, 2H), 5.0 (m, 2H), 7.07 (m, 13H), 7.57 (m, 2H), 7.93 (d, 1H), 8.35 (d, 1H), 8.55 (dd, 2H), 8.87 (s, 1H), 8.93 (d, 1H), 12.00 (br s, 1H). Anal calc for C$_{38}$H$_{40}$N$_6$O$_6$.0.5H$_2$O: C, 66.29; H, 5.83; N, 12.26. Found: C, 66.29; H, 5.68; N, 12.03.

3b: β-Carboline-3-carbonyl-Leu-Asp-Phe-NH$_2$

A mixture of Example 3a (0.15 g, 0.22 mmol) and 5% Pd/BaSO$_4$ (0.035 g) in methanol (10 mL) was hydrogenated under one atmosphere of hydrogen at ambient temperature for 1.2 hour. The catalyst was filtered and the solvent removed in vacuo. The residue was dissolved in methanol (1 mL) and triturated with diethyl ether to yield 0.96 g of the title compound as a tan solid; MS(FAB+) m/e 587 (M+H)+. $^1$H NMR (DMSO-d$_6$, 300 MHz), $\delta$0.85 (m, 6H), 1.45 (m, 3H), 2.43 (m, 1H), 2.66 (dd, 1H), 2.80 (m, 2H), 3.00 (dd, 1H), 4.30 (m, 1H), 4.32 (m, 1H), 4.62 (m, 1H), 7.06 (m, 1H), 7.15 (m, 4H), 7.26 (m, 2H), 7.56 (m, 2H), 7.94 (d, 1H), 8.35 (d, 1H), 8.51 (dd, 2H), 8.85 (br s, 1H), 8.93 (d, 1H), 12.01 (br s, 1H), 12.35 (br s, 1H). Anal calc for C$_{31}$H$_{34}$N$_6$O$_6$.2H$_2$O: C, 59.80; H, 6.15; N, 13.50. Found: C, 59.80; H, 5.94; N, 13.36.

EXAMPLE 4

Nct-Leu-Asp-Phe-NH$_2$

4a: 2-Bromo-nonanoic acid

To a mixture of nonanoic acid (20 g, 126 mmol) and bromine (24.3 g 152 mmol) was added phosphorous trichloride (5.2 g, 38 mmol) slowly over 0.5 hour. The mixture was refluxed for 3 days and then diluted with ethyl acetate (200 mL). The organic phase was washed with aqueous saturated NaHSO$_3$ (3×), separated, dried over anhydrous sodium sulfate, and the solvent removed in vacuo to yield 27.0 g of the title compound as a brown oil. $^1$H NMR (CDCl$_3$, 60 MHz) $\delta$0.70 (m, 3H), 1.20 (m, 9H), 1.90 (m, 3H), 4.13 (m, 1H), 10.80 (br s, 1H).

4b: 2-Bromo-nonanoyl-Trp-OBn

To a solution of Example 4a (1.5 g, 6.30 mmol) in ethyl acetate (150 mL) cooled to 0° C. were added L-Trp-OBn hydrochloride (2.10 g, 6.30 mmol), triethylamine (0.64 g, 6.30 mmol) and N,N' dicyclohexylcarbodiimide (1.57 g, 7.60 mmol). The resulting suspension was stirred overnight with warming to ambient temperature. The solution was filtered and the supernatant was washed with aqueous solutions of 0.1N HCl (3×) and 0.5N NaOH (3×). After drying over anhydrous sodium sulfate, the solvent was removed in vacuo to yield 3.10 g of the title compound as a brown oil. $^1$H NMR (CDCl$_3$, 60 MHz) $\delta$0.80 (m, 3H), 1.10 (br s, 9H), 1.67 (m, 3H), 3.20 (d, 2H), 3.95 (t, 1H), 4.55 (m, 1H), 4.95 (br s, 2H), 6.60 (m, 2H), 6.93 (m, 8H), 7.72 (m, 2H).

4c: 4-Benzyoxycarbonyl-6-oxo-7-heptyl-3,4,6,7,tetrahydro-1H-5H azocin[4,5,6-c,d] indole.(Nct-OBn)

A solution of Example 4b (3.10 g, 6.0 mmol) in 40% ethanol/water (1 L) was reacted under similar conditions to those described in Example 1b. The residue was chromatographed (eluting with ethyl acetate/hexanes) to yield 0.19 g of the title compound as a waxy oil. MS (EI) m/e 432 (M+). $^1$H NMR (CDCl3, 300 MHz) $\delta$0.85 (m, 3H), 1.15 (m, 10H), 1.93 (m, 1H), 2.35 (m, 1H), 3.47 (dd, 1H), 3.93 (q, 1H), 4.43 (q, 1H), 4.80 (m, 1H), 5.19 (m, 2H), 6.20 (d, 1H), 6.75 (br s, 1H), 7.05 (d, 1H), 7.13 (t, 1H), 7.20 (d, 1H), 7.93 (m, 5H), 8.00 (br s, 1H).

4d: Nct-OH

A mixture of Example 4c (0.16 g, 0.37 mmol), and 5% Pd/BaSO$_4$ in methanol (5 mL) was hydrogenated under one atmosphere hydrogen at ambient temperature for 1.0 hour. The catalyst was filtered and the solvent removed in vacuo to yield 0.13 g of the title compound as a light orange powder. $^1$H NMR(DMSO-d$_6$, 300 MHz) $\delta$0.84 (m, 3H), 1.15 (m, 9H), 2.12 (m, 1H), 3.40 (m, 2H), 3.86 (m, 1H), 4.34 (m, 1H), 6.73 (d, 1H), 6.96 (t, 1H), 7.13 (d, 1H), 7.16 (br s, 1H), 7.18 (m, 1H), 8.23 (d, 1H), 10.85 (br s, 1H).

4e: Nct-Leu-Asp(OBn)-Phe-NH$_2$

A solution of Example 4d (0.13 g, 0.37 mmol), Leu-Asp(OBn)-Phe-NH₂ hydrochloride (0.21 g, 0.37 mmol), N-methylmorpholine (0.09 g, 0.91 mmol), and DPPA (0.11 g, 0.41 mmol) in DMF (3 mL) was stirred at 0° C. for 3 days. The solvent was concentrated in vacuo to 1 mL and diluted with ethyl acetate (30 mL). The organics were washed with aqueous solutions of 0.1N HCl (3×) and 0.5N NaOH (3×). After drying over anhydrous sodium sulfate, the solvent was removed in vacuo and the residue triturated with cold ethyl acetate to yield 0.60 g of the title compound as a tan solid; MS (FAB+) m/e 806 (M+H)+. ¹H NMR(DMSO-d₆, 300 MHz) δ0.75 (m, 9H), 1.15 (m, 12H), 1.45 (m, 3H), 1.80 (m, 1H), 2.05 (m, 1H), 2.43 (dd, 1H), 2.93 (q, 1H), 3.05 (dd, 1H), 3.30 (m, 2H), 3.55 (m, 1H), 3.93 (m, 1H), 4.25 (m, 2H), 4.50 (m, 1H), 4.65 (m, 1H), 6.75 (d, 1H), 7.02 (m, 13H).

4f: Nct-Leu-Asp-Phe-NH₂

A mixture of Example 4e (0.045 g, 0.056 mmol) and 5% Pd/BaSO₄ (10 mg) was hydrogenated under one atmosphere of hydrogen at ambient temperature for 1.0 hour. The catalyst was filtered, the solvent removed in vacuo, and the residue chromatographed on silica gel eluting with ethyl acetate/pyridine/acetic acid/water (31.4/4.0/1.2/2.2). The solvents were removed in vacuo and the residue suspended in water (2 mL) and lyophilized to yield 0.014 g of the title compound as a white solid; MS(FAB+) m/e 717 (M+H)+. ¹H NMR(DMSO-d₆, 300 MHz) δ0.70 (m, 9H), 1.10 (m, 12H), 1.55 (m, 1H), 1.70 (m, 1H), 2.05 (m, 1H), 2.30 (m, 2H), 2.65 (m, 1H), 2.98 (m, 1H), 3.05 (m, 1H), 3.40 (m, 1H), 3.55 (m, 1H), 3.70 (m, 1H), 4.25–4.60 (m, 3H), 6.71 (d, 1H), 6.75–7.10 (m, 10H), 7.45 (br s, 1H), 8.01 (d, 1H), 8.05 (br s, 1H), 8.25 (d, 1H), 10.85 (br s, 1H). Anal calc for C₄₀H₅₂N₆O₇·2.5H₂O: C, 62.08; H, 7.42; N, 10.86. Found C, 62.00; H, 7.09; N, 10.65.

EXAMPLE 5

Ctp-Leu-Asp-(NMe)Phe-NH₂

5a: Ctp-Leu-Asp(OBn)-(NMe)Phe-NH₂

To a solution of CTP-OH (0.096 g, 0.40 mmol), as prepared in Example 1c, and Example 5 g (0.21 g, 0.40 mmol) in DMF (5 mL) cooled to 0° C. were added DPPA (0.13 g, 0.47 mmol) and N-methylmorpholine (0.087 g, 0.87 mmol). The mixture was stirred overnight with warming to ambient temperature. Ethyl acetate (50 mL) was added and the organics washed with aqueous solutions of 0.1N HCl (3×) and saturated NaHCO₃ (3×). After drying over anhydrous sodium sulfate, the solvent was removed in vacuo and the residue chromatographed (ethyl acetate) to yield 0.10 g of the title compound as a white solid; MS(FAB+) m/e 723 (M+H)+. ¹H NMR(DMSO-d₆, 300 MHz) δ0.83 (m, 7H), 1.23 (m, 1H), 1.30 (m, 1H), 1.52 (m, 1H), 2.12–2.60 (m, 1H), 2.62–2.95 (m, 4H), 3.06–3.50 (m, 6H), 4.13 (m, 3H), 4.53–5.12 (m, 3H), 6.73 (d, 1H), 6.92–7.25 (m, 9H), 7.34 (m, 5H), 7.48 (br s, 1H), 8.12 (dd, 2H), 8.37 (d, 1H), 8.61 (d, 1H), 10.90 (br s, 1H).

5b: Ctp-Leu-Asp-(NMe)Phe-NH₂

A mixture of Example 5a (0.96 g, 0.13 mmol) and 5% Pd/BaSO₄ (0.015 g), in methanol was hydrogenated under one atmosphere of hydrogen at ambient temperature for 0.5 hour. The catalyst was filtered and the solvent removed in vacuo to yield 0.075 g of the title compound as a tan solid; MS(FAB+) m/e 633 (M+H)+. ¹H NMR(DMSO-d₆, 300 MHz) δ0.82 (m, 7H), 1.23 (m, 1H), 1.31 (m, 1H), 1.51 (m, 5H), 2.12–2.60 (m, 1H), 2.56–3.60 (m, 6H), 4.12 (m, 3H), 4.54 (m, 1H), 4.33 (m, 1H), 5.10 (m, 1H), 6.73 (m, 1H), 6.92 (m, 2H), 7.10 (m, 6H), 7.45 (m, 2H), 8.10 (d, 1H), 8.19 (d, 1H), 8.59 (d, 1H), 10.91 (br s, 1H). Anal calc for C₃₃H₄₀N₆O₇·2H₂O: C, 59.25; H, 6.58; N, 12.57. Found: C, 59.31; H, 6.44; N, 12.00.

EXAMPLE 6

{2(S)-[3-(BOCamino)-3-(1H-indol-3-ylmethyl)-2-oxo-1-pyrrolidinyl]-4-methylpentanoyl}-Asp-Phe-NH₂

6a: 2(S)-[3-Carboxy-3-(1H-indol-3-ylmethyl)-2-oxo-1-pyrrolidinyl]-4-methylpentanoic acid methyl ester 2(S)(3-carboxy-2-oxo-1-pyrrolidinyl)-4-methyl pentanoic acid methyl ester was prepared according to the method of R. M. Freidinger, *J.Org.Chem.*, 1985, 50 (19):3631–3633. A solution of isopropylidene cyclopropane-1,1-dicarboxylate (5.0 g, 29.30 mmol), leucine methyl ester hydrochloride (5.31 g, 29.3 mmol), and triethylamine (2.97 g, 29.3 mmol) in degassed DMF (50 mL) was heated at 65° C. for 1 hour. The solution was cooled to ambient temperature and poured into a mixture of 10% aqueous sulfuric acid (H₂SO₄) (100 mL) and ethyl acetate (100 mL). The organic layer was separated. After drying with Na₂SO₄, the solvent was removed in vacuo to yield 7.55 g of a brown oil. To the crude oil (7.55 g) in degassed DMF (50 mL) were added 3-(dimethylaminomethyl)indole (gramine) methiodide (13.2 g, 42.94 mmol) and 1,8-diazabicyclo[5.4.0]undec-7-ene (DBU) (5.16 g, 33.90 mmol). The mixture was heated at 85° C. for 18 hours and cooled to ambient temperature. The mixture was poured into ethyl acetate (100 mL) and saturated aqueous NaHCO₃ (100 mL). The aqueous phase was separated, acidified to pH 3–4 with 10% aqueous H₂SO₄, and extracted with ethyl acetate (3×). After drying with Na₂SO₄, the solvent was removed in vacuo and the residue chromatographed (eluting with 1% acetic acid/ethyl acetate) to yield 1.56 g of the title compound as a white solid; MS(FAB+) m/e 387 (M+H)+. ¹H NMR(DMSO-d₆, 300 MHz) δ0.65 (m, 6H), 1.23–1.80 (m, 3H), 1.90 (m, 1H), 2.12 (m, 1H), 2.77–3.48 (m, 6H), 3.51 (m, 3H), 4.98 (m, 1H), 6.92 (m, 3H), 7.28 (d, 1H), 7.97 (d, 1H), 10.90 (br s, 1H), 12.70 (br s, 1H).

6b: 2(S)-[3-(BOCamino)-3-(1H-indol-3-ylmethyl)-2-oxo-1-pyrrolidinyl]-4-methylpentanoic acid methyl ester A solution of Example 6a (1.22 g, 3.16 mmol), and DPPA (0.96 g, 3.49 mmol) in t-butyl alcohol (50 mL) was refluxed for 48 hours under nitrogen. The solvent was removed in vacuo and the residue chromatographed (ethyl acetate/hexanes) to yield 0.48 g of the title compound as a clear oil; MS(EI) m/e 457 (M+). ¹H NMR (CDCl₃, 300 MHz) δ0.68 (m, 6H), 1.35–1.73 (m, 12H), 2.25 (m, 3H), 3.05 (m, 3H), 3.58 (m, 3H), 4.52–4.82 (m, 1H), 5.23–5.38 (m, 1H), 7.05 (m, 3H), 7.32 (m, 1H), 7.61 (t, 1H), 8.06 (m, 1H).

6c: 2(S)-[3-(BOCamino)-3-(1H-indol-3-ylmethyl)-2-oxo-1-pyrrolidinyl]-4-methylpentanoic acid]

To a solution of Example 6b (0.46 g, 0.10 mmol) in methanol (5 mL) cooled to 0° C. was added 0.5N NaOH (2.1 mL). The solution was stirred at 0° C. for 18 hours, acidified to pH 3–4 with solid citric acid, and extracted with ethyl acetate (3×). After drying with Na₂SO₄ the solvent was removed in vacuo to yield 0.40 g of the title compound as a clear oil; MS(EI) m/e 443 (M+).

6d: {2(S)-[3-(BOCamino)-3-(indol-3-ylmethyl)-2-oxo-1-pyrrolidinyl]-4-methylpentanoyl}-Asp(OBn)-Phe-NH$_2$ To a solution of Example 6c (0.34, 0.78 mmol) and N-methylmorpholine (NMM) (0.08 g, 0.78 mmol) in THF (5 mL) at 0° C. was added isobutyl chloroformate (0.107 g, 0.78 mmol). After 10 minutes a cold (0° C.) solution of Asp(OBn)-Phe-NH$_2$ trifluoroacetate (0.38 g, 0.78 mmol) and NMM (0.08 g, 0.78 mmol) in DMF (5 mL) was added. The reaction was warmed to 0° C. and stirred for 1 hour. Ethyl acetate (30 mL) was added and the organics washed with aqueous solutions of 0.1N HCl (3×) and saturated NaHCO$_3$ (3×). After drying over anhydrous sodium sulfate, the solvent was removed in vacuo to yield 0.58 g of the title compound as a waxy solid; MS(CI/NH$_3$) m/e 795 (M+H)+.

6e: {2(S)-[3-(BOCamino)-3-(indol-3-yl methyl)-2-oxo-1-pyrrolidinyl]-4-methylpentanoyl}-Asp-Phe-NH$_2$ A mixture of Example 6d (0.58 g, 0.73 mmol) and 5% Pd/BaSO$_4$ in methanol (15 mL) was hydrogenated under one atmosphere hydrogen at ambient temperature overnight. The catalyst was filtered and the solvent removed in vacuo. The residue was chromatographed on silica gel using ethyl acetate/pyridine/acetic acid/water (31.4/4.0/1.2/2.2) to yield 0.14 g of a more mobile diastereomer (isomer A) of the title compound and 0.12 g of a less mobile diastereomer (isomer B) of the title compound. Isomer A: MS(CI/NH$_3$) m/e 705 (M+H)+. 1H NMR(DMSO-d$_6$, 300 MHz) δ0.38 (dd, 6H), 0.72 (m, 1H), 1.30 (m, 11H), 2.17 (m, 2H), 2.38 (m, 1H), 2.50 (m, 2H), 2.72 (m, 5H), 4.28 (m, 2H), 4.46 (m, 1H), 6.93 (t, 1H), 7.04 (t, 1H), 7.10 (m, 4H), 7.21 (m, 5H), 7.51 (m, 3H), 7.92 (d, 1H), 10.98 (br s, 1H), 12.12 (br s, 1H). Anal calc for C$_{37}$H$_{48}$N$_6$O$_8$.H$_2$O: C 61.46, H 6.97, N 11.63; Found: C 61.70, H 6.81, N 11.52. Isomer B: MS(CI/NH$_3$) m/e 705 (M+H)+. 1H NMR(DMSO, 300 MHz) δ0.75 (m, 7H), 1.30–1.62 (m, 11H), 2.0 (m, 2H), 2.40–3.75 (m, 8H), 4.31 (m, 1H), 4.45 (m, 2H), 6.68 (br s, 1H), 6.94 (t, 1H), 7.10 (m, 8H), 7.31 (m, 2H), 7.48 (d, 1H), 7.79 (m, 1H), 8.22 (m, 1H), 10.85 (br s, 1H), 12.30 (br s, 1H), Anal calc for C$_{37}$H$_{48}$N$_6$O$_8$.H$_2$O: C 61.46, H 6.97, N 11.63; Found: C 61.30, H 6.90, N 11.12.

EXAMPLE 7

(2H-2-aza-benzo[cd]azulene-8-carboxyl)-Leu-Asp-Phe-NH$_2$

7a: 4-(1-Acetyl-indol-4-yl)-but-2-enoic acid methyl ester

To a solution of 1-acetyl-indole-4-acetaldehyde (2.40 g, 11.93 mmol) prepared according to the method of H. Plieninger, et. al., Chem.Ber., 1956, 89:270 in THF (100 mL) was added methyl(triphenylphos-phoranylidene)acetate (4.78 g, 14.3 mmol). The solution was stirred at ambient temperature overnight. The solvent was removed in vacuo and the residue chromatographed (eluting with ethyl acetate/hexanes). Recrystallization from ethyl acetate/hexanes resulted in 2.12 g of the title compound as a white solid in two crops; MS(CI/NH$_3$) m/e 258 (M+H)+. 1H NMR (CDCl$_3$, 300 MHz) δ2.60 (s, 3H), 3.70 (s, 3H), 3.75 (dd, 2H), 3.75 (m, 1H), 6.63 (dd, 1H), 7.05 (d, 1H), 7.12–7.22 (m, 2H), 7.29 (t, 1H), 7.43 (d, 1H), 8.35 (d, 1H).

7b: 4-(Indol-4-yl)-but-2-enoic acid methyl ester

To a solution of Example 7a (1.0 g, 3.89 mmol) in methanol (60 mL) at ambient temperature was added magnesium ethoxide (1.0 g, 8.73 mmol). The reaction was stirred vigorously for 10 minutes and poured into 0.1N HCl (100 mL). The aqueous layer was extracted with ethyl acetate (3×) and the organic layer washed with saturated brine (3×). After drying over anhydrous sodium sulfate, the solvent was removed in vacuo to yield 0.81 g of the title compound as a greenish oil; MS(EI) m/e 215 (M+).

7c: 4-(3-Formylindol-4-yl)-but-2-enoic acid methyl ester

Phosphorous oxychloride (0.65 g, 4.16 mmol) was added dropwise to DMF (3 mL) at 0° C. After 0.5 hour, Example 7b (0.81 g, 3.70 mmol) in DMF (3 mL) was added at 0° C., then the mixture warmed to 35° C. for 0.75 hour. The solution was cooled to ambient temperature and crushed ice (10 g) was added. Solid sodium bicarbonate was added and to pH 8, the mixture diluted with water (100 mL), and the aqueous extracted with ethyl acetate (3×). The organic phase was separated, dried over anhydrous sodium sulfate, and the solvent removed in vacuo. The residue was chromatographed (eluting ethyl acetate/hexanes) to yield 0.39 g of the title compound as a purple solid; MS(CI/NH$_3$) m/e 244 (M+H)+. 1H NMR(CDCl$_3$, 300 MHz) δ3.68 (s, 3H), 4.26 (m, 2H), 5.14 (m, 1H), 7.06 (d, 1H), 7.18 (m, 3H), 7.84 (d, 1H), 9.09 (br s, 1H), 9.88 (s, 1H).

7d: 8-Methoxycarbonyl-2H-2-aza-benzo[cd]azulene

To a solution of Example 7c (0.34 g, 1.38 mmol) in benzene (10 mL) was added DBU (0.25 g, 1.65 g) and the mixture refluxed overnight. After cooling to ambient temperature the mixture was poured into 0.1N HCl (100 mL) and extracted with ethyl acetate (3×). After drying over anhydrous sodium sulfate, the solvent was removed in vacuo to yield 0.29 g of the title compound as a purple solid; MS (CI/NH$_3$) m/e 225 (M+). 1H NMR (CDCl$_3$, 300 MHz) δ3.70 (s, 3H), 5.65 (d, 1H), 5.85 (dd, 1H), 6.11 (dd, 1H), 6.64 (m, 3H), 7.08 (br s, 1H), 7.78 (br s, 1H).

7e: 2H-2-aza-benzo[cd]azulene-8-carboxylic acid

To a solution of Example 7d (0.10 g, 0.44 mmol) in methanol (5 mL) at ambient temperature was added 0.05N KOH (10.67 mL). The solution was refluxed overnight and then poured into ethyl acetate (100 mL) and water (100 mL). The aqueous phase was separated, acidified to pH 3–4 with aqueous 10% sulfuric acid, and extracted with ethyl acetate (3×). After drying over anhydrous sodium sulfate, the solvent was removed in vacuo to yield 0.086 g of the title compound as a purple solid; MS(EI) m/e 211 (M+).

7f: (2H-2-aza-benzo[cd]azulene-8-carboxyl)-Leu-Asp-Phe-NH$_2$

To a solution of Example 7e (0.05 g, 0.23 mmol) in THF (3 mL) at −20° C. were added N-methylmorpholine (0.024 g, 0.23 mmol) and isobutyl chloroformate (0.033 g, 0.23 mmol). After 10 minutes the reaction was warmed to 0° C. and Leu-Asp-Phe-NH$_2$ (0.097 g, 0.23 mmol) in cold (0° C.) DMF/H$_2$O (80:20 v/v, 3 mL) was added dropwise. The reaction was stirred overnight with warming to ambient temperature. The mixture was poured into water (50 mL) and extracted with ethyl acetate (3×). After drying over anhydrous sodium sulfate, the solvent was removed in vacuo and the residue chromatographed on silica gel eluting with ethyl acetate/pyridine/acetic acid/water (31.4/4.0/.1.2/2.2) to yield 0.018 g of the title compound as an off-white solid; MS(Cl/NH$_3$) m/e 586 (M+H)+. 1H NMR (DMSO-d$_6$, 300 MHz) δ0.80 (m, 6H), 1.30 (m, 1H), 1.49 (m, 1H), 2.40 (m, 1H), 2.59 (m, 1H), 2.78 (m, 1H), 2.98 (m, 1H), 4.17 (m, 1H), 4.29 (m, 1H), 4.42 (m, 1H), 5.48

(m, 2H), 5.95 (d, 1H), 6.51 (m, 3H), 6.84 (s, 1H), 7.16 (m, 7H), 7.78 (m, 2H), 8.16 (m, 1H), 10.88 (br s, 1H).

EXAMPLE 8

D-Ctp-Leu-Asp-Phe-NH$_2$

8a: Bromoactetyl-D-Trp-OBn

To a solution of D-Trp-OBn hydrochloride (9.30 g, 28.11 mmol) and triethylamine (6.11 g, 60.40 mmol) in absolute ethanol (200 mL) cooled to 0° C. was added bromoacetyl chloride (5.31 g, 33.70 mmol) dropwise over 10 minutes. The reaction mixture was stirred overnight with warming to ambient temperature. The solvent was removed in vacuo and the residue partitioned between aqueous 0.1N HCl (250 mL) and ethyl acetate (250 mL). After drying over anhydrous sodium sulfate, the organic layer was concentrated in vacuo and the residue chromatographed (eluting with ethyl acetate/-hexanes) to yield 4.60 g of the title compound as a clear colorless oil.

8b: D-Ctp-OBn

A solution of Example 8a (4.0 g, 9.66 mmol) in 40% ethanol/water (1 L) at 80° C. was irratiated (Hanovia 450 W. Hg lamp/vycor filter) for 3 hours. The resulting mixture was concentrated in vacuo to 600 mL and the aqueous layer extracted with ethyl acetate (3×). After drying over anhydrous sodium sulfate, the solvent was removed in vacuo and the residue chromatographed (ethyl acetate) to yield a mixture of 2- and 4-substituted cyclized products. The mixture was recrystallized (ethyl acetate/diethyl ether/hexanes) to yield 0.0.12 g of the title compound as a white crystalline solid. $^1$H NMR (DMSO-d$_6$, 300 MHz) δ3.42 (m, 3H), 4.10 (br d, 1H), 4.30 (br s, 1H), 5.25 (s, 2H), 6.75 (d, 1H), 6.94 (t, 1H), 7.12 (m, 3H), 7.30 (m, 5H).

8c: D-Ctp-Leu-Asp(OBn)-Phe-NH$_2$

A mixture of Example 8b (10 g, 0.29 mmol) and 5% Pd/BaSO$_4$ (0.02 g) in methanol (10 mL) was hydrogenated under one atmosphere of hydrogen at ambient temperature for 0.5 hour. The catalyst was filtered and the solvent removed in vacuo to yield 0.063 g of free acid (D-Ctp-OH) as a pink solid sufficient for use without further purification. To the acid (0.063 g, 0.26 mmol) in DMF (5 mL) cooled to 0° C. were added Leu-Asp(OBn)-Phe-NH$_2$ hydrochloride (0.13 g, 0.26 mmol), diphenyl phosphoryl azide (0.085 g, 0.30 mmol) (DPPA), and N-methyl morpholine (0.057 g, 0.56 mmol). The mixture was stirred overnight with warming to ambient temperature. The solvent was concentrated to 2 mL and the residue dissolved in ethyl acetate (50 mL). The organic layer was washed with aqueous solutions of saturated NaHCO$_3$ (3×) and 0.1N HCl (3×). After drying over anhydrous sodium sulfate, the solvent was removed in vacuo. The residue was triturated from ethyl acetate/hexanes to yield 0.07 g white solid; MS(FAB+) m/e 709 (M+H)+. $^1$H NMR (DMSO-d$_6$, 300 MHz) δ0.90 (m, 6H), 1.35–1.70 (m, 3H), 2.55 (m, 1H), 2.78 (m, 2H), 2.95 (m, 1H), 3.10–3.55 (m, 2H), 4.10–4.65 (m, 6H), 5.09 (s, 2H), 6.75 (d, 1H), 6.73 (m, 2H), 7.14 (m, 14H), 7.83 (d, 1H), 8.31 (d, 1H), 8.43 (d, 1H), 10.93 (br s, 1H).

8c: D-Ctp-Leu-Asp-Phe-NH$_2$

A mixture of Example 8c (0.04 g, 0.056 mol) and 5% Pd/BaSO$_4$ (0.01 g) in acetic acid (5 mL) was hydrogenated under one atmosphere hydrogen at ambient temperature overnight. The reaction mixture was filtered twice through Celite® filter aid and the solvent removed in vacuo. The residue was suspended in water (1 mL) and lyopholized to yield 0.028 g of the title compound; MS (FAB+) m/e 619 (M+H)+. $^1$H NMR (DMSO-d$_6$, 300 MHz) δ0.78 (m, 6H), 1.30 (m, 2H), 1.55 (m, 1H), 2.35–3.60 (m, 7H), 4.15 (m, 2H), 4.33 (m, 2H), 4.49 (m, 1H), 6.75 (d, 1H), 6.92 (m, 2H), 7.11 (m, 12H), 7.84 (d, 1H), 8.28 (d, 1H), 8.36 (d, 1H), 10.90 (br s, 1H), 12.35 (br s, 1H).

EXAMPLE 9

2-Naphthoyl-(dehydro)Phe-Leu-Asp-Phe-NH$_2$

9a: 2-Naphthoic acid N-hydroxysuccinimide ester

To a solution of 2-naphthoic acid (2 g, 11.62 mmol) and N-hydroxysuccinimide (1.34 g, 11.62 mmol) in 75 mL of a 2:1 v/v mixture of ethyl acetate-1,2-dimethoxyethane (glyme) which was chilled in an ice bath was added DCC (2.4 g, 11.62 mmol) in one portion. The flask was capped with a drierite filled drying tube and allowed to stir overnight while slowly warming to ambient temperature. The reaction mixture was subsequently filtered and the filtrate concentrated in vacuo. The residue was recrystallized from ethyl acetate-hexane to yield 2.73 g (two crops) of the title compound as white crystals. $^1$H NMR (CDCl$_3$, 300 MHz) δ2.95 (s, 4H), 7.5–7.75 (m, 2H), 7.85–8.2 (m, 4H), 8.76 (s, 1H). Anal calc for C$_{15}$H$_{11}$NO$_4$: C, 66.90; H, 4.12; N, 5.20. Found: C, 66.87; H, 4.13; N, 5.17.

9b: 2-(2-Naphthyl)-4-benzylidene-5(4H)-oxazolone

The product from Example 9a (1.07 g, 3.98 mmol) was combined with glycine methyl ester hydrochloride (0.55 g, 4.38 mmol) in dimethylformamide (DMF) (10 mL) and the resulting solution cooled in an ice bath. To the cold solution was added DIEA (0.76 mL, 4.4 mmol) followed by removal of the ice bath. The flask was capped with a drierite filled drying tube and allowed to stir overnight. The reaction mixture was subsequently partitioned between ethyl acetate and water. The organic phase was washed with 10% HCl, water, dried with magnesium sulfate, filtered and concentrated in vacuo to give 0.91 g of solid crude product sufficient for use without further purification. The ester (0.91 g, 3.74 mmol) was dissolved in methanol (25 mL) and treated at ambient temperature with potassium hydroxide (0.7 g, 12 mmol) in water (10 mL). After one hour, the reaction mixture was partitioned between ethyl acetate and dilute aqueous HCl. The organic phase was washed once with water, dried with magnesium sulfate, filtered and concentrated in vacuo to give 0.74 g of the crude product as a white solid sufficient for use without further purification. The acid (0.74 g, 3.23 mmol) was suspended in acetic anhydride (30 mL) to which was added sodium acetate trihydrate (1.3 g, 9.81 mmol) and benzaldehyde (0.33 mL, 3.27 mmol). The flask was capped with a water cooled condenser/drierite filled drying tube and the mixture heated on a steam bath for one hour. The reaction mixture was subsequently concentrated in vacuo and the residue partitioned between water and ethyl acetate. The organic phase was washed with 5% sodium bicarbonate solution, water, dried over magnesium sulfate, filtered and concentrated in vacuo. The crude product was recrystallized from ethyl acetate-hexane to give 0.34 g of the title compound as a bright yellow solid. An additional 0.09 g of the product was obtained from the mother liquor by flash chromatography on silica gel (eluting with ethyl acetate-hexane). $^1$H NMR (DMSO-d$_6$, 300 MHz) δ7.6 (s, 1H), 7.5–7.8 (m, 5H), 8.0–8.4 (m, 6H), 8.75 (s, 1H). Anal calc for C$_{20}$H$_{13}$NO$_2$: C, 80.24; H, 4.39; N, 4.68. Found: C, 80.43; H, 4.51; N, 4.35. mp 164°–168.5° C.

9c: 2-Naphthoyl-(dehydro)Phe-Leu-Asp-Phe-NH$_2$

The azalactone from Example 9b (0.336 g, 1.12 mmol) was combined with Leu-Asp-Phe-NH$_2$, prepared according to Kenner, G. W., et al., *J. Chem. Soc.* (C), 1968, 761 (0.44 g, 1.12 mmol) in DMF (15 mL) containing a catalytic amount of p-dimethylaminopyridine (DMAP) followed by the addition of DIEA (0.2 mL, 1.23 mmol) and heating, under nitrogen, to 55°–60° C. After 2.5 hours the reaction mixture was partitioned between ethyl acetate and dilute aqueous HCl. The organic phase was washed once with water, dried (magnesium sulfate), filtered and concentrated in vacuo. The crude product was recrystallized from aqueous ethanol to give 0.637 g of the title compound as a white crystalline solid, mp 212.5°–214° C. (dec). MS(FAB+) m/e 692 (M+H)+. $^1$H NMR (DMSO-d$_6$, 300 MHz) δ0.9 (d, J=6 Hz, 6H), 1.4–1.8 (m, 3H), 2.55–3.1 (m, 4H), 4.2–4.6 (m, 3H), 7.0–7.24 (m, 8H), 7.26–7.45 (m, 3H), 7.6–7.75 (m, 5H), 8.0–8.16 (m, 4H), 8.2 (d, J=7.5 Hz, 1H), 8.5 (d, J=7.5 Hz, 1H), 8.7 (s, 1H), 10.45 (s, 1H), 12.47 (br s, 1H). Anal calc for C$_{39}$H$_{41}$N$_5$O$_7$·0.5H$_2$O: C, 66.83; H, 6.05; N, 9.99. Found: C, 66.77; H, 6.02; N, 9.86.

EXAMPLE 10

1-Naphthoyl-(dehydro)Phe-Leu-Asp-Phe-NH$_2$

10a: 1-Naphthoic acid N-hydroxysuccinimide ester

The ester was prepared by coupling 1-naphthoic acid (2 g, 11.62 mmol) with N-hydroxysuccinimide (1.34 g, 11.62 mmol) as outlined in Example 9a to yield 2.57 g the title compound as a white crystalline solid. $^1$H NMR (CDCl$_3$, 300 MHz) δ2.95 (br s, 4H), 7.5–7.8 (m, 3H), 7.93 (d, J=9 Hz, 1H), 8.6 (d, J=7.5 Hz, 1H), 8.46 (dd, J=7.5 Hz, 1.5 Hz, 1H), 8.81 (d, J=9 Hz, 1H). Anal calc for C$_{15}$H$_{11}$NO$_4$: C 66.90, H 4.12, N 5.20. Found: C 66.77, H 4.22, N 5.33.

10b: 2-(1-Naphthyl)-4-benzylidene-5(4H)-oxazolone

The product from Example 10a (1.07 g, 3.98 mmol) was reacted with glycine methyl ester hydrochloride (0.55 g, 4.38 mmol) as in Example 9b to yield a crude product, 1.0 g, which was subsequently treated with potassium hydroxide (0.7 g, 12 mmol) in methanol (25 mL) as in Example 9b to give 0.75 g of the corresponding acid as a white crystalline solid. The azalactone was prepared by condensing the above acid (0.75 g, 3,27 mmol) with benzaldehyde (0.33 mL, 3.27 mmol) in the presence of sodium acetate trihydrate (1.38 g, 9.81 mmol) as in Example 9b to yield after flash chromatography on silica gel (eluting with ethyl acetate-hexane) 0.346 g of the title compound as a yellow crystalline solid, mp 134°–137° C. $^1$H NMR (DMSO-d$_6$, 300 MHz) δ7.45 (s, 1H), 7.5–7.65 (m, 3H), 7.65–7.8 (m, 2H), 7.8–7.9 (t, 1H), 8.14 (d, J=7.5 Hz, 1H), 8.25–8.4 (m, 2H), 9.4 (d, J=9.0 Hz, 1H). Anal calc for C$_{20}$H$_{13}$NO$_2$: C, 80.24; H, 4.39; N, 4.68. Found: C, 80.29; H, 4.48; N, 4.55.

10c: 1-Naphthoyl-(dehydro)Phe-Leu-Asp-Phe-NH$_2$

The azalactone from Example 10b (0.18 g, 0.60 mmol) was condensed with Leu-Asp-Phe-NH$_2$ (0.24 g, 0.60 mmol) as in Example 9c to give 0.272 g of a crystalline product. MS (FAB+) m/e 692 (M+H)+, m/e 714 (M+Na)+. $^1$H NMR (DMSO-d$_6$, 300 MHz) δ0.92 (m, 6H), 1.4–1.88 (m, 3H), 2.45–3.1 (m, 4H), 4.26–4.6 (m, 3H), 7.04–7.29 (m, 8H), 7.3–7.49 (m, 3H), 7.5–7.7 (m, 5H), 7.78–7.9 (t, 2H), 8.0 (d, J=7.5 Hz, 1H), 8.08 (d, J=9 Hz, 1H), 8.24–8.4 (m, 3H), 10.3 (s, 1H), 12.4 (br s, 1H). Anal calc for C$_{39}$H$_{41}$N$_5$O$_7$: C, 67.70; H, 5.98; N, 10.12. Found: C, 67.57; H, 6.05; N, 10.02.

EXAMPLE 11

BOC-Trp-Leu-Asp-(dehydro)Phe-NH$_2$

11a: Azalactone of BOC-Asp(O-t-Butyl)-β-Phenylserine

To a solution of BOC-(β-O-t-butyl)aspartic acid (0.34 g, 1.17 mmol) in THF (20 mL) under a nitrogen atmosphere was added NMM (0.13 mL, 1.17 mmol). The mixture was cooled to −10° C./−15° C. and isobutylchloroformate (IBCF) (0.15 mL, 1.17 mmol) added in one portion via syringe. After 7 minutes at low temperature, the resulting suspension was warmed to 0° C./+5° C. and a previously prepared suspension of β-phenylserine hydrate (0.21 g, 1.17 mmol) in a total of 6 mL of water containing NMM (0.13 mL, 1.17 mmol) added dropwise over 2 minutes. The resulting clear solution was allowed to stir while slowly warming to room temperature. The reaction was quenched by pouring into 10% citric acid solution and the crude product recovered by extraction with ethyl acetate, dried (magnesium sulfate), filtered and concentrated in vacuo. Purification by flash chromatography on silica gel eluting with (ethyl acetate/hexane/acetic acid) then (ethyl acetate/acetone/acetic acid) gave a foam (0.29 g). This material was subsequently dissolved in acetic anhydride and sodium acetate trihydrate (0.26 g, 1.91 mmol) was added. The flask was capped with a drierite filled drying tube and the mixture stirred at ambient temperature for 6 hours. The reaction mixture was concentrated in vacuo to dryness then partitioned between chloroform and 10% citric acid solution. The aqueous phase was extracted twice with chloroform. The combined extracts were dried (magnesium sulfate), filtered and concentrated in vacuo. The crude product was purified by flash chromatography on silica gel (eluting with ethyl acetate-hexane) to give 0.221 g of the pure azalactone as a foam. $^1$H NMR (DMSO-d$_6$, 300 MHz) δ1.4 (s, 18H), 2.65–3.0 (m, 2H), 4.92 (q, 1H), 7.36 (s, 1H), 7.45–7.55 (m, 3H), 7.6 (d, J=9 Hz, 1H), 8.2 (m, 2H).

11b: BOC-Asp(O-t-butyl)-(dehydro)Phe-NH$_2$

The product from Example 11a (0.029 g, 0.071 mmol) was dissolved in dioxane (2.5 mL) and treated at ambient temperature with concentrated ammonium hydroxide solution (2.5 mL). After 30 minutes the reaction was quenched by pouring into 10% citric acid solution. The crude product was recovered by extraction with chloroform, dried (magnesium sulfate), filtered and concentrated in vacuo. Purification by preparative thin-layer chromatography (silica gel-GF/1 mm, ethyl acetate) gave the pure product (0.015 g). $^1$H NMR (DMSO-d$_6$, 300 MHz) δ1.4 (s, 18H), 2.4–2.8 (m, 2H), 4.36 (q, 1H), 7.22 (s, 1H), 7.26–7.4 (m, 5H), 7.57 (m, 2H), 9.55 (s, 1H).

11c: BOC-Leu-Asp-(dehydro)Phe-NH$_2$

The dipeptide amide as prepared in Example 11b (0.127 g, 0.293 mmol) was treated with 5 mL of 1.5N HCl in glacial acetic acid. After one hour the reaction mixture was frozen and lyophilized to give in quantitative yield the fully deprotected dipeptide amide as the hydrochloride salt. This material (0.092 g, 0.293 mmol) was subsequently combined with BOC-Leu-OSu (0.098 g, 0.29 mmol) in DMF (5 mL) solution in an ice bath and treated with DIEA (0.11 mL, 0.645 mmol). The flask was capped with a drierite filled drying tube and allowed to stir overnight while slowly warming to room temperature. The reaction was quenched by pouring into aqueous citric acid and the crude product isolated by extraction with ethyl acetate followed by drying (magnesium sulfate), filtration and concentration in vacuo. Recrystallization from ethyl acetate gave 0.091 g of the pure title compound, mp 178.5°–180.5° C. (d); $^1$H NMR (DMSO-d$_6$, 300 MHz) δ0.85 (t, 6H), 1.34 (s, 9H), 1.3–1.7 (m, 3H), 2.55–2.9 (m, 2H), 3.96 (m, 1H), 4.57 (m, 1H), 7.08 (d, J=6 Hz, 1H), 7.15 (br s, 1H), 7.25–7.45 (m, 5H), 7.55 (d, J=7.5 Hz, 1H), 8.47 (d, J=6 Hz, 1H), 9.35 (s, 1H), 12.55 (br s, 1H). Anal calc for $C_{24}H_{34}N_4O_7 \cdot 0.5$-H$_2$O: C, 57.69; H, 7.07; N, 11.22. Found: C, 57.86; H, 6.71; N, 11.08.

11d: BOC-Trp-Leu-Asp-(dehydro)Phe-NH$_2$

The product from Example 11c (0.084 g, 0.171 mmol) was treated with 5 mL 1.5N HCl in glacial acetic acid at room temperature. After one hour the reaction mixture was frozen and lyophilized to give in quantitative yield the deprotected tripeptide amide as the hydrochloride salt. This material (0.073 g, 0.171 mmol) was subsequently combined with BOC-Trp-OSu (0.069 g, 0.171 mmol) in DMF solution (2 mL) in an ice bath and treated with DIEA (0.066 mL, 0.376 mmol). The flask was capped with a drierite filled drying tube and allowed to stir overnight while slowly warming to ambient temperature. The reaction was quenched by pouring into ice cold aqueous citric acid and the crude product isolated by vacuum filtration. Recrystallization from aqueous ethanol gave 0.065 g of pure peptide, mp 192°–194° C. (dec). MS (FAB+) m/e 677 (M+H)$^+$. $^1$H NMR (DMSO-d$_6$, 300 MHz) δ0.85 (m, 6H), 1.15 and 1.3 (s, 9H total), 1.4–1.75 (m, 3H), 2.5–3.2 (m, 4H), 4.2 (m, 1H), 4.4 (m, 1H), 4.6 (m, 1H), 6.86 (d, J=7.5 Hz, 1H), 6.97 (t, 1H), 7.06 (t, 1H), 7.12 (s, 1H), 7.17 (s, 1H), 7.27 (s, 1H), 7.27–7.45 (m, 5H), 7.55–7.65 (m, 3H), 8.0 (d, J=7.5 Hz, 1H), 8.52 (d, J=7.5 Hz, 1H), 9.54 (s, 1H), 10.78 (s, 1H), 12.6 (br s, 1H). Anal calc for $C_{35}H_{44}N_6O_8 \cdot H_2O$: C, 60.49; H, 6.69; N, 12.08. Found: C, 60.16; H, 6.26; N, 11.74.

EXAMPLE 12

BOC-Trp-Leu-Asp-(m-nitro)Phe-NH$_2$

12a: N-Acetylamino-(m-nitro)benzyl-diethylmalonate

To a solution of freshly prepared sodium ethoxide (0.1 g, 4.3 mmol sodium, 25 mL absolute ethanol) under nitrogen at ambient temperature was added solid N-acetylamino diethylmalonate (1 g, 4.60 mmol). After 25 minutes solid m-nitro-benzylbromide (1 g, 4.60 mmol) was added and the resulting mixture heated at reflux overnight. The reaction mixture was partitioned between ethyl acetate and 10% citric acid solution. The organic phase was washed once with water, dried (magnesium sulfate), filtered and concentrated in vacuo. Purification by flash chromatography on silica gel eluting with ethyl acetate-hexane gave 0.58 g of the title compound as a solid, mp 156°–157° C. $^1$H NMR (DMSO-d$_6$, 300 MHz) δ1.18 (t, 6H), 1.95 (s, 3H), 3.58 (s, 2H), 4.17 (m, 4H), 7.46 (d, J=7.5 Hz, 1H), 7.61 (t, 1H), 7.8 (s, 1H), 8.15 (d, 1H), 8.23 (s, 1H). Anal calc for $C_{16}H_{20}N_2O_7$: C, 54.53; H, 5.73; N, 7.95. Found: C, 54.35; H, 5.65; N, 7.80.

12b: BOC-(m-nitro)Phe

The product from Example 12a (0.061 g, 0.172 mmol) was suspended in 6N HCl (6 mL) and refluxed for 4 hours. The reaction mixture was concentrated in vacuo, diluted with 1:1 v/v dioxane-water and made basic with sodium hydroxide. To this was added excess di-t-butyl dicarbonate and the mixture allowed to stir overnight at ambient temperature. The reaction mixture was diluted with 10% citric acid solution and the crude product isolated by extraction with ethyl acetate, followed by drying (magnesium sulfate), filtration and concentration in vacuo. Purification by preparative tlc gave 0.038 g of the title compound as an amber colored glass, mp 117.7°–118.5° C. $^1$H NMR (DMSO-d$_6$, 300 MHz) δ1.28 (s, 9H), 2.85–3.3 (m, 2H), 4.15 (m, 1H), 7.18 (d, J=9 Hz, 1H), 7.6 (t, 1H), 7.75 (d, J=7.5 Hz, 1H), 8.1 (d, J=9 Hz, 1H), 8.15 (s, 1H). Anal calc for $C_{14}H_{18}N_2O_6$: C, 54.18; H, 5.86; N, 9.03. Found: C, 54.25; H, 5.70; N, 8.59.

12c: BOC-(m-nitro)Phe-NH$_2$

The product from Example 12b (1.7 g, 5.48 mmol) was dissolved in THF (50 mL) and treated with NMM (0.58 mL, 5.30 mmol). The resulting solution was cooled in an ice bath under a nitrogen atmosphere and to this cold solution was added ethyl chloroformate (0.46 mL, 4.82 mmol). After 10 minutes. The flask was subsequently capped with a drierite filled drying tube and allowed to slowly warm to room temperature. The crude product was isolated by concentration of the reaction mixture in vacuo, dilution with water and vacuum filtration. The solid product was dried in vacuo at room temperature. The product was purified by recrystallization from ethyl acetate-hexane, mp 189°–191.5° C. (dec); $^1$H NMR (DMSO-d$_6$, 300 MHz) δ1.25 (s, 9H), 2.75–3.2 (m, 2H), 4.14 (m, 1H), 6.48 (d, J=9 Hz, 1H), 7.1 (s, 1H), 7.48 (s, 1H), 7.59 (t, 1H), 7.75 (d, J=7.5 Hz, 1H), 8.08 (d, J=7.5 Hz, 1H), 8.2 (s, 1H). Anal calc for $C_{14}H_{19}N_3O_5$: C 54.35, H 6.20, N 13.59; found: C 54.35, H 6.24, N 13.51.

12d: BOC-Asp(O-t-butyl)-(m-nitro)Phe-NH$_2$

The product from Example 12c (0.98 g, 3.18 mmol) was treated with 16 mL of 1.5N HCl in glacial acetic acid at room temperature. After 45 minutes anhydrous ether (100 mL) was added dropwise with vigorous stirring. The hydrochloride was collected by vacuum filtration to yield after drying in vacuo at room temperature 0.77 g of a white solid sufficiently pure for use as isolated. To a solution of BOC-Asp(β-t-butyl) ester (0.92 g, 3.18 mmol) in THF (50 mL) under nitrogen at room temperature was added NMM (0.35 mL, 3.18 mmol) and the resulting solution cooled to $-10°$ C. Isobutyl chloroformate (IBCF) (0.41 mL, 3.18 mmol) was added in two portions and the activation allowed to proceed 6 minutes before a previously prepared slurry of the above hydrochloride (0.77 g, 3.13 mmol) in a DMF (16 mL)/DMSO (0.25 mL) mixture containing NMM (0.35 mL, 3.18 mmol) was added dropwise over 2 minutes. The reaction mixture was subsequently warmed to 0°/+5° C. and allowed to stir approximately 2.5 hours. The reaction was quenched by pouring into a mixture of ethyl acetate, 10% citric acid and water. The organic phase was washed once with 10% citric acid, twice with 5% sodium bicarbonate solution and once with water, then dried (magnesium sulfate), filtered and concentrated in vacuo to yield the crude product as a pink glass. Purification by recrystallization from ethyl acetate-hexane gave 0.57 g (two crops) of a solid product. It became clear from the NMR analysis that one diastereomer was recovered by recrystallization. HPLC analysis (C$_{18}$ reverse phase, acetonitrile-50 mmol ammonium acetate, pH 4.5) of the recrystallized product as well as the material recovered from the mother liquor after each had been deprotected by treatment with HCl in glacial acetic acid under standard conditions showed that the former was the long retention time component (isomer A) of the mixture. The material recovered from the mother liquor was rich in the short retention time component (isomer B). The analytical sample was obtained by flash chromatography on silica gel (eluting with ethyl acetate-hexane) of the material recovered from the mother liquor. $^1$H NMR (DMSO-$d_6$, 300 MHz) isomer A δ1.35 (d, 18H), 2.2–2.55 (m, 2H), 2.85–3.25 (m, 2H), 4.2 (m, 1H), 4.5 (m, 1H), 7.08 (d, J=9 Hz, 1H), 7.25 (br s, 1H), 7.55 (m, 2H), 7.67 (d, J=7.5 Hz, 1H) 7.83 (d, J=7.5 Hz, 1H), 8.0–8.2 (m, 2H). Anal calc for $C_{22}H_{32}N_4O_8$: C, 54.98; H, 6.72; N, 11.66. Found: C, 54.76; H, 6.86; N, 11.30.

12e: BOC-Leu-Asp-(m-nitro)Phe-NH$_2$ (Isomer A)

Isomer A from Example 12d (0.46 g, 0.95 mmol) was treated with excess 1.5N HCl in glacial acetic acid at ambient temperature. The flask was capped with a drierite filled drying tube and allowed to stir 5 hours. The reaction mixture was subsequently frozen and lyophilized. The crude hydrochloride was used without further purification. The hydrochloride (0.95 mmol) was combined with BOC-Leu-OSu (0.31 g, 0.95 mmol) in a flask chilled in an ice bath to which was added prechilled DMF (15 mL) followed by DIEA (0.36 mL, 2.09 mmol). The flask was capped with a drierite filled drying tube and allowed to stir overnight while slowly warming to room temperature. The reaction mixture was subsequently concentrated in vacuo and poured into dilute aqueous citric acid solution. The crude product was collected by vacuum filtration and water washed. Purification by recrystallization from aqueous ethanol gave 0.32 g of the title compound as a solid product (two crops). $^1$H NMR (DMSO-$d_6$, 300 MHz) δ0.83 (m, 6H), 1.2–1.65 (m, 3H), 1.37 (s, 9H), 2.4–2.7 (m, 2H), 2.85–3.25 (m, 2H) 3.92 (m, 1H), 4.45 (m, 2H), 6.83 (d, J=9 Hz, 1H), 7.25 (s, 1H), 7.38 (s, 1H), 7.55 (t, 1H), 7.67 (d, J=7.5 Hz, 1H), 7.95–8.2 (m, 3H). Anal calc for $C_{24}H_{35}N_5O_9$: C, 53.61; H, 6.57; N, 13.03. Found: C, 53.44; H, 6.61; N, 12.97.

12f: BOC-Trp-Leu-Asp-(m-nitro)Phe-NH$_2$ (Isomer A)

The product from Example 12e (0.259 g, 0.48 mmol) was treated with 7 mL of 1.5N HCl in glacial acetic acid at ambient temperature. The flask was capped with a drierite filled drying tube and allowed to stir for one hour. The reaction mixture was subsequently frozen and lyophilized. The crude hydrochloride was used without further purification. The hydrochloride (0.48 mmol) was combined with BOC-Trp-OSu (0.2 g, 0.48 mmol) in a flask to which was added DMF and the resulting solution chilled in an ice bath. To the cold solution was added DIEA (0.184 mL, 1.06 mmol) and the flask capped with a drierite filled drying tube and allowed to stir overnight while slowly warming to room temperature. The reaction mixture was poured into dilute aqueous citric acid and the product collected by vacuum filtration and water washed. Purification by recrystallization from aqueous ethanol gave 0.30 g of the title compound as a solid, mp 197°–198.5° C. (dec). MS (FAB+) m/e 724 (M+H)+. $^1$H NMR (DMSO-$d_6$, 300 MHz) δ0.84 (m, 6H), 1.1–1.7 (m, 12H), 2.4–3.3 (m, 6H), 4.2 (m, 1H), 4.33 (m, 1H), 4.46 (m, 2H), 6.84 (d, J=9 Hz, 1H), 6.96 (t, 1H), 7.05 (t, 1H), 7.1 (s, 1H), 7.26 (br s, 1H), 7.31 (d, J=7.5 Hz, 1H), 7.38 (br s, 1H), 7.5–7.7 (m, 3H), 7.89 (d, J=9 Hz, 1H), 7.96 (d, J=9 Hz, 1H), 8.06 (d, J=7.5 Hz, 1H), 8.11 (s, 1H), 8.23 (d, J=7.5 Hz, 1H), 10.78 (s, 1H), 12.45 (br s, 1H). Anal calc for $C_{35}H_{45}N_7O_{10}\cdot 0.5H_2O$: C, 57.36; N, 6.34; N, 13.38. Found: C, 57.48; H, 6.30; N, 13.33.

EXAMPLE 13

BOC-Trp-Leu-Asp-(m-amino)Phe-NH$_2$ (Isomer A)

The product from Example 12f (0.064 g, 0.089 mmol) was dissolved in DMF (2 mL) and to this solution was added 5% Pd/BaSO$_4$ (15.3 mg). The reaction mixture was subsequently degassed and then pressurized to one atmosphere with hydrogen (balloon) at room temperature. After approximately one hour the solution was filtered to remove catalyst and the crude product purified by preparative C$_{18}$ reverse phase HPLC (mobile phase:acetonitrile-50 mmol ammonium acetate, pH 4.5) to give after lyophilization 0.048 g of the title compound as a white solid. MS (FAB−) m/e 692 (M+H)+. $^1$H NMR (DMSO-$d_6$, 300 MHz) δ0.85 (m, 6H), 1.1–1.7 (m, 12H), 2.4–3.2 (m, 6H), 4.15–4.45 (m, 3H), 4.5 (m, 1H), 6.37 (m, 3H), 6.75–7.2 (m, 5H), 7.26 (br s, 1H), 7.31 (d, J=7.5 Hz, 1H), 7.6 (d, J=7.5 Hz, 1H), 7.85 (br d, J=9 Hz, 1H), 7.95 (d, J=9 Hz, 1H), 8.33 (d, J=7.5 Hz, 1H), 10.81 (s, 1H). Anal calc for $C_{35}H_{47}N_7O_8 \cdot 1.5H_2O$: C, 58.31, H 7.00, N 13.60. Found: C 58.46, H 6.66, N 13.24.

EXAMPLE 14

Ctp-Leu-Asp-(dehydro)Phe-NH$_2$

The product from Example 11c (0.099 g, 0.201 mmol) was treated with 6 mL 1.5N HCl in glacial acetic acid at ambient temperature and the flask capped with a drierite filled drying tube. After 45 minutes the contents of the flask were frozen and lyophilized. The crude hydrochloride was sufficiently pure for use as isolated. To a solution of Ctp-OH (0.05 g, 0.191 mmol) prepared according to Yonemitsu et. al., *J.Am.Chem.Soc.*, 1966, 88 (17):3941, in DMF (1mL) and THF (2 mL) under a nitrogen atmosphere was added NMM (0.05 mL, 0.42 mmol) and the resulting solution cooled to −3° C. with an ice-salt bath. To this was added in one portion IBCF (0.026 mL, 0.191 mmol) and activation allowed to proceed 7 minutes. A previously prepared solution of the above hydrochloride (0.201 mmol) in DMF (2 mL) was subsequently added dropwise over 3 minutes and the mixture allowed to warm to room temperature. After 2.5 hours the reaction mixture was concentrated in vacuo. The residue was dissolved in methanol and then suspended in 10% citric acid solution. The crude product was collected by centrifuge and purified by preparative C$_{18}$ reverse phase HPLC (mobile phase:acetonitrile-50 mmol ammonium acetate, pH 4.5) to give after lyophilization 0.018 g of the title compound. MS (FAB+) m/e 617 (M+H)+. $^1$H NMR (DMSO-$d_6$, 300 MHz) δ0.89 (m, 6H), 1.5 (t, 2H), 1.65 (m, 2H), 2.6–2.9 (m, 2H), 4.2 (m, 2H), 4.35 (m, 1H), 4.55 (m, 1H), 6.75 (d, J=6 Hz, 1H), 6.9 7.05 (m, 2H), 7.13 (s, 1H), 7.2–7.45 (m, 6H), 7.58 (d, J=7.5 Hz, 2H), 8.35 (d, J=7.5 Hz, 1H), 8.66 (d, J=7.5 Hz, 1H), 9.45 (s, 1H), 10.93 (s, 1H). Anal calc for $C_{32}H_{36}N_6O_7 \cdot 2.5H_2O$: C, 58.07; H, 6.26; N, 12.70. Found: C, 57.75; H, 5.55; N, 12.44.

EXAMPLE 15

BOC-Trp-Tpp-Asp-(NMe)Phe-NH$_2$

15a: N-CBZ-(NMe)Phe-OH

To a solution of L-N-Me-Phe-OH (2.73 g, 15.23 mmol) and N,N-diisopropylethyl amine (4.13 g, 18.27 mmol) in dioxane/water (1:1 v/v, 100 mL), cooled to 0° C. was added benzyl chloroformate (3.10 g, 18.27 mmol) dropwise over 0.3 hour. The reaction was stirred overnight with warming to ambient temperature. Water (75 mL) was added and the solution acidified to pH 3-4 with solid citric acid and the aqueous phase extracted with ethyl acetate (3×) After drying over anhydrous sodium sulfate, the solvent was removed in vacuo to yield 4.54 g of the title compound as a clear, colorless oil; MS(EI) m/e 313 (M+). $^1$H NMR (CDCl$_3$, 300 MHz) δ2.65 (m, 3H), 2.96 (m, 1H), 3.28 (m, 1H), 4.84 (m, 1H), 5.02 (m, 2H), 7.10 (m, 10H).

15b: N-CBZ-(NMe)Phe-NH$_2$

To a solution of Example 5a (4.54 g, 14.5 mmol) and N-methylmorpholine (1.47 g, 14.5 mmol) in tetrahydrofuran (THF) (100 mL) cooled to −20° C. was added ethyl chloroformate (1.56 g, 14.5 mmol). After stirring for 0.25 hour, the solution was saturated with dry gaseous ammonia. The solution was warmed to 0° C. and stirred for 2.5 hours. The solvent was removed in vacuo and the residue partitioned between ethyl acetate (100 mL) and water (100 mL). The organic layer was separated, dried over anhydrous sodium sulfate, and the solvent removed in vacuo. The residue was recrystallized (ethyl acetate/hexanes) to yield 2.34 g of the title compound as a white solid in two crops; MS(EI) m/e 312 (M+). $^1$H NMR(DMSO-d$_6$, 300 MHz) δ2.70 (m, 3H), 2.85 (m, 1H), 3.14 (m, 1H), 4.75 (m, 3H), 7.10 (m, 11H), 7.45 (m, 1H).

15c: (NMe)Phe-NH$_2$

A mixture of Example 5b (2.0 g, 6.40 mmol) and 5% Pd/BaSO$_4$ in methanol (100 mL) was hydrogenated under one atmosphere of hydrogen at ambient temperature overnight. The catalyst was filtered and the solvent was removed in vacuo to yield 1.14 g of the title compound as a white solid. MS(EI) m/e 179 (M+H)+.

15d: BOC-ASp(OBn)-(NMe)Phe-NH$_2$

To a solution of Example 5c (1.0 g, 5.61 mmol) in ethyl acetate (100 mL) cooled to 0° C. were added BOC-Asp(OBn)OH (1.81 g, 5.61 mmol) 4-N,N-dimethylaminopyridine (4-DMAP) (0.07 g, 0.56 mmol) and DCCl (1.39 g, 6.73 mmol). The suspension was stirred vigorously at 0° C. for 4 hours and filtered. The filtrate was washed with aqueous solutions of 0.1N HCl (3×) and saturated NaHCO$_3$ (3×). After drying over anhydrous sodium sulfate, the solvent was removed in vacuo. The residue was chromatographed (ethyl acetate/hexanes) to yield 1.62 g of the title compound as a amorphous solid; MS(EI) m/e 483 (M+).

15e: Asp(OBn)-(NMe)Phe-NH$_2$ hydrochloride

Example 5d (1.62 g, 3.35 mmol) in acetic acid (10 mL) was treated with 1.5N HCl/acetic acid (8 mL) for 0.3 hour. The solution was triturated with diethyl ether to yield 1.40 g of the title compound as a white solid; MS(FAB+) m/e 384 (M+H)+.

15f: BOC-Tpp-Asp(OBn)-(NMe)Phe-NH$_2$

To a solution of BOC-(trans-3-n-propyl)proline (1.03 g, 4.0 mmol, prepared as in Example 34 g below) in THF (75 mL) under nitrogen at ambient temperature was added NMM (0.5 mL, 4.4 mmol) and the resulting solution cooled to −10/−15° C. To this was added IBCF (0.52 mL, 4.0 mmol) and the activation allowed to proceed 6 minutes. A freshly prepared solution of Asp(OBn)-(NMe)Phe-NH$_2$ hydrochloride (1.68 g, 4.0 mmol), prepared as in Example 5e, in DMF (40 mL) was subsequently added (rapidly) dropwise over 5 minutes followed by the (slow) dropwise addition of a solution of NMM (0.5 mL, 4,4 mmol) in THF (75 mL) over one hour while slowly warming the reaction mixture to 0° C. After stirring an additional 30 minutes, the mixture was partitioned between ethyl acetate and dilute aqueous HCl. The organic phase was washed once each with water, 5% sodium bicarbonate and water then dried (magnesium sulfate), filtered and concentrated in vacuo. The crude product was purified by flash chromatography on silica gel (eluting with ethyl acetate-hexane) to give 2.01 g of the title compound as a foam. MS m/e 623 (M+H)+, m/e 640 (M+NH$_4$)+. $^1$H NMR (DMSO-d$_6$, 300 MHz) δ0.82 (m, 3H), 1.1–1.6 (m, 14H), 1.85 (m, 2H), 2.2–3.7 (m, 12H), 4.75 (m, 1H), 4.85–5.2 (m, 4H), 7.0–7.6 (m, 12H), 8.3–8.6 (m, 1H). Anal calc for C$_{34}$H$_{46}$N$_4$O$_7$.0.5H$_2$O: C, 64.63; H, 7.51; N, 8.87. Found: C, 64.46; H, 7.51; N, 8.68.

15g: Tpp-Asp(OBn)-(NMe)Phe-NH$_2$ Hydrochloride

The product from Example 15f (2.01 g, 3.23 mmol) was treated at ambient temperature with 10 mL of 1.44N HCl in glacial acetic acid. The flask was capped with a drierite filled drying tube and allowed to stir 40 minutes. The product was precipitated with ethyl ether (400 mL), collected by vacuum filtration and dried in vacuo at ambient temperature to give 1.56 g of the title compound as a white solid product. Anal Calc for C$_{29}$H$_{38}$N$_4$O$_5$. HCl.H$_2$O: C, 60.34; H, 7.00; N, 9.71. Found: C, 60.67; H, 6.90; N, 9.76.

15h: BOC-Trp-Tpp-Asp(OBn)-(NMe)Phe-NH$_2$

The product from Example 15g (1.56 g, 2.79 mmol) was combined with BOC-Trp-OH (0.85 g, 2.79 mole), HOBt (0.38 g, 2.79 mmol) and EDCl (0.54 g, 2.79 mmol) under nitrogen and to this mixture was added DMF (20 mL). The resulting solution was chilled in an ice bath and to the cold solution was added DIEA (0.53 mL, 3.07 mmol). The reaction mixture was allowed to warm to ambient temperature. After approximately 3.5 hours, the mixture was partitioned between ethyl acetate and dilute hydrochloric acid. The organic phase was dried (magnesium sulfate), filtered and concentrated in vacuo. The crude product was purified by flash chromatography on silica gel (eluting with ethyl acetate-hexane) to give 1.59 g of the title compound. MS (FAB+) m/e 809 (M+H)$^{30}$, m/e 831 (M+Na)+. $^1$H NMR (DMSO-d$_6$, 300 MHz) δ0.83 (m, 3H), 1.1–1.6 (m, 13H), 2.0 (m, 2H), 2.2–3.6 (m, 10H), 3.7–3.95 (m, 2H), 4.2–4.5 (m, 1H), 4.7–5.7 (m, 4H), 6.85–7.6 (m, 18H), 8.32–8.53 (m, 1H), 10.75–10.92 (m, 1H). Anal calc for C$_{45}$H$_{56}$N$_6$O$_8$.1.5-H$_2$O: C, 64.63; H, 7.13; N, 10.05. Found: C, 64.67; H; 6.75; N, 10.02.

15i: BOC-Trp-Tpp-Asp-(NMe)Phe-NH$_2$

The product from Example 15h (0.072 g, 0.087 mmol) was dissolved in methanol (5 mL) to which was added 10% Pd/C (0.035 g). The mixture was degassed then subjected to hydrogenolysis in a Parr shaker under 4 atmospheres hydrogen at room temperature. The reaction mixture was filtered through Celite ® and the filtrate concentrated in vacuo. The crude product was purified by preparative C$_{18}$ reverse phase HPLC (acetonitrile-50 mmol ammonium acetate pH 4.5) to give after lyophilization 0.037 g the title compound. MS (FAB+) m/e 719 (M+H)+. $^1$H NMR (DMSO-d$_6$, 300 MHz) δ0.83 (m, 2H), 1.1–1.6 (m, 13H), 1.8–2.1 (m, 2H), 2.3–3.5 (m, 10H), 3.7–4.0 (m, 2H), 4.2–4.5 (m, 1H), 4.75–5.2 (m, 3H), 6.9–7.6 (m, 13H), 8.2–8.5 (m, 1H), Anal calc for C$_{38}$H$_{50}$N$_6$O$_8$.2H$_2$O: C, 60.45; H, 7.22; N, 11.13. Found: C, 60.19; H, 6.67; N, 11.14.

EXAMPLE 16

BOC-Trp-Nle-Asp-(dehydro)Phe-NH$_2$

The fully protected dehydrodipeptide (0.78 g, 1.81 mmol), prepared as outlined in Example 11c, was treated at ambient temperature under nitrogen with excess 1.4N HCl in glacial acetic acid. After 2.5 hours, methanol was added until the solution became homogeneous and the product subsequently precipitated by the dropwise addition of ethyl ether (125 mL). Vacuum filtration, followed by drying in vacuo at ambient temperature, gave 0.55 g of the hydrochloride as a white solid suitable for use without further purification. To a solution of BOC-Nle-OH (0.19 g, 0.80 mmol) in THF (10 mL) under nitrogen was added NMM (0.20 mL, 1.75 mmol) and the resulting solution cooled to −15/−20° C. To this was added in one portion IBCF (0.10 mL, 0.80 mmol). The activation was allowed to proceed 8 minutes upon which time a previously prepared solution of the above hydrochloride (0.25 g, 0.80 mmol) in DMF (7 mL) was aded dropwise over 3 minutes. The reaction mixture was subsequently warmed to 0/+5° C. After one hour, the contents of the flask were partitioned between ethyl acetate and dilute aqueous hydrochloric acid. The organic phase was washed once with water, dried (magnesium sulfate), filtered and concentrated in vacuo. The crude product was purified by recrystallization from ethyl acetate-acetone to give 0.20 g of the title compound as a solid product, mp 180°–182° C. (dec). MS (FAB+) m/e 491 (M+H)+, m/e 513 (M+Na)+. $^1$H NMR (DMSO-d$_6$, 300 MHz) δ0.82 (m, 3H), 1.15–1.65 (m, 15H), 2.6–2.9 (m, 2H), 3.88 (m, 1H), 4.57 (m, 1H), 7.05 (d, J=7.5 Hz, 1H), 7.14 (br s, 1H), 7.25–7.40 (m, 4H), 7.55 (dd, 1H), 8.46 (d, J=7.5 Hz, 1H), 9.32 (s, 1H), 12.53 (br s, 1H). Anal calc for C$_{24}$H$_{34}$N$_4$O$_7$: C, 58.75; H, 7.00; N, 11.42. Found: C, 58.46; H, 6.92; N, 11.08.

16b: BOC-Trp-Nle-Asp-(dehydro)Phe-NH$_2$

The product from Example 16a (0.184 g, 0.375 mmol) was treated with excess 1.57N HCl in glacial acetic acid. The flask was capped with a drierite filled drying tube and the contents allowed to stir at ambient temperature. After approximately 1.5 hour the contents of the flask were frozen and lyophilized. The crude hydrochloride was sufficiently pure for use as isolated. The hydrochloride (0.375 mmol) and BOC-Trp-OSu (0.15 g, 0.375 mmol) were combined and to this mixture was added, under nitrogen, DMF (5 mL). The resulting solution was cooled in an ice bath and DIEA (0.15 mL, 0.825 mmol) added. The mixture was allowed to stir overnight while slowly warming to ambient temperature. The reaction mixture was subsequently poured into dilute aqueous hydrochloric acid. The crude product was collected by vacuum filtration and washed with water. Purification by recrystallization from aqueous ethanol gave 0.184 g of the title compound as a solid product, mp 193.5°–194.5° C. (dec); MS (FAB−) m/e 675 (M—H)−. $^1$H NMR (DMSO-d$_6$, 300 MHz) δ0.82 (m, 3H), 1.05–1.75 (m, 15H), 2.55–3.15 (m, 4H), 4.21 (m, 1H), 4.31 (m, 1H), 4.62 (m, 1H), 6.88 (d, J=7.5 Hz, 1H), 6.97 (t, 1H), 7.05 (t, 1H), 7.12 (s, 1H), 7.17 (br s, 1H), 7.25–7.40 (m, 5H), 7.58 (m, 3H), 7.97 (d, J=7.5 Hz, 1H), 8.5 (d, J=7.5 Hz, 1H), 9.52 (s, 1H), 10.78 (s, 1H), 12.58 (br s, 1H). Anal calc for C$_{35}$H$_{44}$N$_6$O$_8$0.5H$_2$O: C, 61.29; H, 6.63; N, 12.26. Found: C, 61.40; H, 6.60; N, 12.37.

EXAMPLE 17

N$^\alpha$-BOC-N$^{in}$-formyl-Trp-Leu-Asp-Phe-NH$_2$

17a: N$^\alpha$-BOC-N$^{in}$-formyl-Trp-succinimide ester

To a solution of N$^\alpha$-BOC-N$^{in}$-formyl-Trp (200 mg, 0.60 mmol) in 6 mL of anhydrous DME was added N-hydroxysuccinimide (69 mg, 0.60 mmol) and DCC (200 mg, 1.0 mmol) at ambient temperature and stirred for 48 hours under nitrogen atmosphere. Dicyclohexyl urea was removed by filtration, the solvent evaporated and the residue dissolved in ethyl acetate. The filtration process was repeated. Ethyl acetate was then evaporated to give the title compound (205 mg, 80% yield) as a crisp white foam. $^1$H NMR (CDCl$_3$, 60 MHz) δ1.4 (s, 9H), 2.8 (s, 4H), 3.4 (dd, 2H), 5.1 (br s, 1H), 7.2–7.6 (m, 5H), 9.1 (br s, 1H).

17b: N$^\alpha$-BOC-N$^{in}$-formyl-Trp-Leu-Asp-Phe-NH$_2$

To a solution of Leu-Asp-Phe-NH$_2$·HCl (349 mg, 0.80 mmol) in 6 mL anhydrous DMF was added DIEA (0.28 mL, 1.60 mmol) and a solution of Example 17a (350 mg. 0.82 mmol) in 6 mL anhydrous DMF at 0° C. The resulting solution was stirred for 24 hours with warming to ambient temperature under nitrogen atmosphere. The reaction mixture was poured into a rapidly stirring solution of cold 10% citric acid causing a white precipitate. The solid was collected and recrystallized from ethanol to give the title compound (280 mg, 50%) as a white solid, mp 215°–218° C., [α]$_D^{23}$=−30.6° (c=0.3, DMF); MS(FAB+) m/e 707 (M+H)+. $^1$H NMR(DMSO-d$_6$, 300 MHz) δ0.81–0.87 (2d, 6H), 1.29 (s, 9H), 1.13 (m, 1H), 1.33–1.70 (m, 2H), 2.44–2.50 (dd, 1H), 2.65–2.73 (dd, 1H), 2.80–3.08 (m, 4H), 4.26–4.36 (m, 3H), 4.52 (q, 1H), 7.18–7.38 (m, 10H) and six D$_2$O exchangeable protons. Anal Calcd for C$_{36}$H$_{46}$N$_6$O$_9$·0.5 H$_2$O: C, 60.42; H, 6.34; N, 11.75. Found: C, 60.62; H, 6.54; N, 11.60.

EXAMPLE 18

(2′,3′-dihydro)Trp-Leu-Asp-Phe-NH$_2$·HCl

18a: N$^\alpha$-BOC-N$^{in}$-BOC-(2′,3′-dihydro)Trp succinimide ester

To a solution of N$^\alpha$-BOC-N$^{in}$-BOC-(2′,3′-dihydro)Trp (407 mg, 1.0 mmol) in 10 mL anhydrous DME was added N-hydroxysuccinimide (115 mg, 1.0 mmol) and DCC (309 mg, 1.5 mmol). The reaction mixture was stirred at ambient temperature for 48 hours under nitrogen atmosphere. Dicyclohexyl urea was removed by filtration, the solvent evaporated and the residue dissolved in ethyl acetate. The filtration process was repeated. The ethyl acetate was then evaporated to give the title compound (400 mg, 80% yield) as a crisp, slightly yellow foam. $^1$HNMR (CDCl$_3$, 60 MHz) δ1.15 (d, 18H), 1.9–2.4 (s, 2H), 2.8 (s, 4H), 3.3–5.3 (m, 7H), 6.8–7.8 (m, 4H). 18b: N$^\alpha$-BOC-N$^{in}$-BOC-(2′,3′-dihydro)Trp-Leu-Asp-Phe-NH$_2$ To a solution of Leu-Asp-Phe-NH$_2$·HCl (420 mg, 1.0 mmol) in 8 mL anhydrous DMF was added DIEA (0.35 mL, 2.0 mmol) and a solution of Example 18a (500 mg, 1.0 mmol) in 6 mL anhydrous DMF at 0° C. The resulting solution was stirred for 24 hours at ambient temperature under nitrogen atmosphere. The reaction mixture was poured into a rapidly stirred solution of cold 10% citric acid, causing a white precipitate which was collected and recrystallized from EtOH/H$_2$O to give the title compound (429 mg, 55% yield) as a white solid, mp 193°–195° C., [α]$_D^{23}$=−30.4° (c 0.5; DMF, mixture of a pair of diastereomers), MS(FAB+) m/e 781(M+H)+., $^1$H NMR(DMSO-d$_6$/D$_2$O, 300 MHz) δ0.85 (2d, 6H), 1.4 (s, 9H), 1.5 (s, 9H), 1.55–1.85 (m, 2H), 2.0–2.13 (m, 1H), 2.45–3.12 (m, 7H), 3.25–3.40 (m, 1H), 3.63 (dd, 1H), 4.0–4.15 (m, 2H), 4.18–4.28 (m, 1H), 4.36 (dd, 1H), 4.47 (t, 1H), 6.90 (t, 1H), 7.1–7.30 (m, 9H). Anal Calcd for C$_{40}$H$_{56}$N$_6$O$_{10}$.1H$_2$O: C, 60.11; H, 7.32; N, 10.52. Found: C, 60.18; H, 7.33; N, 10.13.

18c: (2′,3′-Dihydro)Trp-Leu-Asp-Phe-NH$_2$.HCl

The protected peptide in Example 18b (200 mg, 0.26 mmol) was treated with 6 mL of 4N HCl/dioxane and stirred under nitrogen at ambient temperature for 3 hours. Anhydrous ether was added to the reaction with vigourous stirring causing a white precipitate. The precipitate was collected and recrystallized from EtOH-/EtOAc afford the title compound (150 mg, 90% yield) as a slightly cream colored solid. [α]$_D^{23}$= −0.27° (c 0.75; DMF, mixture of a pair of diastereomers at benzylic carbon of indoline moiety), mp 175° C. (dec), MS(FAB+) m/e 581(M+H)+ for free base., $^1$H NMR (DMSO-d$_6$/D$_2$O, 300 MHz) δ0.90 (2d, 6H), 1.34–1.55 (m, 2H), 1.61–1.83 (m, 1H), 1.94–2.11 (m, 1H), 2.20–2.33 (m, 1H), 2.45–2.85 (two dd and one m, 5H), 3.03 (dd, 1H), 3.39 (dd, 1H), 3.56–3.67 (m, 1H), 3.90–4.0 (m, 1H), 4.3–4.45 (m, 1H), 4.45–4.60 (m, 1H), 7.15–7.45 (m, 9H).

EXAMPLE 19

BOC-[5-Amino-2-(1H-indol-3-ylmethyl)-pentanoyl]-Leu-Asp-Phe-NH$_2$

19a: Benzyl α-(1H-indol-3-ylmethyl)-α-(triphenylphosphoranylidene)acetate

The compound was prepared in an identical manner to that described by M. Strandtmann, et al, *J. Org. Chem.*, 1968, 33:4306 (1968), mp 152°–154° C. MS(CI) m/e 540 (M+H)+. $^1$H NMR(CDCl$_3$, 300 MHz) δ3.56 (d, J=18 Hz, 2H), 4.84 (br s, 1H), 5.15 (br s, 1H), 6.60 (s, 1H), 6.67 (br s, 1H), 6.93 (t, J=7.5 Hz, 1H), 7.03 (br s, 1H), 7.08 (t, J=7.5 Hz, 1H), 7.20–7.38 (m, 10H), 7.38–7.57 (m, 10H), 7.73 (s, 1H). Anal calc for C$_{36}$H$_{30}$NO$_2$P.0.5H$_2$O: C, 78.80; H, 5.71; N, 2.55. Found: C, 79.05; H, 5.80; N, 2.36.

19b: BOC-5-amino-2-(1H-indol-3-ylmethyl)-2-pentenoic acid benzyl ester

To a solution of ylide from Example 19a (10 g, 18 mmol) in 100 mL of anhydrous methylene chloride was added a solution of BOC-3-aminopropanal (E. J. Corey, et al, *Tetrahedron Lett.* 1979, 399) (2.1 g, 12 mmol) in 30 mL anhydrous CH$_2$Cl$_2$. After stirring at ambient temperature for three days, the product was purified by flash silica gel eluting with EtOAC/Hexane (1/3∼3/1, v/v) to afford the title compound (4.2 g, 80% yield) as a yellow oil. $^1$H NMR (CDCl$_3$, 300 MHz) δ1.4 (s, 9H), 2.6 & 2.6 (2q, 2H), 3.17 & 3.24 (2q, 2H), 3.77 & 3.83 (2s, 2H), 4.56 & 4.8 (br., 1H), 5.16 (s, 2H), 5.95 (t, 1H), 6.84 (br s, 1H), 6.9 (t, 1H), 7.1 (t, 1H), 7.18 (t, 1H), 7.24–7.38 (m, 6H), 7.6 (d, 1H), 7.96 (br. 1H)., m/e calculated for C$_{26}$H$_{30}$N$_2$O$_4$ 434.2205. Found: 434.2208.

19c: BOC-5-amino-2-(1H-indol-3-ylmethyl)pentanoic acid

The product from Example 19b (766 mg, 1.7 mmol) was dissolved in 30 mL of ethyl acetate and to this solution was added 600 mg of 10% Pd/C. The reaction mixture was stirred under hydrogen atmosphere for 6 hours. Filtration of the reaction mixture through a Celite ® pad, followed by several washings with methanol, afforded filtrate which after concentration was purified by flash silica gel using 1% HOAc/EtOAc (½∼1/1, v/v) as eluent to provide the title compound (480 mg, 81% yield) as an oil: $^1$H NMR (CDCl$_3$, 300 MHz) δ1.4 (s, 9H), 1.5–1.75 (m, 4H), 2.5 & 2.8 (m, 1H), 3.05 (dd, 2H), 3.10–3.28 (m, 2H), 3.8 & 4.6 (2 br s, 1H), 6.9 (br s, 1H), 7.1 (t, 1H), 7.16 (t, 1H), 7.33 (d, 1H), 7.58 (2d, 1H), 8.2 (br s, 1H)., m/e calculated for C$_{19}$H$_{26}$N$_2$O$_4$ 346.1892. Found: 346.1898.

19d: BOC-5-amino-2-(1H-indol-3-ylmethyl)pentanoic acid 2,4,5-trichlorophenyl ester To a solution of Example 19c (233 mg, 0.67 mmol) in 10 mL anhydrous methylene chloride was added 2,4,5-trichlorophenol (133 mg, 0.67 mmol) and EDCl (191 mg, 1.0 mmol). The solution was stirred at ambient temperature for 24 hours under nitrogen atmosphere. The reaction mixture was washed with H$_2$O (2×) and brine. The organic layer was concentrated and the residue was purified by flash chromatography on silica gel using 1% HOAc/EtOAc/Hexane (1/5∼⅓, v/v) as eluents to afford the title compound (183 mg, 52% yield) as a white, crisp foam: $^1$H NMR(CDCl$_3$, 300 MHz) δ1.44 (s, 9H), 1.6–1.9 (m, 4H), 3.08–3.3 (m, 5H), 4.55 (br.t, 1H), 6.67 (s, 1H), 7.06 (d, 1H), 7.14 (s, 1H), 7.1–7.3 (2t,2H), 7.4 (d, 1H), 7.62 (d, 1H), 8.12 (br, 1H).

19e: BOC-[5-Amino-2-(1H-indol-3-ylmethyl)pentanoyl]-Leu-Asp-Phe-NH$_2$

A solution of Leu-Asp-Phe-NH$_2$.HCl (129 mg, 0.30 mmol) in 5 mL anhydrous DMF was treated with DIEA (0.12 mL, 0.68 mmol), HOBt (40 mg, 0.30 mmol) and a solution of Example 22c (158 mg, 0.3 mmol) in 5 mL anhydrous DMF at 0° C. The resulting solution was stirred with warming to ambient temperature for 24 hours under a nitrogen atmosphere. The mixture then was poured into a cold, rapidly stirring solution of 10% citric acid causing a white precipitate which was collected and purified by flash silica gel using EtOAc/pyridine/HOAc/H$_2$O (24/4/1.2/2.2) as an eluent and after lyopholization afforded the title compound (120 mg, 55% yield) as a white solid, mp 179°–181° C. HPLC analysis (C$_{18}$-ultrasphere ODS with CH$_3$CN/H$_2$O/T-FA=40/60/0.1 as eluent) revealed a diastereomeric ratio of 45/55 at the carbon that bears indolemethylene moiety. [α]$_D^{23}$= −28.6° (c 0.6; DMF), MS(FAB+) m/e 721 (M+H)+, $^1$H NMR(DMSO-d$_6$, 300 MHz) δ0.61, 0.69, 0.81, 0.85 (4d,6H), 1.34, 1.36 (2s, 9H), 1.11–1.60 (m, 5H), 2.40–2.70 (m, 4H), 2.70–3,10 (m, 5H), 4.13–4.24 (m, 1H), 4.25–4.40 (m, 2H), 4.40–4.50 (m, 1H), 6.90–7.60 (m, 10 Ar-H), and eight D$_2$O exchangable protons. Anal calc for C$_{38}$H$_{52}$N$_6$O$_8$.0.5 H$_2$O: C, 62.55; H, 7.32; N, 11.52. Found: C, 62.80; H, 7.43; N, 11.63.

EXAMPLE 20

BOC-[5-amino-2-(1H-indol-3-ylmethyl)-2-pentenoyl]-Leu-Asp-Phe-NH$_2$

20a: BOC-5-amino-2-(1H-indol-3-ylmethyl)-2-pentenoic acid

To a solution of the compound of Example 19b (400 mg, 0.92 mmol) in 18 mL of ethanol was added 400 mg of 10% Pd on carbon. The reaction mixture was flushed with nitrogen and cooled in an ice bath and then 1,4-cyclohexadiene (2.6 mL, 28 mmol) was added. The reaction mixture was stirred at ambient temperature under nitrogen atmosphere for 4 hours. Filtration of the reaction mixture through a Celite ® pad, followed by several washings with ethanol and evaporation, afforded an oily residue which was purified by flash silica gel eluting with EtOAc/hexane (1/1, v/v, with 1% HOAc) to afford the acid (269 mg, 85%): MS m/e 344

(M+), $^1$H NMR(CDCl$_3$, 300 MHz) δ1.4 (s, 9H), 2.5 (q, 2H), 3.20 (q, 2H), 3.77 (br s, 2H), 4.60 (br t, 1H), 6.87 (br s, 1H), 6.96 (t, 1H), 7.16 (t, 1H), 7.18 (t, 1H), 7.32 (d, 1H), 7.26 (d, 1H), 7.90 (br. 1H).

20b: BOC-5-amino-2-(1H-indol-3-ylmethyl)-2-pentenoic acid 2,4,5-trichlorophenyl ester A solution of acid in Example 20a (195 mg, 0.57 mmol) in 8 mL anhydrous methylene chloride was treated with 2,4,5-trichlorophenol (112 mg, 0.57 mmol) and EDCI (160 mg, 0.85 mmol). The reaction mixture was stirred for 24 hours at ambient temperature under nitrogen atmosphere. The mixture was washed with 10% citric acid and brine. The organic layer was dried over anhydrous sodium sulfate and concentrated to yield a residue that was purified by flash chromatography on silica gel. Elution with EtOAc/hexane (1/5~1/1, v/v, with 1% HOAc) afforded the title compound (158 mg, 54% yield) as an oil: $^1$H NMR (CDCl$_3$, 60 MHz) δ1.45 (s, 9H), 2.58 (q, 2H), 3.28 (q, 2H), 3.85 (q, 2H), 4.80 (br, 1H), 7.2 (s, 1H), 7.5 (s, 1H), 6.8-7.8 (m, 6H), 10.1 (br, 1H).

20c: BOC-[5-amino-2-(1H-indol-3-ylmethyl)-2-pentenoyl]-Leu-Asp-Phe-NH$_2$

A solution of Leu-Asp-Phe-NH$_2$.HCl (124 mg, 0.29 mmol) in 5 mL anhydrous DMF was treated with DIEA (0.10 mL, 0.58 mmol), HOBt (30 mg, 0.22 mmol) and a solution of the compound of Example 20b (153 mg, 0.29 mmol) in 5 mL of anhydrous DMF at 0° C. The resulting solution was stirred at ambient temperature under nitrogen atmosphere for 24 hours. The mixture was then poured into a rapidly stirring solution of cold 10% citric acid causing a white precipitate, which, after collection, was recrystallized from ethyl acetate to yield the title compound (124 mg, 60% yield) as a white solid, mp 179°-181° C., $[\alpha]_D^{23} = -13.7°$ (c 0.58; DMF)., MS(FAB+) m/e 719 (M+H)+. $^1$H NMR(DMSO-d$_6$, 300 MHz) δ0.72 & 0.72 (2d, 6H), 1.36 (s, 9H), 1.25-1.47 (m, 3H), 2.35 (q, 2H), 2.55 (dd, 2H), 2.88 (dd, 2H), 2.95-3.08 (m, 2H), 3.63 (q, 2H), 4.28-4.40 (m, 2H), 4.48 (q, 1H), 6.21 (t, 1H), 6.93 (t, 1H), 6.95 (d, 1H), 6.97 (br s, 1H), 7.04 (t, 1H), 7.15-7.25 (m, 6H) and eight D$_2$O exchangable protons., Anal Calcd for C$_{38}$H$_{50}$N$_6$O$_8$: C, 63.47; H, 7.01; N, 11.69. Found: C, 63.21; H, 7.24; N, 11.47.

EXAMPLE 21

N$^\alpha$-BOC-(N$^{in}$-propionyl)Trp-Leu-Asp-Phe-NH$_2$

21a: N$^\alpha$-BOC-(N$^{in}$-propionyl)Trp benzyl ester

A solution of BOC-Trp benzyl ester (200 mg, 0.5 mmol), (n-Bu)$_4$NHSO$_4$ (30 mg, cat.) and 40% NaOH aqueous solution (2 mL) was stirred vigorously in 6 mL benzene. Propionic anhydride (excess) was added in portions to the above mixture and the progress of reaction was monitored by tlc. As soon as the starting material was consumed as indicated by tlc, the reaction mixture was poured into 10 mL distilled water and was extracted with benzene. The organic layer was dried over anhydrous sodium sulfate, filtered and the solvent was evaporated. The residue was purified by flash chromatography on silica eluting with EtOAc/hexane (1/5~⅓, v/v) to afford the title compound 110 mg (48% yield) as a white solid. $^1$H NMR(CDCl$_3$, 60 MHz) δ1.24 (t, 3H), 1.20 (s, 9H), 2.77 (q, 2H), 3.22 (d, 2H), 4.79 (m, 1H), 5.17 (br s, 2H), 7.0-7.6 (m, 9H), 8.15-8.30 (m, 1H).

21b: N$^\alpha$-BOC-(N$^{in}$-propionyl)Trp-trichlorophenyl ester

The same procedure as described for Example 19b was used to provide the active ester in 63% yield from the compound of Example 21a. $^1$H NMR (CDCl$_3$/60 MHz) δ1.32 (t, 3H), 1.38 (s, 9H), 2.90 (q, 2H), 3.30-3.60 (br,2H), 4.90-5.25 (m, 1H), 7.1 (s, 1H), 7.20-7.70 (m, 5H), 8.30-8.70 (m, 1H).

21c: N$^\alpha$-BOC-(N$^{in}$-propionyl)Trp-Leu-Asp-Phe-NH$_2$

The same procedure as described for Example 20c was used to provide the peptide in 67% yield from the compound of Example 21b, mp 207°-208° C., MS(FAB-) m/e 733(M-H)-, $^1$H NMR(DMSO-d$_6$/300 MHz) δ0.85 (2d, 6H), 1.18 (t, 3H), 1.30 (s, 9H), 1.27-1.52 (m, 2H), 1.55-1.67 (m, 1H), 2.56 (dd, 2H), 2.50 (br, 1H), 2.78-3.15 (m, 5H), 4.25-4.42 (m, 3H), 4.52 (q, 1H), 7.1-7.40 (m, 10H) and seven D$_2$O exchangable protons. Anal calc for C$_{38}$H$_{50}$N$_6$O$_9$.0.5H$_2$O: C, 61.34; H, 6.91; N, 11.30. Found: C, 61.47; H, 7.13; N, 11.13.

EXAMPLE 22

BOC-8-amino-2-(1H-indol-3-ylmethyl)-2-octenoyl-Leu-Asp-Phe-NH$_2$

22a: Methyl BOC-8-amino-2-(1H-indol-3-ylmethyl)-2-octenoate

A solution of 6-(BOC-amino)hexanol (2.0 g, 9.20 mmol) in 5 mL of anhydrous methylene chloride was added to a suspension of dried, powdered 4A molecule sieves (10 g) and PDC (16 g, 42.5 mmol) in methylene chloride (100 mL) at ambient temperature and stirred for 1 hour. Dilution of the reaction mixture with diethyl ether, filtration through a Celite ® pad and evaporation afforded a brown oil, which was purified by flash chromatography on silica gel using EtOAc/hexane (½) as eluent to give desired aldehyde (1.24 g, 62% yield) which was immediately treated with methyl α-(3-indolemethyl)-α-(triphenyl phosphoranylidine)acetate (7.5 g, 16 mmol) in 50 mL methylene chloride and allowed to reflux for 4 days. The reaction mixture was concentrated to 8 mL and chromatographed on flash silica gel using EtOAc/toluene (1/7~¼, v/v) as eluents to afford the product (1.6 g, 43%) as a pale yellow oil. $^1$H NMR(CDCl$_3$, 60 MHz) δ1.37 (m, 6H), 1.47 (s, 9H), 2.30 (q, 2H), 3.06 (br d, 2H), 3.71 (s, 3H), 3.81 (s, 2H), 4.50 (br s, 1H), 6.72-7.77 (m, 6H), 8.33 (br s, 1H).

22b: BOC-8-amino-2-(1H-indol-3-ylmethyl)-2-octenoic acid

A solution of the compound of Example 22a (564 mg, 1.41 mmol) in 1.0M NaOH/MeOH (32 mL) was heated to reflux for 4 hours. Additional 1.0M NaOH (10 mL) was added and the mixture was refluxed for an additional 3 hours. The methanol was removed under reduced pressure and the aqueous layer was acidified with 2.0N HCl (20 mL) and extracted with three portions of ethyl acetate. The combined extracts were dried over anhydrous sodium sulfate and concentrated to afford the title compound as an orange oil (yield not determined). $^1$H NMR (CDCl$_3$, 60 MHz) δ1.32 (m, 6H), 1.43 (s, 9H), 2.17-2.50 (m, 1H), 2.75-3.30 (m, 3H), 3.40 (s, 1H), 3.79 (s, 1H), 5.49 (br,s, 1H), 6.77-7.77 (m, 5H), 8.30 (br,d, 1H), 8.87 (br,s, 1H).

22c: BOC-8-amino-2-(1H-indol-3-ylmethyl)-2-octenoic acid 2,4,5-trichlorophenol ester A solution of the crude acid of Example 22b in 7 mL methylene chloride was treated with 2,4,5-trichlorophenol (330 mg, 1.69 mmol) and E mmol) and allowed to stir for 5 days at ambient temperature. The mixture was washed with 10% citric acid solution (2×), then brine. After drying, the solvent was evaporated and the resulting residue purified by flash chromatography on silica gel using ethyl acetate/hexane (1/10~1/5, v/v) as eluents to afford a pale yellow oil (562 mg, 70% yield from Example 22a). MS(DCI) m/e 565(M+H)+, ¹H NMR(CDCl₃, 300 MHz) δ1.3–1.4 (m, 4H), 1.45 (s, 9H), 1.47 (s, 2H), 2.0–2.1 (m, 1H), 2.42 (q, 1H), 3.0–3.15 (m, 3H), 3.90 (s, 1H), 4.47 (br s, 1H), 6.95–7.0 (m, 1H), 7.05–7.30 (m, 4H), 7.23 (s, 1H), 7.38 (t, 1H), 7.51 (d, 1H), 7.63 (d, 1H).

22d: BOC-8-amino-2-(1H-indol-3-ylmethyl)-2-octenoyl-Leu-Asp-Phe-NH₂

A solution of Leu-Asp-Phe-NH₂ (86 mg, 0.22 mmol) in 1 mL anhydrous DMF was treated with DIEA (38 μL, 0.22 mmol), HOBt (cat.) and a solution of the compound of Example 22c (125 mg, 0.22 mmol) in 1 mL anhydrous DMF at 0° C. The solution was heated to 40° C. under nitrogen atmosphere over night. After cooling to room temperature, the mixture was poured into a rapidly stirring solution of cold 10% citric acid causing formation of a white precipitate which was collected and recrystallized from ethyl acetate give the title compound (94 mg, 56% yield) as a white solid. Analytical HPLC [Altex C₁₈; 50 mM NH₄OAc, (pH 4.5)/AcCN linear gradient: 30% for 5 min, then 30–45% over 10 min; flow rate 1.0 mL/min] revealed a isomer ratio about 1/1, mp 166°–169° C., MS(FAB+) m/e 761(M+H)+. ¹H NMR(DMSO-d₆, 300 MHz) δ0.63–0.88 (m, 6H), 1.10–1.46 (m, 9H), 1.36 (s, 9H), 2.60–2.76 (m, 2H), 2.76–2.93 (m, 3H), 2.96–3.07 (m, 2H), 3.68 (dt, 1H), 4.27–4.52 (m, 2H), 5.38–5.47 and 6.29 (m & t, 1H), 6.9–7.08 (m, 3H), 7.11–7.27 (m, 5H), 7.29 (d, 1H), 7.49 (d, 1H), 7.72 (d, 1H), 7.79 (d, 1H), 7.95 (dd, 1H), 10.74 (br, s, 1H). Anal calc for C₄₁H₅₆N₆O₈.0.5-H₂O: C, 63.95; H, 7.48; N 10.92. Found: C, 63.81; H, 7.58; N, 10.77.

EXAMPLE 23

BOC-Glyψ[CH=CH]Trp-Leu-Asp-Phe-NH₂

23a: 4-(BOC-amino)-1-butene-3-ol

To a suspension of dried, powdered 4 A molecular sieves (18 g) and PDC (45 mg, 120 mmol) in 150 mL CH₂Cl₂ was added a solution of 2-(BOC-amino)ethanol (4.83 g, 30 mmol) in CH₂Cl₂. The mixture was allowed to stir at ambient temperature for 1.5 hour, then diluted with ether (200 mL) and filtered through a silica gel pad, rinsing throughly with ether. The filtrate was concentrated to afford a clear pale yellow oil (3.46 g, 72%). The aldehyde was used immediately for the next reaction without purification. To a cooled solution of the freshly prepared BOC-Glycinal (410 mg, 2.6 mmol) in 8 mL THF was slowly added 1.0M vinyl magnesium bromide in THF (18 mL) via syringe. The reaction mixture was allowed to stir for 1 hour with warming to −10° C. The reaction was quenched with saturated aqueous ammonium chloride (20 mL) and was extracted with chloroform (×4). The extracts were dried and concentrated. The crude oil was purified by flash chromatography on silica gel, eluting with EtOAc/hexane (1/5~1/1, v/v) to give the title compound as a clear pale yellow oil (380 mg, 78% yield). MS(DCI) m/e 205(M+NH₄)+. ¹H NMR(CDCl₃, 300 MHZ) δ1.45 (s, 9H), 2.54 (br s, 1H), 3.10 (dt, 1H), 3.30–3.43 (m, 1H), 4.24 (br s, 1H), 4.92 (br s, 1H), 5.21 (d, 1H), 5.35 (d, 1H), 5.86 (ddd, 1H). Anal calc for C₉H₁₇NO₃: C, 57.72; H, 9.17; N, 7.48. Found: C, 57.85; H, 9.19; N, 7.42.

23b: 4-(BOC-amino)-3-acetoxy-1-butene

A solution of the allylic alcohol of Example 23a (1.94 g, 10.4 mmol) in acetic anhydride (22 mL, 230 mmol) was treated with pyridine (2 mL) and DMAP (50 mg) at 0° C. The reaction mixture was warmed to ambient temperature, then stirred overnight. The mixture was poured into cold aqueous sodium bicarbonate solution and extracted with chloroform (4×). The extracts were dried over anhydrous sodium sulfate and concentrated. The crude oil was purified by flash chromatography on silica gel, eluting with EtOAc/hexane (1/10~⅓, v/v), to give the title compound as a colorless oil (1.92 g, 81% yield). MS(DCI) m/e 247(M+NH₄)+, ¹H NMR(CDCl₃, 300 MHz) δ1.45 (s, 9H), 2.10 (s, 3H), 3.28 (dt, 1H), 3.43 (dt, 1H), 4.72 (br s, 1H), 5.26 (d, 1H), 5.32 (d, 1H), 5.78 (ddd, 1H).

23c: Benzyl 4-acetoxy-5-(BOC-amino)-2-(1H-indol-3-ylmethyl)-trans-2-pentenoate

A solution of the compound of Example 23b (1.15 g, 5.02 mmol) in 60 mL acetone was treated with osmium tetroxide (5 mL of 2.5% in t-BuOH) and N-methylmorpholine N-oxide (1.48 g, 10.9 mmol) at ambient temperature. After stirring for 5 minutes, a solution of sodium periodate (5.0 g, 23.4 mmol) in 37 mL water was added to the reaction mixture and allowed to stir at ambient temperature for 3.5 hours. The mixture was poured into water (60 mL) and extracted with chloroform (4×). The extracts were dried over anhydrous sodium sulfate and concentrated. The crude product was purified by flash chromatography on silica gel, eluting with EtOAc/hexane (⅓~2/1, v/v), to yield a pale yellow oil (1.02 g, 88% yield). To a solution of the freshly prepared aldehyde (1.02 g, 4.41 mmol) and phosphorane from Example 19a (4.80 g, 8.9 mmol) in 22 mL CH₂Cl₂ was stirred at ambient temperature over night. The solvent was evaporated and the crude oil was purified by flash chromatography on silica gel, eluting with EtOAc/hexane (1/10~⅓, v/v), to yield the title compound as a pale yellow oil (1.74 g, 80% yield). MS(DCI) m/e 510 (M+NH₄)+, ¹H NMR(CDCl₃, 300 MHz) δ1.40 (s, 9H), 2.04 (s, 3H), 3.32 (t, 2H), 3.94 (s, 2H), 4.66 (br s, 1H), 5.12 (s, 2H), 5.72 (dt, 1H), 6.67 (d, 1H), 6.97 (s, 1H), 7.10 (t, 1H), 7.14–7.22 (m, 3H), 7.24–7.30 (m, 3H), 7.33 (d, 1H), 7.64 (d, 1H), 8.0 (s, 1H).

23d: Benzyl 4-hydroxy-5-(BOC-amino)-2-(1H-indol-3-ylmethyl)-trans-2-pentenoate

To a solution of the compound of Example 23c (1.51 g, 3.06 mmol) in 75 mL methanol was added sodium carbonate (26.0 g) and stirred at ambient temperature for 1 hour. Sodium carbonate was removed by filtration, rinsing throughly with methylene chloride. The filtrate was poured into saturated aqueous ammonium chloride (100 mL), the layers were separated and the aqueous layer was extracted further with chloroform (3×). The extracts were dried over anhydrous sodium sulfate and concentrated. The crude oil was purified by flash chromatography on silica gel, eluting with EtOAc/Hexane (1/5~1/1, v/v), to give the product as a pale yellow oil (1.03 g, 75% yield). MS(FAB+) m/e 451 (M+H)+, ¹H NMR(CDCl₃, 300 MHz) δ1.43 (s, 9H), 2.97 (s, 1H), 3.10–3.32 (m, 2H), 3.87 (s, 2H), 4.65–4.76 (m, 1H), 4.85 (br s, 1H), 5.16 (s, 2H), 6.79 (d, 1H), 6.88 (s, 1H), 7.11 (t, 1H), 7.19 (t, 1H), 7.22–7.31 (m, 6H), 7.33 (d, 1H), 7.61 (d, 1H), 7.99 (s, 1H).

23e: Benzyl 4-bromo-5-(BOC-amino)-2-(1H-indol-3-ylmethyl)-trans-2-pentenoate

A solution of carbon tetrabromide (5.50 g, 16.6 mmol) in 72 mL THF was treated with triphenyl phosphine (4.12 g, 15.7 mmol) at 0° C. and allowed to stir for 15 minutes. A solution of the compound of Example 23d in 10 mL THF was added to the above complex via syringe. The reaction mixture was stirred for 2 hours with warming to ambient temperature then poured into cold 10% citric acid solution (150 mL) and extracted with chloroform (4×). The combined extracts were washed with 10% aqueous sodium thiosulfate (2×). The thiosulfate aqueous layer was back extracted with chloroform (2×), the extracts combined, dried over anhydrous sodium sulfate and concentrated. The crude oil was purified by flash chromatography on silica gel, eluting with EtOAc/hexane (1/5~1/1,v/v), to give the title compound as a yellow oil (0.75 g, 71% yield). MS(CDI) m/e 530,532 (M+NH$_4$)+, $^1$H NMR(CDCl$_3$, 300 MHz) δ1.42 (s, 9H), 3.54 (t, 2H), 3.88 (s, 2H), 4.90 (br s, 1H), 5.01 (dt, 1H), 5.15 (s, 2H), 6.92 (s, 1H), 6.93 (d, 1H), 7.13 (t, 1H), 7.17–7.25 (m, 3H), 7.25–7.31 (m, 3H), 7.35 (d, 1H), 7.63 (d, 1H), 7.98 (br s, 1H).

23f: Benzyl 4-bromo-5-(BOC-amino)-2-(1H-indol-3-ylmethyl)-trans-2-pentenoate

A solution of the compound of Example 23e (0.75 g, 1.46 mmol) in 36 mL glacial acetic acid was treated with zinc dust (3.8 g) and stirred at ambient temperature for 50 minutes. The mixture was diluted with diethyl ether (50 mL) and the zinc dust was removed by filtration and rinsed thoroughly with diethyl ether. The filtrate was washed with water (2×) and the aqueous extracts were backwashed with diethyl ether (2×). The organic phase was washed with brine, dried over anhydrous sodium sulfate and concentrated. The crude oil was purified by flash chromatography on silica gel, eluting with EtOAc/hexane (1/5~⅓,v/v), to give the title compound as a colorless oil (0.61 g, 97% yield). MS(CDI) m/e 452(M+NH$_4$)+, m/e calculated for C$_{26}$H$_{30}$N$_2$O$_4$: 435.2284. Found: 435.2280., $^1$H NMR(CDCl$_3$, 300 MHz) δ1.44 (s, 9H), 2.99 (dd, 1H), 3.25 (dd, 1H), 3.48 (q, 1H), 3.68 (br.t, 2H), 4.40 (br s, 1H), 5.51 (dt, J=6 and 15 Hz, 1H), 5.73 (dd, J=8 and 15 Hz, 1H), 6.89 (s, 1H), 7.11 (t, 1H), 7.14–7.22 (m, 3H), 7.26–7.32 (m, 3H), 7.34 (d, 1H), 7.56 (d, 1H), 7.96 (s, 1H).

23g: BOC-Glyψ[CH=CH]Trp-OH

To a suspension of 10% Pd/C (380 mg) in 1,4-cyclohexadiene (16.4 mL) was added a solution of the compound of Example 23f (380 mg, 0.87 mmol) in 17 mL MeOH and stirred at ambient temperature for 5 hours. The catalyst was removed by filtration and the filtrate was concentrated under reduced pressure. The oily residue was taken up in diethyl ether (20 mL) and washed with 0.5N NaOH (5×20 mL). The aqueous layers were backwashed with diethyl ether (2×25 mL). The combined organic extracts were washed with brine, dried over anhydrous sodium sulfate, and concentrated to recover the unreacted starting substrate (277 mg, 73% yield). The aqueous extracts were acidified with cold 2N HCl (30 mL) until pH 2 was attained, then extracted with ethyl acetate (4×100 mL). These extracts were washed with brine, dried over anhydrous sodium sulfate and concentrated to give the title compound as a yellow oil (43 mg, 14% yield). MS(FAB+) m/e 345(M+H)+, $^1$H NMR(CDCl$_3$, 300 MHz) δ1.44 (s, 9H), 2.99 (dd, 1H), 3.26 (dd, 1H), 3.43 (t, 1H), 3.68 (br s, 2H), 4.48 (br s, 1H), 5.54 (dt, J=5 and 15 Hz, 1H), 5.71 (dd, J=11 and 15 Hz, 1H), 6.99 (s, 1H), 7.11 (t, 1H), 7.19 (t, 1H), 7.34 (d, 1H), 7.58 (d, 1H), 8.07 (s, 1H).

23h: BOC-Glyψ[CH=CH]Trp-2,4,5-trichlorophenol ester

The same procedure as described in Example 19d was used to provide the desired active ester in 63% yield from the compound of Example 23. MS m/e 522, 524(M+), $^1$H NMR (CDCl$_3$, 300 MHz) δ1.46 (s, 9H), 3.12 (dd, 1H), 3.40 (dd, 1H), 3.65–3.81 (m, 1H), 4.50 (br s, 1H), 5.67 (dt, J=5 and 15 Hz, 1H), 5.83 (dd, J=8 and 15 Hz, 1H), 6.89 (s, 1H), 7.07 (s, 1H), 7.15 (t, 1H), 7.22 (t, 1H), 7.38 (d, 1H), 7.49 (s, 1H), 7.61 (d, 1H), 8.10 (s, 1H).

23i: BOC-Glyψ[CH=CH]Trp-Leu-Asp-Phe-NH$_2$

The same procedure as described in Example 20c was used to provide the product in 59% yield from the compound of Example 23h, mp 194°–196° C., M N$_6$O$_8$: 719.3768. Found: 719.3749, $^1$H NMR (CD$_3$OD, 300 MHz) δ0.62 (dd, 3H), 0.84 (dd, 3H), 1.15–1.23 (m, 1H), 1.35–1.57 (m, 2H), 1.42 (d, 9H), 2.50–2.84 (m, 2H), 2.84–3.01 (m, 2H), 3.08–3.28 (m, 2H), 3.35–3.48 (m, 1H), 3.59 (dd, 2H), 4.18–4.29 (m, 1H), 4.48–4.59 (m, 2H), 5.47–5.80 (m, 2H), 6.94–7.03 (m, 2H), 7.06 (t, 1H), 7.12–7.27 (m, 5H), 7.30 (d, 1H), 7.54 (d, 1H), Anal Cald for C$_{38}$H$_{50}$N$_6$O$_8$. 1.5H20: C, 71.17; H, 7.18; N, 11.27. Found: C, 61.33; H, 7.05; N, 11.18.

EXAMPLE 24

Ctp-Leu-Asp-Phe-NHNH$_2$

24a: BOC-Phe-NHNH-Cbz

To a solution of BOC-Phe-OH (3.0 g, 11.2 mmol) and Cbz-NHNH$_2$.HCl (Boeshagen, H. and Ullrich, J. Chem. Ber. 1959, 92:1478–80) (2.3 g, 11.2 mmol) in 100 mL of DMF at 0° C. were added diisopropylethylamine (1.95 mL, 1.45 g, 11.2 mmol) followed by 2-ethoxy-1-ethoxycarbonyl-1,2-dihydroquinoline (2.77 g, 11.2 mmol). The ice bath was removed and the solution was allowed to stir for 46 hours, and then the solvent was evaporated under reduced pressure. The residue was taken up in ethyl acetate and washed successively with 1M KHSO$_4$, water, saturated aqueous sodium bicarbonate, and brine, dried (anhydrous sodium sulfate) and evaporated to give 4.0 g of a foam. Recrystallization from EtOAc/hexane provided 3.2 g (86% yield) of the title compound as a white crystalline product, mp 114°–115.5° C. $^1$H-NMR (DMSO): δ1.27 (s, 9H), 2.76 (br d, J=12 Hz, 1H), 2.97 (br d, J=12 Hz, 1H), 4.18 (m, 1H), 5.09 (br s, 2H), 7.01 (br d, J=9 Hz, 1H), 7.15–7.40 (m, 10H), 9.29 (s, 1H), 9.95 (s, 1H). MS (EI) m/e 413 (M+), 357 (M-C$_4$H$_8$)+. Anal. calc. for C$_{22}$H$_{27}$N$_3$O$_5$: C, 63.89; H, 6.58; N, 10.17. Found: C, 63.86; H, 6.54; N, 9.99.

24b: BOC-Asp(OBn)-Phe-NHNH-CbZ

The product of Example 24a (2.7 g, 13.0 mmol) was N-deprotected with 1:1 CF$_3$CO$_2$H/CH$_2$Cl$_2$ for 1 hour in the usual manner. The crude salt from evaporation of the volatile components was dissolved in 20 mL of DMF, cooled on dry ice, and added to a solution of mixed anhydride prepared in the usual manner from BOC-Asp(Bn)-OH (1.96 g, 6.06 mmol), NMM (667 μL, 0.61 g, 6.06 mmol) and isobutyl chloroformate (786 μL, 0.83 g, 6.06 mmol) in 40 mL of THF at −15° C. After addition of diisopropylethylamine (1.06 mL, 0.78 g, 6.06 mmol), the mixture was allowed to warm to ambient temperature and to stir overnight. The reaction mixture was concentrated under reduced pressure, and the residue was taken up in ethyl acetate and washed with 1M KHSO$_4$, H$_2$O, saturated aqueous sodium bicarbonate, and brine, dried (anhydrous sodium sulfate) and evaporated to 3.8 g of light yellow solid, which was recrystallized from EtOAc/hexane to afford 3.0 g (80% yield) of the title compound as a white crystalline solid, mp 140°–141° C. $^1$H-NMR (DMSO-d$_6$): δ1.30 (s, 9H), 2.65 (dd, J$_1$=4.5 Hz, J$_2$=15 Hz, 1H), 2.82 (m, 1H), 3.02 (br d, J=16 Hz, 1H), 4.33 (m, 1H), 4.52 (m, 1H), 5.08 (d, J=5 Hz, 2H), 7.10 (m, 15H), 7.90 (d, J=7.5 Hz, 1H), 9.32 (s, 1H), 9.99 (s, 1H). MS (FAB+): m/e 619 (M+H)+, 563, 519, 429, 327. Anal. calc. for $C_{33}H_{38}N_4O_8 \cdot H_2O$: C, 62.23; H, 6.01; N, 8.80. Found: C, 62.32; H, 5.62; N, 8.65.

24c: BOC-Leu-Asp(OBn)-Phe-NHNH-CbZ

The product of Example 24b (430 mg, 0.69 mmol) was N-deprotected with 1:1 $CF_3CO_2H/CH_2Cl_2$ for 1 hour. After evaporation of the volatile components, the residue was taken up in diethyl ether and treated with 4N HCl/dioxane to precipitate 246 mg of the product as the hydrochloride salt. A solution of 203 mg (0.36 mmol) of the above salt in 2 mL of DMF at 0° C. was treated with BOC-Leu-N-hydroxysuccinimide ester (148 mg, 0.47 mmol) and diisopropylethylamine (69 μL, 51 mg, 0.40 mmol), then the mixture was allowed to warm to ambient temperature and to stir for 12 hours. The solution was concentrated, then diluted with ethyl acetate and washed with 1M $KHSO_4$, $H_2O$, saturated aqueous sodium bicarbonate, and brine, dried (anhydrous sodium sulfate) and evaporated to 270 mg of yellow solid. Trituration with diethyl ether afforded 191 mg (73% yield) of the title compound as a white solid, mp 122.5°–124.5° C. $^1$H-NMR (DMSO-d$_6$) δ0.85 (m, 6H), 1.35 (m, 11H, includes 1.35, s, 9H), 1.57 (m, 1H), 2.55 (m, 1H), 2.78 (m, 2H), 3.0 (m, 1H), 3.9 (m, 1H), 4.48 (m, 1H), 4.65 (m, 1H), 5.07 (s, 2H), 5.08 (s, 2H), 6.90 (d, J=9 Hz, 1H), 7.15–7.43 (m, 15 H), 8.05 (m, 2H), 9.32 (s, 1H), 9.94 (s, 1H). MS (FAB+): 754 (M+Na)+, 732 (M+H)+, 632, 566, 542, 510, 363, 319.

24d: Ctp-Leu-Asp-Phe-NHNH$_2$

To a solution of HCl·H-Leu-Asp(OBn)-Phe-NHNH-CbZ (100 mg, 0.15 mmol) obtained by deprotection of the product of Example 24c with HCl/dioxane in the usual manner, Ctp-OH (38 mg, 0.15 mmol), and NMM (20 μL, 18 mg, 0.18 mmol) in 2 mL of DMF at 0° C. under nitrogen was added diphenylphosphoryl azide (DPPA) (39 μL, 50 mg, 0.18 mmol). The reaction was allowed to proceed for 18 hours at 0° C. and at room temperature for 2.5 days. Additional DPPA and NMM were added in aliquots until consumption of the amine component was complete, whereupon the product was precipitated by addition of water, and collected by filtration to afford 120 mg of tan powder. The crude product was chromatographed over silica gel eluting with MeOH/CHCl$_3$ (3:97, then 5:95) to provide 75 mg (60% yield) of product. MS (FAB+): m/e 880 (M+Na)+, 858 (M+H)+. A total of 57 mg of the above material in 2 mL of DMF was stirred with 25 mg of 5% Pd on BaSO$_4$ under a hydrogen atmosphere for 1.5 hour at ambient temperature, then the mixture was filtered and concentrated. The crude product was purified by preparative HPLC (Dynamax C$_{18}$, elution with CH$_3$CN/0.05% aq. NH$_3$ in a linear gradient from 10% to 40% CH$_3$CN over 30 min.) Combination and lyophilization of fractions judged pure by analytical HPLC afforded 11 mg of the title compound, mp ca. 205° C. (dec). $^1$H-NMR (DMSO-d$_6$) δ0.85 (t, J=7 Hz, 6H), 1.45 (m, 2H), 1.62 (m, 1H), 2.4 (m, obscured by solvent), 2.8 (dd, J=9 Hz and 15 Hz, 1H), 2.95 (m), 3.0–3.7 [obscured by HDO, spectrum rerun in presence of DCl shows for this region 2.7 (dd, J=6 and 18 Hz, 1H), 2.90 (m, 1H), 2.98 (m, 1H), 3.25 (m, 1H), 3.37 (m, 1H)], 4.20 (m, 2H), 4.33 (m, 1H), 4.47 (m, 1H), 6.75 (d, J=7.5 Hz, 1H), 6.90–7.05 (m, 3H), 7.10–7.30 (m, 8H), 8.05–8.30 (m, 3H, includes 8.04, d, J=7.5 Hz), 9.22 (s, 1H), 10.94 (s, 1H). MS (FAB+): m/e 634 (M+H)+, 602, 455, 340, 227.

EXAMPLE 25

BOC-Trp-Leu-Asp-Trp-NH$_2$

BOC-Trp-Leu-Asp(β-phenacyl)-Phe-O-polystyrene resin was assembled using a Biosearch SAM 2 automatic solid phase peptide synthesizer starting with 1.50 g of BOC-Trp-O-resin (0.26 mmol/g, 1% crosslinked polystyrene, 200–400 mesh) using the following protocol: two cycles of deblock (CF$_3$CO$_2$H/CH$_2$Cl$_2$/anisole/dimethyl phosphite, 50: 45.5: 2.5: 2); two cycles of alternating methylene chloride wash and DMF wash; two cycles of base wash (10% diisopropylethylamine in methylene chloride); single 1 hour coupling of BOC-amino acid (3.5 fold excess, concentration 0.4M in CH$_2$Cl$_2$), activated by in-line mixing with an equimolar quantity of 0.4M diisopropylcarbodiimide in DMF; capping step with 0.3M acetylimidazole in DMF. All reagents and materials were commercially available except BOC-Asp(β-phenacyl)-OH (Yang, C. C. and Merrifield, R. B. *J. Org. Chem.* 1976, 41:1032–1041). The crude peptide resin was gently rotated in the presence of 10 mL of 2M benzeneselenol in DMF for 72 hours under nitrogen atmosphere then the resin was filtered and washed three times with fresh portions of DMF, three times with CH$_2$Cl$_2$, then dried under reduced pressure. Using a pressure vessel, the peptide was cleaved from the resin by ammonolysis at room temperature for 72 hours with 2,2,2-trifluoroethanol saturated at −20° C. with gaseous ammonia, to afford 59 mg of crude peptide. The recovered resin was resubjected to the above conditions to provide an additional 62 mg of crude peptide. The combined fractions of crude peptide were purified by preparative HPLC (Dynamax C$_{18}$, elution with CH$_3$CN/0.1% aq. NH$_3$, gradient from 10% to 40% CH$_3$CN over 30 min). Pure fractions were combined and lyophilized to afford 69 mg of pure product, mp 186°–191° C. $^1$H-NMR (DMSO-d$_6$): δ0.82 (t, J=7 Hz, 6H), 1.15 (br s), 1.3 (s, 9H), 1.4 (m, 2H), 1.6 (m, 1H), 2.41 (dd, J=6 Hz and 16 Hz, 1H), 2.56, (partially obscured by solvent peak), 2.84–3.2 (m, 6H), 4.21 (m, 1H), 4.35 (m, 2H), 4.47 (m, 1H), 6.73 (d, J=8 Hz, 1H), 6.95 (t, J=7.5 Hz, 2H), 7.0–7.5 (m, 5H), 7.30 (d, J=8 Hz, 2H), 7.45 (br s, 1H), 7.55 (d, J=8 Hz, 1H), 7.58 (d, J=8 Hz, 1H), 7.98 (d, J=8 Hz, 1H), 8.10, (br d, J=7.5 Hz, 1H), 8.26 (d, J=8 Hz, 1H), 10.77 (s, 1H), 10.92 (s, 1H). MS (FAB): m/e 716 (M-H)−, 642, 586, 412, 341. Amino acid analysis (hydrolysis in presence of thioglycolic acid): Leu, 1.0; Trp, 1.76; Asp, 0.81.

EXAMPLE 26

BOC-Trp-Leu-Asp-β-Nal-NH$_2$

26a: BOC-β-Nal-NH$_2$

The product was prepared in 96% yield by reaction of the mixed anhydride from BOC-β-Nal-OH (682 mg, 2.17 mmol) with conc. NH$_4$OH according to the procedure of Rzeszotarska, B., Makowski, M., and Kubica, Z. *Org. Prep. Proc. Int.*1984, 16:136–139. $^1$H-NMR (CDCl$_3$): δ1.40 (s, 9H), 3.24 (m, 2H), 4.47 (m, 1H), 5.10 (br s, 1H), 5.37 (br s, 1H), 5.75 (br s, 1H), 7.49 (dd, J=2 Hz and 9 Hz, 1H), 7.47 (m, 2H), 7.69 (s, 1H), 7.80 (m, 3H). MS (DCl): m/e 315 (M+H)+, 259, 215.

26b: HCl Asp(OBn)-β-Nal-NH$_2$

The product of Example 26a (700 mg, 2.23 mmol) was N-deprotected with 4N HCl/dioxane in the usual manner. The mixed anhydride from BOC-Asp(β-OBn)-OH (720 mg, 2.23 mmol) and isobutyl chloroformate was formed at −15° C. in THF in the usual manner, then a prechilled solution of amine salt and an equimolar amount of triethylamine in DMF was added. The reaction mixture was stirred for 30 minutes at −15° C. then the cooling bath was removed and stirring was continued. After several hours, the reaction mixture was concentrated, the crude product was precipitated by addition of water and saturated aqueous $KHSO_4$ and collected by filtration, then dried under vacuum to provide 900 mg of crude product which was N-deprotected with 4N HCl/dioxane in the normal manner. Trituration of the crude salt with $Et_2O$/hexane provided the pure salt. $^1$H-NMR (DMSO-d$_6$): δ2.83 (dd, J=9 and 17 Hz, 1H), 2.99 (m, 2H), 3.22 (dd, J=4.5 and 15 Hz, 1H), 4.09 (dd, J=3 and 11 Hz, 1H), 4.58 (m, 1H), 5.15 (d, J=2 Hz, 2H), 7.20 (s, 1H), 7.39 (m, 4H), 7.48 (m, 3H), 7.61 (s, 1H), 7.75 (s, 1H), 7.85 (m, 3H), 8.12 (br s, 3H), 8.73 (d, J=9 Hz, 1H). MS (DCI): m/e 420 (M+H)$^+$, 329, 312, 286, 260, 243, 217, 195, 178.

26c: BOC-Trp-Leu-Asp(OBn)-β-Nal-NH$_2$

The mixed anhydride from BOC-Trp-Leu-OH (459 mg, 1.1 mmol) and isobutyl chloroformate was formed at −15° C. in THF in the usual manner, then a prechilled solution of the product of Example 26b (500 mg, 1.1 mmol) and an equimolar amount of triethylamine in DMF was added. The reaction mixture was stirred for 30 minutes at −15° C., then the cooling bath was removed and stirring was continued for 1 hour. The reaction mixture was concentrated, then partitioned between ethyl acetate and dilute aqueous $KHSO_4$. The separated aqueous phase was extracted with a fresh portion of ethyl acetate, then the combined organic extracts were washed with water, saturated aqueous sodium bicarbonate, water, and brine, then dried (anhydrous sodium sulfate), filtered and evaporated to afford 770 mg of crude product. Recrystallization from EtOH/H$_2$O provided 660 mg (73% yield) of the title compound. $^1$H-NMR (DMSO-d$_6$): δ0.81 (m, 6H), 1.12 (br s), 1.29 (s, 9H), 1.39 (m, 2H), 1.60 (m, 1H), 2.62 (dd, J=8 and 17 Hz, 1H), 2.80 (dd, J=7 Hz and 16 Hz, 1H), 2.90 (dd, J=10 and 14 Hz, 1H), 3.05 (m, 2H), 3.17 (dd, J=4 and 17 Hz), 4.22 (m, 1H), 4.32 (m, 1H), 4.48 (m, 1H), 4.61 (m, 1H), 5.06 (s, 2H), 6.87 (d, J=8 Hz, 1H), 6.93 (t, J=8 Hz, 1H), 7.04 (t, J=7 Hz, 1H), 7.12 (s, 1H), 7.18 (s, 1H), 7.33 (m, 9H), 7.45 (m, 2H), 7.58 (d, J=7.5 Hz, 1H), 7.69 (s, 1H), 7.79 (d, J=9 Hz, 1H), 7.83 (m, 1H), 7.90 (d, J=8 Hz, 1H), 7.95 (d, J=8 Hz, 1H), 8.33 (d, J=7.5 Hz, 1H), 10.79 (s, 1H). MS (FAB+): m/e 831, 819 (M+H)$^+$, 803, 746, 719, 701, 505, 420, 375, 344, 300.

26d: BOC-Trp-Leu-Asp-β-Nal-NH$_2$

The product of Example 26c (300 mg, 0.37 mmol) in DMF was stirred under a hydrogen atmosphere in the presence of 75 mg of 5% Pd-C until disappearance of starting material was complete by TLC. The catalyst was removed by filtration, and the filtrate was concentrated. The residue was twice chromatographed over silica gel, eluting with 9:1 EtOAc/S2 (S2=8:1:1 MeOH/HOAc/H$_2$O), pure fractions were combined and concentrated to a small volume of glacial acetic acid, then water was added to precipitate 105 mg of the product, mp 205° C. (dec). $^1$H-NMR (DMSO-d$_6$) δ0.80 (m, 6H), 1.23–1.50 (m, 11H, includes 1.30, s, 9H), 1.57 (m, 1H), 2.50 (1H, obscured by solvent), 2.67 (dd, J=7.5 and 13.5 Hz, 1H), 2.90 (m, 1H), 3.11 (m, 2H), 3.20 (dd, J=4 and 11.5 Hz, 1H), 4.21 (m, 1H), 4.33 (m, 1H), 4.50 (m, 2H), 6.81 (d, J=2.5 Hz, 1H), 6.95 (t, J=6 Hz, 1H), 7.04 (t, J=6 Hz, 1H), 7.10 (s, 1H), 7.17 (s, 1H), 7.31 (m, 2H), 7.38 (d, J=7 Hz, 1H), 7.45 (m, 3H), 7.57 (d, J=7 Hz, 1H), 7.70 (s, 1H), 7.78 (d, J=7 Hz, 1H), 7.84 (m, 2H), 7.90 (m, 1H), 8.29 (m, 1H), 10.76 (s, 1H), 12.4 (br s, 1H). MS (DCI): m/e 729 (M+H)$^+$, 712, 685, 629, 611, 430. Anal. calc. for $C_{39}H_{48}N_6O_8$.0.3 HOAc: C, 6 6.77; N, 10.90.

EXAMPLE 27

BOC-Trp-Leu-Asp-α-Nal-NH$_2$

27a: BOC-α-Nal-NH$_2$

In the same manner as that described in Example 26a the title compound was prepared from BOC-(β-1-naphthyl)alanine (682 mg, 2.17 mmol) in 98% yield. $^1$H-NMR (CDCl$_3$) δ1.40 (s, 9H), 3.52 (m, 2H), 4.52 (m, 1H), 5.20 (br s, 1H), 5.26 (br s, 1H), 5.46 (br s, 1H), 7.38 (m, 2H), 7.55 (m, 2H), 7.28 (d, J=8 Hz, 1H), 7.38 (d, J=8 Hz, 1H), 8.20 (d, J=8 Hz, 1H). MS (DCI): 315 (M+H)$^+$, 215.

27b: CF$_3$COOH.Asp(OBn)-α-Nal-NH$_2$

In the same manner as that described in Example 26b the product of Example 27a (700 mg, 2.23 mmol) was deprotected and coupled to BOC-Asp(β-OBn)-OH to afford 950 mg of crude protected dipeptide, which was N-deprotected with 1:1 CF$_3$CO$_2$H/CH$_2$Cl$_2$ to provide the title salt. $^1$H-NMR (DMSO-d$_6$) δ2.83 (dd, J=9 and 18 Hz, 1H), 3.03 (dd, J=4 and 17 Hz, 1H), 3.27 (dd, J=10 and 15 Hz, 1H), 3.53 (dd, J=6 and 14 Hz), 4.09 (dd, J=4 and 9 Hz, 1H), 4.61 (m, 1H), 5.16 (d, J=2 Hz, 2H), 7.22 (s, 1H), 7.40 (m, 6H), 7.55 (m, 3H), 7.82 (d, J=7.5 Hz, 1H), 7.93 (d, J=7.5 Hz, 1H), 8.15 (br s, 3H), 8.29 (d, J=8 Hz, 1H), 8.82 (d, J=8 Hz, 1H). MS (DCI): m/e 420 (M+H)$^+$, 329, 312, 286, 260, 243, 217, 195, 178.

27c: BOC-Trp-Leu-Asp(OBn)-α-Nal-NH$_2$

In the same manner as described in Example 26c the product of Example 27b (1.1 mmol) was converted to the title compound. Upon treatment of the concentrated reaction mixture with water and saturated aqueous $KHSO_4$, the product precipitated as a solid (750 mg) and was recrystallized to afford 630 mg (70% yield) of the title compound. $^1$H-NMR (DMSO-d$_6$) δ0.83 (m, 6H), 1.29 (s, 9H), 1.40 (m, 2H), 1.62 (m, 1H), 2.61 (dd, J=8 and 16 Hz, 1H), 2.80 (dd, J=5 and 16 Hz, 1H), 2.90 (dd, J=4 and 15 Hz, 1H), 3.25 (m, 1H), 3.51 (m, 1H), 4.20 (m, 1H), 4.32 (m, 1H), 4.50 (m, 1H), 4.60 (m, 1H), 5.07 (s, 2H), 6.86 (d, J=8 Hz, 1H), 6.93 (t, J=7.5 Hz, 1H), 7.03 (t, J=7 Hz, 1H), 7.11 (br s, 1H), 7.20 (br s, 1H), 7.25–7.40 (m, 9H), 7.48–7.61 (m, 3H), 7.77 (d, J=8 Hz, 1), 7.93 (m, 2H), 8.06 (d, J=8 Hz, 1H), 8.20 (d, J=8 Hz, 1H), 8.31 (d, J=8 Hz, 1H), 10.79 (s, 1H). MS (FAB+): m/e 831, 819 (M+H)$^+$, 803, 746, 719, 701, 505, 420, 375, 344, 319, 300.

27d: BOC-Trp-Leu-Asp-α-Nal-NH$_2$

The product of Example 27c (100 mg, 0.12 mmol) was hydrogenolyzed as described in Example 26d. The crude product was purified by chromatography over silica gel, eluting with 6:1 EtOAc/S1 (S1=20:11:6 pyridine/HOAc/H$_2$O). Pure fractions were combined and concentrated to a small volume, then H$_2$O was added to precipitate 63 mg (71% yield) of the product, mp 213° C. (dec.) $^1$H-NMR (DMSO-d$_6$) δ0.84 (m, 6H), 1.30 (m, 11H, includes 1.30, s, 9H), 1.60 (m, 1H), 2.45 (1H, obscured by solvent), 2.67 (dd, J=7 and 16.5 Hz, 1H); 2.90 (m, 1H), 3.08 (dd, J=4 and 14 Hz, 1H), 3.25

(m, partially obscured by H2O), 3.59 (m, 1H), 4.20 (m, 1H), 4.32 (m, 1H), 4.48 (m, 2H), 6.82 (d, J=8 Hz, 1H), 6.95 (t, J=7.5 Hz, 1H), 7.05 (t, J=7.5 Hz, 1H), 7.10 (s, 1H), 7.23 (m, 2H), 7.30–7.41 (m, 3H), 7.48–7.61 (m, 3H), 7.77 (d, J=8 Hz, 1H), 7.90 (d, J=8 Hz, 1H), 8.08 (d, J=8 Hz, 1H), 8.21 (d, J=8 Hz, 1H), 8.27 (d, J=7.5 Hz, 1H), 10.77 (s, 1H). MS (FAB+): 729 (M+H)+, 713, 629, 611, 596. Anal. calc. for $C_{39}H_{48}N_6O_8 \cdot 0.3$ HOAc: C, 63.61, H, 6.64, N, 11.23. Found: C, 63.90, H, 6.76, N, 11.18.

EXAMPLE 28

BOC-Trp-Pro-Asp-Phe-NH2

28a: BOC-Pro-Asp(OBn)-Phe-NH2

BOC-Pro-OH (189 mg, 0.88 mmol) was coupled to TFA.Asp($\beta$-OBn)-Phe-NH2 (425 mg, 0.88 mmol) using the DCC/HOBt method in THF in the usual manner to provide after work-up 469 mg of crude product. Recrystallization from ethyl acetate provided 326 mg (65% yield) of the title compound as a white solid. $^1$H-NMR (DMSO-$d_6$) (2 conformers, 1.5:1) $\delta$1.28 (s, 5.4H), 1.38 (s, 3.6H), 1.71 (m, 3H), 2.0 (m, 1H), 2.58 (d, J=7.5 Hz, 0.4H), 2.63 (d, J=7.5 Hz, 0.6 H), 2.80 (m, 2H), 3.02 (m, 1H), 3.25 (1H, obscured by H2O), 4.05 (m, 1H), 4.39 (m, 1H), 4.60 (m, 1H), 5.07 (s, 2H), 7.20 (m, 7H), 7.35 (m, 5H), 7.74 (d, J=8 Hz, 0.4H), 7.86 (d, J=7.5 Hz, 0.6H), 8.14 (d, J=7.5 Hz, 0.6H), 8.24 (d, J=7.5 Hz, 0.4H). MS (EI): m/e 566 (M+), 522, 465, 458, 402, 385, 358, 314.

28b: BOC-Trp-Pro-Asp-Phe-NH2

The product of Example 28a was N-deprotected with 4N HCl/dioxane in the usual manner. The resulting hydrochloride salt (177 mg, 0.35 mmol) in DMF at 0° C. was neutralized with N-methylmorpholine (38 μL, 0.35 mmol), then treated with a solution of the symmetrical anhydride formed from BOC-Trp-OH (322 mg, 1.06 mmol) and DCC (109 mg, 0.53 mmol) in methylene chloride. After stirring at 0° C. for 68 hours, the mixture was treated with several drops of 1-(2-aminoethyl)piperazine, then concentrated. The residue was partitioned between ethyl acetate and dilute aqueous KHSO4, and the separated aqueous layer was extracted twice with fresh portions of ethyl acetate, then the combined organic extracts were washed with water, saturated aqueous sodium bicarbonate, water, and brine, then dried (anhydrous sodium sulfate), filtered and evaporated to 330 mg of crude product. Chromatography over silica gel, eluting with 83:17:2 EtOAc/hexane/HOAc, then 98:2 EtOAc/HOAc, afforded 281 mg of pure product which was hydrogenolyzed in MeOH over 100 mg of 20% Pd(OH)2·C for 0.5 hour. The mixture was filtered and concentrated, and the residue was chromatographed on silica gel, eluting with 85:15 EtOAc/S2 (S2=8:1: MeOH/HOAc/H2O). Pure fractions were combined and concentrated to 240 mg, which was recrystallized from EtOH/H2O to provide 174 mg of the title compound as a white solid, mp 155.5°–157° C. (dec). $^1$H-NMR (DMSO-$d_6$) (2 conformers, 4:1) major conformer: $\delta$1.30 (s, 9H), 1.7–2.1 (m, 4H), 2.48 (1H, obscured by solvent), 2.67 (dd, J=6 and 16 Hz, 1H), 2.84–3.16 (m, 4H), 3.55 (m, 2H), 4.27–4.51 (m, 4H), 6.92–7.10 (m, 3H), 7.15–7.28 (m, 7H), 7.35 (d, J=7.5 Hz, 1H), 7.52 (d, J=7.5 Hz, 1H), 7.81 (d, J=8 Hz, 1H), 8.18 (d, J=7.5 Hz, 1H), 10.83 (s, 1H). MS (FAB+): m/e 663 (M+H)+, 647, 563, 377. Anal. calc. for $C_{34}H_{42}N_6O_8 \cdot 0.5$ H2O: C, 60.78, H, 6.46, N, 12.51. Found: C, 60.90, H, 6.44, N, 12.46.

EXAMPLE 29

BOC-Trp-Tpp-Asp-Phe-NH2

29a: BOC-Tpp-Asp(OBn)-Phe-NH2

BOC-Tpp-OH (65 mg, 0.25 mmol), the product of Example 34 g, was coupled to TFA.Asp(OBn)-Phe-NH2 (244 mg, 0.5 mmol) by the DCC/HOBt procedure in THF in the usual manner. On completion of the reaction, the mixture was treated with several drops of saturated aqueous KHSO4, filtered, and the filtrate was diluted with ethyl acetate and washed with saturated aqueous KHSO4, H2O, saturated aqueous NaHCO3, H2O, and brine, then dried (Na2SO4), filtered and evaporated to provide 180 mg of crude product. The product was purified on silica gel (chromatotron, 1 mm plate) eluting with 2% MeOH/CHCl3 to provide 105 mg (72% yield) of pure title compound. $^1$H-NMR (CDCl3) $\delta$0.93 (t, J=7 Hz, 3H), 1.24–1.6 (m, 14H, includes 1.45, s, 9H), 2.0 (m, 1H), 2.19 (m, 1H), 2.75 (dd, J=6 and 18 Hz, 1H), 2.94–3.21 (m, 2H), 3.37 (m, 1H), 3.47 (dd, J=4.5 and 15 Hz, 1H), 3.58 (m, 1H), 3.77 (d, J=7 Hz, 1H), 4.57 (m, 1H), 4.75 (m, 1H), 4.91 (d, J=12 Hz, 1H), 5.08 (d, J=12 Hz, 1H), 5.30 (br s, 1H), 6.70 (br s, 1H), 7.12–7.43 (m, 10H), 7.50 (d, J=7 Hz, 1H), 7.58 (d, J=7.5 Hz, 1H), MS (DEI/DIP): m/e 609 (M+H)+, 507, 464, 445, 400, 356, 212.

29b: BOC-Trp-Tpp-Asp(OBn)-Phe-NH2

The product of Example 29a (101 mg, 0.17 mmol) was N-deprotected with 1:1 CF3CO2H/CH2Cl2 in the usual manner. The resultant salt in 3 mL of DMF at 0° C. was treated with a solution of the symmetrical anhydride prepared from BOC-Trp-OH (155 mg, 0.51 mmol) and DCC (53 mg, 0.26 mmol) in 5 mL of CH2Cl2 at 0° C., followed by addition of NEti-Pr2 (78 μL, 0.45 mmol). Solvent was removed under reduced pressure (air bath) and the solution was stirred for 1 hour at 0° C., and then allowed to warm to room temp. The solution was concentrated, and the residue was dissolved in EtOAc, then washed with saturated aqueous KHSO4, H2O, sat. aq. NaHCO3, H2O, and brine, then dried (Na2SO4), filtered and evaporated. The crude product was chromatographed over silica gel, eluting with EtOAc/hexane (10:1, then 7:1), then EtOAc, to afford 112 mg (83% yield) of pure title compound. $^1$H-NMR (CDCl3) $\delta$0.89 (t, J=4.5 Hz, 3H), 1.15–1.35 (m, 5H), 1.41 (s, 9H, shoulder at 1.38), 1.83 (m, 1H), 1.98 (m, 1H), 2.64 (dd, J=5 and 3.5 Hz, 1H), 2.81 (dd, J=3 and 10 Hz, 1H), 2.98 (m, 1H), 3.15 (m, 3H), 3.44 (dd, J=2 and 9 Hz, 1H), 3.56 (m, 1H), 3.90 (d, J=5 Hz, 1H), 4.60 (q, J=3H, 1H), 4.70 (q, J=4 Hz, 1H), 4.75 (m, 1H), 5.02 (d, J=7.5 Hz, 1H), 5.12 (2H, includes d, J=7.5 Hz, 1H), 5.36 (s, 1H), 6.61 (s, 1H), 6.96 (m, 2H), 7.13 (t, J=4 Hz, 1H), 7.20 (m, 4H), 7.25–7.35 (m, 7H), 7.47 (d, J=5 Hz, 1H), 7.62 (d, J=5 Hz, 1H), 8.20 (s, 1H). MS (DCI): m/e 795 (M+H)+, 695, 687, 587, 569.

29c: BOC-Trp-Tpp-Asp-Phe-NH2

The product of Example 29b (105 mg, 0.13 mmol) in 1.5 mL of MeOH was stirred under a hydrogen atmosphere in the presence of 5% Pd/C for 2.5 hours, then the mixture was filtered through Celite ® and the filtrate was concentrated. The residue was chromatographed over silica gel, eluting with 9:1 EtOAc/S2 (S2=8:1:1 MeOH/HOAc/H2O) to afford 63 mg of title compound, mp 145°–147° C. $[\alpha]_D^{23} = -30.1°$ (c 0.5; DMF). $^1$H-NMR (DMSO-$d_6$): $\delta$0.85 (m, 3H), 1.05–1.40 (m, 14H, includes 1.44, s, 9H), 1.46 (m, 1H), 2.03 (m, 1H), 2.53 (1H, obscured by solvent), 2.67 (m, 1H), 2.93

(m, 2H), 3.0–3.18 (m, 2H), 3.73 (m, 1H), 3.90 (m, 1H), 4.25–4.50 (m, 4H), 6.97 (m, 1H), 7.11 (m, 2H), 7.22 (m, 8H), 7.44 (d, J=7.5 Hz, 1H), 7.50 (d, J=7.5 Hz, 1H), 7.90 (br d, J=7.5 Hz, 1H), 8.30 (d, J=7.5 Hz, 1H), 10.87 (br s, 1H). MS (FAB+): m/e 727 (M+Na)+, 705 (M+H)+,689, 605, 587, 419. Anal. calc. for $C_{37}H_{48}N_6O_8 \cdot 0.5\ H_2O$: C, 62.24; H, 6.92; N, 11.77. Found: C, 62.37; H, 6.83; N, 11.52.

EXAMPLE 30

Ctp-Tpp-Asp-Phe-NH$_2$

30a: Ctp-Tpp-Asp(OBn)-Phe-NH$_2$

The product of Example 29a (68 mg, 0.11 mmol) was N-deprotected as described in Example 29a. The resultant salt and Ctp-OH (0.12 mmol) were dissolved in 1:1 CH$_2$Cl$_2$/DMF and treated at 0° C. with diisopropylethylamine (57 μL, 0.33 mmol) and BOP-Cl (31 mg, 0.12 mmol). The solution was kept at 4° C. for 69 hours, more Bop-Cl was added, and the reaction was allowed to continue at the same temperature for an additional 48 hours, then the mixture was concentrated. The residue was dissolved in EtOAc, washed with saturated aqueous KHSO$_4$, H$_2$O, saturated aqueous NaHCO$_3$, H$_2$O, and brine, then dried (Na$_2$SO$_4$), filtered and evaporated to afford 66 mg of crude product. This material was purified by chromatography over silica gel, eluting with CHCl$_3$/MeOH (98:2, then 90:10), to afford 38 mg (47% yield) to pure title compound; HRMS Calc. for (M+H)+=C$_{41}$H$_{47}$N$_6$O$_7$: m/e 735.3506. Found: 735.3507.

30b: Ctp-Tpp-Asp-Phe-NH$_2$

The product of Example 30a (36 mg, 0.049 mmol) in methanol was stirred under an H$_2$ atmosphere in the presence of 5% Pd/BaSO$_4$ for 0.5 hour, after which TLC showed complete comsumption of starting material. The mixture was filtered through Celite®, the filtrate was concentrated, and the residue was chromatographed over silica gel, eluting with 3:1 EtOAc/S1 (S1=20:11:6 pyridine/H$_2$O/HOAc) to afford 29 mg of pure title compound, mp 192° C. (dec). $^1$H-NMR (DMSO-d$_6$) δ0.88 (m, 3H), 1.25 (m, 4H), 1.55 (br, 1H), 2.05 (m, 2H), 2.22 (m, 2H), 2.80 (dd, J=10 and 14 Hz, 1H), 3.12 (dd, J=4 and 14 Hz, 1H), 3.20–3.72 (m, 5H), 3.87 (m, 1H), 3.93 (d, J=4 Hz, 1H), 4.08 (m, 1H), 4.22 (m, 1H), 4.58 (m, 1H), 6.77 (m, 1H), 6.95 (m, 3H), 7.10–7.25 (m, 7H), 11.0 (br s, 1H). HRMS: Calc. for (M+H)+=C$_{34}$H$_{41}$N$_6$O$_7$: 645.3037. Found: 645.3036.

EXAMPLE 31

BOC-α-Nal-Leu-Asp-Phe-NH$_2$

BOC-α-Nal-OH (200 mg, 0.63 mmol) was coupled to TFA-Leu-ASp(OBn)-Phe-NH$_2$ (376 mg, 0.63 mmol) by the mixed anhydride method in the normal fashion using isobutyl chloroformate as the activating agent. Upon completion of the reaction, the mixture was concentrated, and the crude product (390 mg) was caused to precipitate by addition of dilute aqueous KHSO$_4$. A solution of 150 mg of this product in DMF was stirred under a hydrogen atmosphere in the presence of 5% Pd-C until consumption of starting material was complete by TLC. The mixture was filtered, the filtrate was concentrated, and the residue was chromatographed over silica gel, eluting with 6:1 EtOAc/S1. Pure fractions were combined and concentrated to a small volumen, then water was added and the precipitated product (120 mg) was collected by filtration and dried in vacuo, mp 231° C. (dec). $^1$H-NMR (DMSO-d$_6$) δ0.87 (m, 6H), 1.24 (s, 9H), 1.44 (m, 2H), 1.65 (m, 1H), 2.48 (1H, obscured by solvent), 2.70 (dd, J=6 and 20 Hz, 1H), 2.85 (dd, J=9 and 14 Hz, 1H), 3.05 (dd, J=4.5 and 14 Hz, 1H), 3.15 (dd, J=10 and 14 Hz, 1H), 3.53 (dd, J=4 and 14 Hz, 1H), 4.35 (m, 3H), 4.52 (m, 1H), 7.05 (d, J=9 Hz, 1H), 7.15–7.32 (m, 7H), 7.40 (m, 2H), 7.53 (m, 2H), 7.77 (m, 1H), 7.90 (m, 3H), 8.15 (d, J=8 Hz, 1H), 8.30 (d, J=7.5 Hz, 1H). MS (FAB+): m/e 690 (M+H)+, 674, 590, 307. Calc. for $C_{37}H_{47}N_5O_8 \cdot 0.5\ H_2O$: C, 63.57; H, 6.93; N, 10.03. Found: C, 63.64; H, 6.70; N, 9.69.

EXAMPLE 32

BOC-β-Nal-Leu-Asp-Phe-NH$_2$

In a procedure analogous to that described in Example 31, BOC-β-Nal-OH (200 mg, 0.63 mmol) was coupled to TFA.Leu-Asp(OBn)-Phe-NH$_2$ to afford 430 mg of curde protected peptide as a solid. Hydrogenolysis of 150 mg of this product followed by work-up and purification as in Example 32 afforded 73 mg of the title compound, m.p. 204° C. (dec). $^1$H-NMR (DMSO-d$_6$) δ0.85 (t, J=7.5 Hz, 6H), 1.25 (s, 9H), 1.40 (m, 2H), 1.63 (m, 1H), 2.43 (dd, J=7 and 17 Hz, 1H), 2.64 (dd, J=7 and 17 Hz, 1H), 2.79–2.91 (m, 2H), 3.05 (dd, J=4.5 and 14 Hz, 1H), 3.15 (dd, J=3 and 14 Hz, 1H), 4.25–4.40 (m, 3H), 4.50 (m, 1H), 6.97 (d, J=8 Hz), 7.10–7.28 (m, 6H), 7.35 (s, 1H), 7.45 (m, 3H), 7.73 (s, 1H), 7.76–7.88 (m, 3H), 7.96 (m, 2H), 8.28 (d, J=7.5 Hz, 1H). MS (FAB+): m/e 690 (M+H)+, 674, 590, 575, 307. Anal. calc. for $C_{37}H_{47}N_5O_8 \cdot H_2O$: C, 62.77; H, 6.98; N, 9.90. Found: C, 62.40; H, 6.55; N, 9.58.

EXAMPLE 33

BOC-Trp-Leu-Asp-[3(S)-benzyl-2-oxo-4-piperazine]

33a: Cbz-Phe-allylamide

Under a nitrogen atmosphere, Cbz-Phe-OH (1.00 g, 3.35 mmol) was dissolved in 10 mL of anhydrous methylene chloride containing 1-hydroxybenzotriazole monohydrate (0.57 g, 3.69 mmol) and 1-(3-dimethylaminopropyl)-ethylcarbodiimide hydrochloride (0.71 g, 3.69 mmol) and stirred at ice bath temperature for 1.5 hour. Allylamine (0.19 g, 3.35 mmol) was added and the solution was stirred at 0° C. for 5 hours and then allowed to warm to ambient temperature overnight. The solvent was evaporated, and the residue was dissolved in ethyl acetate and washed with saturated aqueous KHSO$_4$, water, saturated aqueous sodium bicarbonate, water, and brine, prior to drying and evaporation. Recrystallization from ethyl acetate/hexane afforded 0.56 g (50% yield) of the title compound as a white solid product; $^1$H NMR (CDCl$_3$) δ3.03 (dd, J=15 and 7.5 Hz, 1H), 3.14 (dd, J=15 and 7.5 Hz, 1H), 3.76–3.82 (m, 2H), 4.33–4.42 (m, 1H), 4.96–5.08 (m, 2H), 5.10 (s, 2H), 5.33 (br s, 1H), 5.59–5.74 (m, 2H), 7.15–7.40 (m, 10H). MS (DCI) m/e 356 (M+NH$_4$)+, 339 (M+H)+.

33b: 3(S)-benzyl-4-benzyloxycarbonyl-5-hydroxy-2-oxo-4-piperazine

To a stirred solution of the product of Example 33a (376 mg, 1.1 mmol) in 27 mL of CH$_3$CN/H$_2$O (2:1) at room temperature was added 4-methylmorpholine N-oxide (180 mg, 1.3 mmol) and osmium tetroxide (2.5% in t-butanol, 2.9 mg, 0.01 mmol). After 5 minutes, sodium periodate (949 mg, 4.4 mmol) was added and the mixture was stirred at room temperature for 3.5 hours. The acetonitrile was removed in vacuo and the resulting aqueous solution was extracted with ethyl acetate.

The separated organic phase was washed with saturated aqueous KHSO$_4$, H$_2$O, saturated aqueous NaHCO$_3$, H$_2$O, and brine prior to drying. After solvent evaporation, the crude material was purified by flash chromatography over silica gel, eluting with 2% methanol/chloroform to afford 212 mg (56% yield) of the desired lactol: $^1$H NMR (CDCl$_3$) δ3.02–3.17 (m, 2H), 4.06–4.19 (m, 2H), 4.43–4.55 (m, 1H), 5.09 (s, 2H), 5.30 (br s, 1H), 6.47 (br s, 1H), 7.16–7.39 (m, 10H), MS (DCI): m/e 358 (M+NH$_4$)+, 341 (M+H)+, 316, 299.

33c: 3(S)-benzyl-2-oxopiperazine

The product of Example 33b (183 mg, 0.54 mmol) in methanol was stirred under a hydrogen atmosphere (4 atm) in the presence of 10% palladium on activated carbon (183 mg) at ambient temperature overnight. Removal of the catalyst by filtration followed by solvent evaporation gave 77 mg (75%) of crude product. Purification by flash chromatography on silica gel eluting with 3% MeOH/CHCl$_3$ afforded 26 mg (25%) of the title compound; $^1$H NMR (DMSO-d$_6$) δ1.24 (br s, 1H), 2.61–3.21 (m, 6H), 4.03–4.07 (m, 1H), 7.13–7.32 (m, 5H), 7.64 (br s, 1H). MS (DCI): m/e 208 (M+NH$_4$)+, 191 (M+H)+

33d: BOC-Asp(OBn)-[3(S)-benzyl-2-oxo-4-piperazine]

A solution of BOC-ASp(OBn)-OH (476 mg, 1.47 mmol) in 4 mL of anhydrous methylene chloride under a nitrogen atmosphere was cooled to ice bath temperature and 1-(3-dimethylaminopropyl)-3-ethylcarbodiimide hydrochloride (142 mg, 0.74 mmol) was added. After 40 minutes the solution was added directly to a pre-cooled solution of the product of Example 33c (128 mg, 0.67 mmol) in 2 mL of anhydrous DMF at ice bath temperature. The reaction mixture was stirred at 0° C. for 3 hours and at ambient temperature for 48 hours. The solvents were removed in vacuo, then the residue was dissolved in ethyl acetate and washed with saturated aqueous KHSO$_4$, water, saturated aqueous NaHCO$_3$, water, and brine. After drying and solvent evaporation, the crude material was purified by flash chromatography on silica gel eluted with 43% acetone/hexane affording 213 mg (64% yield) of title compound: $^1$H NMR (CDCl$_3$) δ3.02–3.17 (m, 2H), 4.06–4.19 (m, 2H), 4.43–4.55 (m, 1H), 5.09 (s, 2H), 5.30 (br s, 1H), 6.47 (br s, 1H), 7.16–7.39 (m, 10H). MS (DCI): m/e 358 (M+NH$_4$)+, 341 (M+H)+316, 299.

33e: BOC-Leu-Asp(OBn)-[3(S)-benzyl-2-oxo-4-piperazine]

The product of Example 33d (182 mg, 0.37 mmol) was treated with a solution of 4.5M HCl/dioxane (3 mL) for 1 hour at ambient temperature after which the solvent was removed in vacuo to give a foamy residue. Diethyl ether was repeatedly added to the residue and evaporated, leaving the deprotected dipeptide as a tan solid which has then employed in the subsequent coupling step without purification. A solution of BOC-Leu-OH monohydrate (203 mg, 0.81 mmol) in 3 mL of anhydrous 1:10 DMF/CH$_2$Cl$_2$ under a nitrogen atmosphere was cooled in an ice bath and EDCI was added. After 40 minutes the solution was added directly to a pre-cooled solution of the above hydrochloride salt (160 mg, 0.37 mmol) in 1 mL of anhydrous DMF at ice bath temperature. Triethylamine (0.052 mL, 0.37 mmol) was then added and the reaction was stirred for 3 h at 0° C. and allowed to warm to room temperature overnight. The solvents were removed in vacuo and the residue was dissolved in ethyl acetate and washed with saturated aqueous KHSO$_4$, H$_2$O, saturated aqueous NaHCO$_3$, H$_2$O, and brine. After drying and solvent evaporation the crude material was purified by flash chromatography on silica gel eluting with 3% MeOH/CHCl$_3$ to afford 195 mg (86%) of the protected tripeptide: $^1$H NMR (CDCl$_3$) δ0.85–1.00 (m, 6H), 1.46 (s, 9H), 1.57–1.60 (m, 2H), 2.55–2.67 (m, 2H), 2.89–3.00 (m, 2H), 3.09–3.50 (m, 4H), 3.62–3.90 (m, 2H), 4.11 (br s, 1H), 4.99–5.26 (m, 3H), 5.86–6.00 (m, 6.85 (br s, 1H), 7.12–7.40 (m, 10H). MS (DCI): m/e 626 (M+NH$_4$)+, 609 (M+H)+, 509, 419, 381, 231, 131.

33f: BOC-Trp-Leu-Asp(OBn)-[3(S)-benzyl-2-oxo-4-piperazine]

The product of Example 33e (173 mg, 0.28 mmol) was deprotected with 4N HCl/dioxane in the usual manner. To a stirred solution of the resulting salt (152 mg, 0.28 mmol) in 1.8 mL of anhydrous DMF under a nitrogen atmosphere at ambient temperature was added N,N-diisopropylethylamine (0.049 mL, 0.28 mmol) and BOC-Trp-N-hydroxysuccinimide ester (124 mg, 0.31 mmol). The mixture was stirred for 48 hours, then the solvent was evaporated and the residue was dissolved in ethyl acetate and washed with saturated potassium hydrogen sulfate solution, water, saturated sodium bicarbonate solution, and brine. After drying and solvent evaporation, the crude material was purified by flash chromatography on silica gel eluting with acetic acid/ethyl acetate/hexane (3:25:72, then 3:50:47) to afford 188 mg (84%) of the peptide: $^1$H NMR (CDCl$_3$) δ0.74–0.89 (m, 6H), 1.45 (s, 9H), 1.57–1.78 (m, 3H), 2.66–3.53 (m, 10H), 3.88–3.99 (m, 1H), 4.18–4.60 (m, 3H), 4.94–5.28 (m, 3H), 5.84–5.91 (m, 1H), 6.02–6.18 (m, 1H), 6.42–6.49 (m, 1H), 7.07–7.43 (m, 14H), 7.65–7.72 (m, 1H), 8.67–8.80 (m, 1H). MS (FAB+): m/e, 795 (M+H)+, 779, 695, 678, 605, 505, 489, 396.

33g: BOC-Trp-Leu-Asp-[3(S)-benzyl-2-oxo-4-piperazine]

To a stirred suspension of 10% of Pd-C (32 mg) at ambient temperature in 3 mL of 10% formic acid/methanol under nitrogen atmosphere was added the product of Example 33f (76 mg, 0.096 mmol). After 24 hours, the mixture was filtered using methanol to rinse. The crude material was subjected to flash chramotography (elution with 9:1 EtOAc/S1 followed by RP-HPLC purification (flow rate 14 mL/min, linear gradient from 20 to 55% CH$_3$CN/H$_2$O over 40 min). The pure fractions were combined and lyophylized twice, yielding 13 mg (19% yield) of pure title compound isolated as the trihydrate. $^1$H NMR (DMSO-d$_6$) δ0.78–0.95 (m, 6H), 1.12–1.72 (m, 3H), 2.19–3.30 (m, 10H), 3.79–3.90 (m, 1H), 4.12–4.52 (m, 3H), 4.69–4.76 (m, 1H), 4.86–5.05 (m, 1H), 6.72 (br s, 1H), 6.92–7.34 (m, 8H), 7.53–7.62 (m, 1H), 7.88–7.98 (m, 1H), 8.08 (br s, 1H), 8.47–8.62 (m, 1H), 10.82–10.97 (m, 1H). MS (FAB+): m/e 705 (M+1)+, 605, 185, 130, 93. Anal. calcd. for C$_{37}$H$_{48}$N$_6$O$_8$.3 H$_2$O: C, 58.52; H, 7.17; N, 11.07. Found: C, 58.49; H, 6.52; N, 10.90; [α]$^D$24.5=+8.57° C. (c 0.105; MeOH).

EXAMPLE 34

Ctp-Tpp-Asp-(NMe)Phe-NH$_2$

34a: Diethyl 1-Acetyl-5-hydroxy-3-n-propylpyrrolidine-2,2-dicarboxylate

Sodium metal (3.48 g, 0.15 mol) was dissolved in a stirred solution of diethyl acetamidomalonate (201.6 g, 0.93 mol) in anhydrous ethanol (1200 mL) at room temperature under nitrogen. The reaction mixture was cooled to 0° C. and trans-2-hexenal (100.0 g, 1.02 mol)

was then added dropwise. The resulting mixture was allowed to warm to room temperature. After stirring for 3 hours at 23° C., the reaction was quenched with 24 mL of acetic acid. The solution was concentrated in vacuo and the resulting residue was taken up in ethyl acetate and washed with saturated aqueous NaHCO$_3$ (2×) and brine. Dried over anhydrous magnesium sulfate, concentation and recrystallization of the residue from EtOAc/Hexane gave 271.4 g (93% yield) of the title compound as fine needles, mp 105°–106° C. TLC, R$_f$=0.43 (9:1 CHCl$_3$/MeOH). MS(CI) m/e 316 (M+1)$^+$, 298 (MH-H$_2$O)$^+$. $^1$H NMR (CD$_3$OD, 300 MHz) δ0.94 (t, J=7.2 Hz, 3H), 1.47–1.11 (m, 9H), 1.90–1.78 (m, 1H), 1.94 (dd, J=12.8, 5.2 Hz, 1H), 2.08 (dd, J=12.8, 6.4 Hz, 1H), 2.21 (s, 3H), 2.83 (m, 1H), 4.10–4.26 (m, 4H), 5.64 (d, J=5.2 Hz, 1H). IR (CDCl$_3$) 3460, 1750, 1665 cm$^{-1}$. Anal. calcd. for C$_{15}$H$_{25}$NO$_6$: C, 57.13; H, 7.99; N, 4.44. Found: C, 57.28; H, 8.08; N, 4.42.

34b: Diethyl 1-Acetyl-3-n-propylpyrrolidine-2,2-dicarboxylate

To a solution of diethyl 1-acetyl-5-hydroxy-3-propyl-pyrrolidine-2,2-dicarboxylate (271.0 g, 0.86 mol) and triethylsilane (206 mL, 1.29 mol) in methylene chloride (3 L) was added trifluoroacetic acid (TFA) (663 mL, 8.6 mol) dropwise with stirring while controlling the internal temperature at 25°–30° C. by means of an acid bath. After stirring for 3 hours at 23° C., the solution was concentrated in vacuo and the residue was diluted with CH$_2$Cl$_2$ and washed with saturated aqueous sodium bicarbonate solution until all the TFA was neutralized. The organic phase was dried (anhydrous sodium sulfate) and concentrated to give 350 g of oil. The oily product containing silicon impurities was used directly in the subsequent step. An analytically pure sample of the title compound was obtained as an oil after flash chromatography (1:2→1:1 EtOAc/hexane). TLC, R$_f$=0.55 (9:1 CHCl$_3$/MeOH). MS(CI) m/e 300 (M+H)$^+$. IR (CDCl$_3$) 1745, 1655 cm$^{-1}$. $^1$H NMR (CDCl$_3$, 300 MHz) δ0.89–93 (t, J=7.0 Hz, 3H), 1.15–1.42 (m, 9H), 1.70–1.85 (m, 2H), 2.01–2.16 (m, 4H), 2.40–2.51 (m, 1H), 3.57 (ddd, J=10.7, 9.6, 6.2 Hz, 1H), 3.76 ('dt', J=9.6, 1.1 Hz, 1H), 4.17–4.28 (m, 4H). Anal. calcd. for C$_{15}$H$_{25}$NO$_5$: C, 60.18; H, 8.42; N, 4.68. Found: C, 59.90; H, 8.34; N, 4.65.

34c: Trans- and cis-3-n-propylproline hydrochlorides

The crude ester of Example 34b (350 g) was suspended in 6N HCl (2 L) and acetic acid (500 mL) and heated at reflux for 17 hours. The reaction mixture was extracted with EtOAc (2×) and the aqueous phase was concentrated on a rotary evaporator. The residue was then triturated with ether to crystallize the product. The solid was collected by filtration, washed with ether and dried in a vacuum oven to give 152.3 g of the hydrochloride salt. An analytically pure sample of the title compound was obtained by recrystallization from acetone/ether, mp 131°–133° C. TLC, R$_f$=0.26 (10:4:1 CHCl$_3$/MeOH/NH$_4$OH). IR (KBr) 3420, 1735 cm$^{-1}$. MS(CI) m/e 158 (free base MH+). $^1$H NMR (D$_2$O, 300 MHz) major isomer δ0.91 (t, J=7.2 Hz, 3H), 1.18–1.50 (m, 3H), 1.68–1.90 (m, 2H), 2.16–2.32 (m, 1H), 2.43–2.50 (m, 1H), 3.29–3.58 (m, 2H), 3.93 (d, J=7.4 Hz, 1H); Minor isomer: d 0.89 (t, J=6.8 Hz, 3H), 1.18–1.50 (m, 3H), 1.68–1.90 (m, 2H), 2.16–2.32 (m, 1H), 2.60–2.66 (m, 1H), 3.29–3.58 (m, 2H), 4.32 (d, J=8.1 Hz, 1H). Anal. calcd. for C$_8$H$_{16}$NO$_2$Cl: C, 49.61; H, 8.33; N, 7.23. Found: C, 49.35; H, 8.17; N, 7.18.

34d: Methyl N-tert-butoxycarbonyl-3-n-propylproline

The hydrochloride salt of Example 34c (152.3 g) was dissolved in methanol (1.5 L) and the solution was charged with hydrogen chloride gas until it was saturated. After stirring overnight, the reaction mixture was concentrated to give an oil. This was taken up in 1N HCl and extracted with ethyl acetate (2×). The aqueous layer was carefully made basic with potassium carbonate and extracted with chloroform exhaustively. The combined organic phases were dried (magnesium sulfate), filtered and concentrated to give 122 g of oil. TLC, R$_f$=0.70 (90:10:01 CHCl$_3$/MeOH/NH$_4$OH). MS (CI) m/e 272 (M+H)$^+$. Partial $^1$H NMR (CDCl$_3$, 300 MHz) Major isomer: δ3.36 (d, J=6.3 Hz, 1H), 3.74 (s, 3H). Minor isomer: d 3.72 (s, 3H), 3.83 (d, J=8.1 Hz, 1H). The oil (122 g) was taken up in MeOH (1 L) and then NaHCO$_3$ (180 g) and di-t-butyl-dicarbonate (171.4 g, 0.79 mol) were added slowly. After stirring overnight at 23° C., the mixture was filtered and the filtrate concentrated. The residue was triturated with ethyl acetate, filtered again and concentrated to give 186.1 g of the title compound as an oil and as a mixture of cis and trans isomers. TLC, R$_f$=0.31 (1:6 EtOAc/hexane). IR (CDCl$_3$) 1700, 1745 cm$^{-1}$. MS(CI) m/e 272 (M+H)$^+$. Partial $^1$H NMR (CDCl$_3$, 300 MHz) cis isomer (2 conformers) δ0.91 (t, J=7.0 Hz, 3H), 3.71 (s, 1.8 H), 3.72 (s, 1.2H), 4.23 (d, J=8.5 Hz, 0.6H), 4.32 (d, J=8.1 Hz, 0.4H); trans isomer (2 conformers) δ0.92 (t, J=7.0 Hz, 3H), 1.06–1.78 (m, 14H), 1.92–2.03 (m, 1H), 2.13–2.25 (m, 1H), 3.42–3.50 (m, 1H), 3.56–3.68 (m, 1H), 3.73 (s, 1.8H), 3.74 (s, 1.2H), 3.81 (d, J=6.2 Hz, 0.6H), 3.94 (d, J=5.5 Hz, 0.4H). Anal. calcd for C$_{14}$H$_{25}$NO$_4$: C, 61.97; H, 9.29; N, 5.16. Found: C, 61.93; H, 9.30; N, 5.11.

34e: N-t-BOC-trans-3-n-propylproline and Methyl N-t-BOC-cis-3-n-propylproline

To a solution of the esters of Example 34d (186.0 g, 0.685 mol), in MeOH (685 mL) was added 1N NaOH (685 mL) at 23° C. After stirring for 20 hours, the solution was concentrated to remove methanol and then extracted with ethyl acetate (3×). The extracts were dried (MgSO$_4$), filtered and concentrated to give 71.4 g (38% yeild) of cis ester. TLC, R$_f$=0.54 (1:4 EtOAc/hexane). IR (CDCl$_3$) 1745, 1700 cm$^{-1}$. High resolution MS(CI) m/e 272.1869 ((M+H)$^+$, for C$_{14}$H$_{26}$NO$_4$, calcd 272.1862). $^1$H NMR (CDCl$_3$, 300 MHz) cis isomer (2 conformers) δ0.91 (t, J=7.0 Hz, 3H), 1.07–1.20 (m, 1H), 1.23–1.45 (m, 12H), 1.64–1.78 (m, 1H), 1.90–2.12 (m, 1H), 2.25–2.41 (m, 1H), 3.25–3.34 (m, 1H), 3.56–3.68 (m, 1H), 3.71 (s, 1.8H), 3.72 (s, 1.2H), 4.23 (d, J=8.5 Hz, 0.6H), 4.32 (d, J=8.1 Hz, 0.4H). The aqueous phase was acidified with solid citric acid and extracted twice with ethyl acetate. The combined extract was washed with water and brine, dried (magnesium sulfate), filtered and concentrated to 94.2 g (53% yield) of trans acid. TLC, R$_f$=0.45 (9:1 CHCl$_3$/MeOH). IR (CDCl$_3$) 3050, 1720, 1690 cm$^{-1}$. MS(CI) m/e 258 (M+H)$^+$. $^1$H NMR (CDCl$_3$, 300 MHz) 2 conformers δ0.93 (m, 3H), 1.28–1.69 (m, 14H), 1.97–2.12 (m, 1H), 2.30 (m, 0.4H), 2.50 (m, 0.6H), 3.34–3.64 (m, 2H), 3.84 (br d, J=6.2 Hz, 0.4H), 3.98 (br d, J=4.4 Hz, 0.6H). Anal. calcd. for C$_{13}$H$_{23}$NO$_4$: C, 60.68; H, 9.01; N, 5.44. Found: C, 60.66; H, 8.91; N, 5.44.

34f: N-tert-Butoxycarbonyl-trans-3-n-propyl-proline, (s)-methylbenzylamides

To a solution of trans acid of Example 34e (94.2 g, 0.37 mol), (S)-(−)methylbenzylamine (44.8 g, 0.37 mol) and 1-hydroxybenzotriazole hydrate (54.4 g, 0.40 mol) in CH$_2$Cl$_2$ (1 L) was added 1-ethyl-3-(3-dimethylamino-propyl)carbodiimide hydrochloride (76.9 g, 0.40 mol)

under nitrogen at 0° C. After stirring overnight at 23° C., the reaction mixture was diluted with EtOAc, washed with 10% aqueous citric acid, saturated aqueous NaHCO$_3$ and brine, then dried over MgSO$_4$, filtered and concentrated. The residue was dissolved in minimum amount of ether and the S-isomer (with respect to proline), preferentially crystallized upon standing (34.0 g, 90% S-isomer). The mother liquor was concentrated and the resulting residue was chromatographed on silica gel using 35% EtOAc/hexane as elutant to give 46.5 g of the R-isomer (35%, contains <5% S-isomer) 6.9 g of mixture and 16.3 g of S-isomer (90% S-isomer). The 34.0 of 90% pure S-isomer, 6.9 g of mixture and 16.3 g of 90% pure S-isomer were combined and recrystallized three time from ether/hexane to give a total of 40.2 g (30%) of S-isomer (99%+pure). Alternatively, the mixture could also be separated by HPLC with about 80% recovery. S-isomer: mp 112°–114° C. (Et$_2$O/hexane). TLC, R$_f$=0.39 (EtOAc:-hexane=1:2). $[\alpha]_D^{23}$=−56.3° (c 0.75; MeOH). $^1$H NMR (300 MHz, DMSO-d$_6$, 138° C.) δ0.88 (br t, J=7.0 Hz, 3H), 1.40 (s, 9H), 1.43 (d, J=7.1 Hz, 3H), 1.25–1.55 (m, 5H), 1.97 (m, 1H), 2.14 (m, 1H), 3.30–3.55 (m, 2H), 3.77 (d, J=5.1 Hz, 1H), 4.99 (q, J=7.1 Hz, 1H), 7.65–7.15 (m, 5H). MS (CI) m/e 361 (MH$^+$, base), 305, 261, 112. Anal. Calcd. For C$_{21}$H$_{32}$N$_2$O$_3$: C, 69.97; H, 8.95; N, 7.77. Found: C, 69.99; H, 9.05N, 7.73. R-isomer: mp 104°–105° C. (Et$_2$O/Hexane). TLC, R$_f$=0.45 (EtOAc:Hexane=1:2). $[\alpha]_D^{23}$=−65.8° (c 0.76; MeOH). $^1$H NMR (300 MHz, DMSO-d$_6$, 138° C.) δ0.91 (br t, J=7.0 Hz, 3H), 1.36 (s, 9H), 1.28–1.42 (m, 3H), 1.43 (d, J=7.1 Hz, 3H), 1.45–1.58 (m, 2H), 2.00 (m, 1H), 2.18 (m, 1H), 3.33–3.51 (m, 2H), 3.79 (d, J=4.9 Hz, 1H), 4.98 (q, J=7.1 Hz, 1H), 7.60–7.17 (m, 5H). MS (CI) m/e 361 (MH+, base), 305, 261, 112. Anal. Calcd for C$_{21}$H$_{32}$N$_2$O$_3$: C, 69.97; H, 8.95; N, 7.77. Found: C, 70.27; H, 9.25; N, 7.73.

34g: N-t-BOC-trans-3-n-propyl-proline

A solution of the S-isomer of Example 34f (40.2 g, 0.11 mol) in 8N HCl (870 mL) and glacial acetic acid (220 mL) was heated at reflux overnight. The solution was concentrated on a rotary evaporator and the residue taken up into H$_2$O and extracted with ether. The aqueous phase was concentrated and azeotroped 3 times with toluene to give 43.0 g of trans-3-n-propyl-(L)-proline and (s)-methylbenzylamine hydrochlorides. The salts were taken up in dioxane/H$_2$O (1:1, 400 mL) and then treated carefully with N,N-diisopropylethylamine (35.5 g, 0.275 mol) and di-t-butyl dicarbonate (60.0 g, 0.275 mol) sequentially at 0° C. After stirring overnight at 23° C., the mixture was diluted with ethyl acetate and the two layers were separated. The organic layer was extracted with 0.5N NaOH (2×). The combined aqueous phase was extracted with ethyl acetate once and again back-extracted ethyl acetate was washed with 0.5N NaOH. The combined basic aqueous phase was cooled to 0° C.–5° C. and acidified to pH 1.0 with cold 4N HCl and extracted immediately with EtOAc (2×). The combined EtOAc extract was washed with brine, dried (MgSO$_4$) and concentrated. The residue was dried in vacuo in a desicator over P$_2$O$_5$ to give 26.1 g (92% yield) of title compound as a white solid, mp 88°–89° C. (hexane). TLC, R$_f$=0.15 (CHCl$_3$:MeOH=9:1). $[\alpha]_D^{24}$=−38.3° (c 1.0; CHCl$_3$); $[\alpha]_D^{25}$=−42.5° (c 0.095; CHCl$_3$). $^1$H NMR (360 MHz, DMSO-d$_6$, 100° C.) δ0.90 (t, J=7.0 Hz, 3H), 1.20–1.55 (m, 15H), 1.98 (m, 1H), 2.20 (m, 1H), 3.30 (m, 1H), 3.40 (m, 1H), 3.67 (d, J=4.0 Hz, 1H). MS (CI) m/e 258 (MH)$^+$, 219 (base), 202, 158. Anal. Calcd. for C$_{13}$H$_{23}$NO$_4$: C, 60.68; H, 9.01; N, 5.44. Found: C, 60.58; H, 8.97; N, 5.44. The (+)-isomer was obtained similarly: mp 90°–92° C. (hexane). $[\alpha]_D^{24}$=+43.2° (c 1.0; CHCl$_3$).

34h: Ctp-Tpp-Asp-(NMe)Phe-NH$_2$

To a solution of the hydrochloride salt of Tpp-Asp(β-OBn)-N-Me-Ph-NH$_2$ (18.2 mg, 0.032 mmol), prepared as in Example 15g, Ctp-OH (8.7 mg, 0.035 mmol), product of Example 1c, and BOP-Cl (10 mg, 0.039 mmol) in DMF (0.5 mL) and methylene chloride (1.5 mL) was added diisopropylethylamine (10.1 mg, 0.078 mmol) at 0° C. under nitrogen. The mixture was stirred overnight at 0° C. and then poured into 3% citric acid and extracted with ethyl acetate (2×). The organic extracts were combined and washed with saturated sodium bicarbonate aqueous solution and brine. After drying with anhydrous sodium sulfate, the solvent was removed in vacuo and the residue was subjected to flash chromatography (2.5% to 10% MeOH/CHCl$_3$) to give 14 mg (57% yield) of Ctp-Tpp-Asp(β-OBn)-(NMe)phe-NH$_2$ as a solid. This material was then taken up in MeOH (2 mL) and hydrogenated under one atmosphere of hydrogen in the presence of 5% Pd/BaSO$_4$ (20 mg) for 1.5 hour at ambient temperature. After filtration of the reaction mixture through Celite ® and concentration of the filtrate, the resulting residue was chromatographed on a preparative reverse phase HPLC using 0.1% aqueous TFA and acetonitrile as eluants. The product was lyophilized to yield 12 mg of the title compound as a pink flocculent powder, mp 185°–190° C. (dec). MS(CI) m/e 659 (M+H)$^+$, 691 (MH+CH$_3$OH)$^+$. $^1$H NMR (DMSO-d$_6$, 360 MHz) δ0.90 (m, 3H), 1.20–1.65 (m, 5H), 1.19–2.15 (m, 2H), 2.15–2.45 (m, 1H), 2.45–2.60 (m, 3H), 2.75–3.00 (m, 5H), 3.40–3.25 (m, 3H), 3.50 (m, 1H), 3.60 (m, 1H), 3.69 (m, 1H), 3.81 (m, 1H), 3.95–4.00 (m, 1H), 4.05–4.20 (m, 2H), 4.52 (m, 1H), 4.94 (m, 1H), 5.10 (m, 1H), 6.77 (d, J=7.2 Hz, 1H), 7.05–6.90 (m, 2H), 7.30–7.05 (m, 7H). Anal calc for C$_{35}$H$_{42}$N$_6$O$_7$0.3CH$_3$OH 0.9CF$_3$CO$_2$H: C, 57.80; H, 5.77; N, 10.90; Found: C, 57.71; H, 6.09; N, 11.24.

EXAMPLE 35

Ctp-Cpp-Asp-Phe-NH$_2$

35a: Cpp-Asp(OBn)-Phe-NH$_2$ hydrochloride

To solution of N-BOC-cis-3-n-propyl-proline (61 mg, 0.23 mmol) (prepared from the corresponding methyl ester (Example 35e) via acid hydrolysis (6N HCl/100° C./6 hours) and treating the resulting amino acid with BOC-ON and diisopropyl ethylamine in aqueous dioxane), TFA.Asp(β-OBn)-Phe-NH$_2$ (141 mg, 0.29 mmol), 1-hydroxybenzotriazole hydrate (44 mg, 0.29 mmol) and diisopropylethylamine (37 mg, 0.29 mmol) in THF (3 mL) was added 1-(3-dimethylaminopropyl)-3-ethylcarbodiimide hydrochloride (EDCl) (55 mg, 0.29 mmol) at 0° C. under nitrogen. After stirring for 4 days at ambient temperature, the mixture was partitioned between a 10% aqueous citric acid solution and ethyl acetate. The organic phase was further washed with a saturated sodium bicarbonate aqueous solution and brine and dried (anhydrous sodium sulfate). Concentration in vacuo gave 167 mg of crude BOC-(L)-Cpp-Asp(β-OBn)-Phe-NH$_2$ and BOC-(D)-Cpp-Asp(β-OBn)-Phe-NH$_2$: MS (CI) m/e 609 (M+H)$^+$. This crude product was then treated with 10 mL of 1.5 N HCl/HOAc (prepared from 12.5 mL of conc. HCl diluted to 100 mL with AcOH) for 1 hour at room temperature. The solvents were removed in vacuo and the solid residue was washed with ether and filtered. The product was lyophilized to yield 126 mg (97% yield) of the free amino tripeptide hydrochloride salt as a white solid. MS (CI) m/e 509 (M+H)+.

35b: Ctp-Cpp-Asp-Phe-$NH_2$

To a solution of the tripeptide hydrochloride salt of Example 35a (124 mg, 0.22 mmol) and BOP-Cl (69 mg, 0.27 mmol) in methylene chloride (2 mL) was added a solution of Ctp-OH (61 mg, 0.25 mmol) in methylene chloride (1 mL)/DMF (2 mL) and diisopropylethylamine (71 mg, 0.55 mmol) at 0° C. under nitrogen. After stirring overnight at room temperature, 0.4 equivalent of BOP-Cl and 0.4 equivalent of diisopropylethylamine were added and the reaction was stirred for 24 hours. The reaction mixture was diluted with EtOAc, washed with 10% aqueous citric acid, saturated aqueous $NaHCO_3$ solution and brine, and dried ($Na_2SO_4$). Purification by flash chromatography (eluting with 4%→10% MeOH in $CHCl_3$) gave 43 mg of pure faster-eluting diastereomer, 16 mg of mixture and 36 mg of pure slower-eluting diastereomer. The faster-eluting diastereomer (43 mg, 0.059 mmol) was hydrogenated under one atmosphere of hydrogen at ambient temperature for 6 hours using 10% Pd/C (15 mg) in MeOH (5 mL). The reaction mixture was filtered through Celite ® and the solvent was removed in vacuo. The product was lyophilized to give 37 mg of the title compound as a white solid, mp 175°–180° C. MS (FAB+) m/e 645 (M+H)+, 667 (M+Na)+. $^1$H NMR (DMSO-$d_6$, 300 MHz) δ0.81 (m, 3H), 1.0 (m, 1H), 1.45–1.15 (m, 4H), 1.85–1.50 (m, 1H), 2.12–1.85 (m, 1H), 2.50–2.12 (m, 1H), 3.00–2.55 (m, 6H), 3.07 (m, 1H), 3.50–3.30 (m, 2H), 3.78–3.58 (m, 2H), 3.85 (m, 1H), 4.63–4.10 (m, 8H), 6.78 (d, J=7.2 Hz, 1H), 6.96 (t, J=8.4 Hz, 1H), 7.30–7.10 (m, 9H), Anal Calc for $C_{34}H_{40}N_6O_7$ 0.6$CF_3CO_2H$: C, 59.07; H, 5.74; N, 11.79. Found: C, 59.07; H, 6.02; N, 12.13.

EXAMPLE 36

BOC-Trp-Tpp-Asp-Trp-$NH_2$

36a: Tpp-Asp(OBn)-Trp-$NH_2$ TFA

To solution of N-BOC-trans-3-n-propyl-(L)-proline (61 mg, 0.23 mmol), TFA.Asp(OBn)-PHe-$NH_2$ (149 mg, 0.28 mmol), 1-hydroxybenzotriazole hydrate (44 mg, 0.28 mmol) and 1-(3-dimethylaminopropyl)-3-ethylcarbodiimide hydrochloride (EDCI) (55 mg, 0.28 mmol) in THF (2.5 mL) was added diisopropylethylamine (37 mg, 0.28 mmol) at 0° C. under nitrogen. After stirring for 2 days at ambient temperature, the mixture was partitioned between a 10% aqueous citric acid solution and ethyl acetate. The organic phase was further washed with saturated sodium bicarbonate solution and brine. After drying with anhydrous sodium sulfate, the solvent was removed in vacuo and the residue was taken up in methyl chloride (5 mL) and treated with TFA (5 mL) for 35 minutes at room temperature. The reaction mixture was concentrated and the resulting residue was flash chromatographed (10% MeOH/$CHCl_3$) to give 50 mg of the title compound as a yellow powder after lyopholization.

36b: BOC-Trp-Tpp-Asp-Trp-$NH_2$

To a solution of BOC-Trp-OH (25 mg, 0.083 mmol), TFA.Tpp-Asp(OBn)-Trp-$NH_2$ (50 mg, 0.076 mmol), EDCl (18 mg, 0.091 mmol), and HOBt hydrate (14 mg, 0.091 mmol) in methylene chloride (1 mL) was added diisopropylethylamine (12 mg, 0.091 mmol) at 0° C. After stirring overnight, the reaction mixture was diluted with ethyl acetate and washed with 10% aqueous citric acid, saturated aqueous sodium bicarbonate and brine, then dried with anhydrous sodium sulfate and concentrated in vacuo to yield 70 mg of yellow solid. This material was taken up in methanol (15 mL) and hydrogenated at one atmosphere of hydrogen in the presence of 5% Pd/$BaSO_4$ at room temperature for 2 hours. After filtration of the reaction mixture through Celite ® and concentration of the filtrate, the resulting residue was chromatographed on a preparative reverse phase HPLC using 0.1% aqueous TFA and acetonitrile as eluants. The product was lyophilized to yield 21 mg of the title compound as a white powder, mp 195°–200° C. (dec). MS (FAB+) m/e 744 (M+H)+. $^1$H NMR (DMSO-$d_6$, 300 MHz) δ0.81 (m, 3H), 1.10–1.50 (m, 14 H), 2.10 (m, 2H), 2.52–2.67 (m, 1H), 2.70–2.81 (m, 1H), 2.82–2.97 (m, 1H), 2.98–3.10 (m, 1H), 3.15–3.30 (m, 1H), 3.35–3.55 (m, 2H), 3.75 (m, 1H), 3.88 (d, J=6.0 Hz, 1H), 4.39 (m, 2H), 4.48 (dd, J=13.5 and 7.5 Hz, 1H), 6.90–7.00 (m, 3H, 1H $D_2O$ exchangeable), 7.01–7.10 (m, 3H, 1H $D_2O$ exchangeable), 7.10–7.20 (m, 3H, 1H, $D_2O$ exchangeable), 7.31 (d, J=8.4 Hz, 2H), 7.44–7.60 (m, 2H), 7.78 (d, J=8.7 Hz, 1H, $D_2O$, exchangeable), 8.32 (d, J=7.5 Hz, 1H, $D_2O$ exchangeable), 10.81 (m, 2H, $D_2O$ exchangeable). Anal calc for $C_{39}H_{48}N_7O_8$ $CF_3CO_2H$: C, 57.40; H, 5.87; N, 11.43; Found: C, 57.75; H, 6.03; N, 11.72.

EXAMPLE 37

BOC-β-Nal-Tpp-Asp-α-Nal-$NH_2$

37a: Tpp-Asp(OBn)-α-Nal-$NH_2$.TFA

The TFA salt of Asp(OBn)-α-Nal-$NH_2$ (151 mg, 0.28 mmol), N-BOC-trans-3-n-propyl-(L)-proline (61 mg, 0.24 mmol), 1-hydroxybenzotriazole hydrate (44 mg, 0.28 mmol), 1-(3-dimethylaminopropyl)-3-ethylcarbodiimide hydrochloride (EDCI) (55 mg, 0.28 mmol) and diisopropylethylamine (37 mg, 0.28 mmol) in methylene chloride (3 mL) were reacted under similar conditions to those described in Example 4. The product was deprotected with TFA and isolated by a procedure similar to that in Example 36a to yield the title compound as a white solid.

37b: BOC-β-Nal-Tpp-Asp-a-Nal-$NH_2$

BOC-β-Nal-OH (25 mg, 0.08 mmol), TFA.Tpp-Asp(β-OBn)-α-Nal-$NH_2$ (54 mg, 0.08 mmol), 1-hydroxybenzotriazole hydrate (15 mg, 0.096 mmol), 1-(3-dimethylaminopropyl)-3-ethylcarbodiimide hydrochloride (EDCI) (19 mg, 0.096 mmol), diisopropylethylamine (13 mg, 0.096 mmol) and methylene chloride (2 mL) were reacted under similar conditions to those described in Example 36b. The product was hydrogenated and purified in a similar manner as those described in Example 36b to give 35 mg of the title compound as a white solid, mp 190°–200° C. (dec). MS (FAB+) m/e 766 (M+H)+, 788 (M+Na)+, 666 (MH+-BOC). $^1$H NMR (DMSO-$d_6$, 300 MHz) δ0.80 (m, 3H), 1.10–1.35 (m, 12H), 1.45 (m, 1H), 1.56 (m, 1H), 2.33 (m, 2H), 2.55 (m, 1H), 2.72 (m, 1H), 2.90 (m, 1H), 3.11 (m, 1H), 3.30 (m, 1H), 3.55–3.70 (m, 2H), 3.80–3.95 (m, 2H), 4.45–4.60 (m, 3H), 7.05–7.60 (m, 10H, 4H $D_2O$ exchangeable), 7.70–8.40 (m, 9H, 1H $D_2O$ exchangeable), 12.50 (br s, 1H, $D_2O$ exchangeable). Anal calc for $C_{43}H_{51}N_5O_8$ 0.3$CF_3CO_2H$: C, 65.45; H, 6.46; N, 8.75. Found: C, 65.37; H, 6.42; N, 8.72.

EXAMPLE 38

BOC-β-Nal-Tpp-Asp-β-Nal-NH$_2$

38a: Tpp-Asp(OBn)-β-Nal-NH$_2$.TFA

The TFA salt of Asp(OBn)-β-Nal-NH$_2$ (151 mg, 0.28 mmol), N-BOC-trans-3-n-propyl-(L)-proline (61 mg, 0.24 mmol), 1-hydroxybenzotriazole hydrate (44 mg, 0.28 mmol), 1-(3-dimethylaminopropyl)-3-ethylcarbodiimide hydrochloride (EDCI) (55 mg, 0.28 mmol) and diisopropylethylamine (37 mg, 0.28 mmol) in methylene chloride (3 mL) were reacted under similar conditions to those described in Example 37a. The product was deprotected with TFA and isolated in a similar manner as in Example 37a to yield the title compound as a white solid.

38b: BOC-β-Nal-Tpp-Asp-β-Nal-NH$_2$

BOC-β-Nal-OH (25 mg, 0.08 mmol), TFA.Tpp-Asp(OBn)-β-Nal-NH$_2$ (54 mg, 0.08 mmol), 1-hydroxybenzotriazole hydrate (15 mg, 0.096 mmol), 1-(3-dimethylaminopropyl)-3-ethylcarbodiimide hydrochloride (EDCI) (19 mg, 0.096 mmol), diisopropylethylamine (13 mg, 0.096 mmol) and methylene chloride (2 mL) were reacted under similar conditions to those described in Example 36a. The product was hydrogenated and purified in a similar manner as those described in Example 36b to give 34 mg of the title compound as a white solid, mp 190°-200° C. (dec). MS (FAB+) m/e 766 (M+H)+, 788 (M+Na)+, 666 (MH+-BOC). $^1$H NMR (D$_2$O, 300 MHz) δ0.78 (m, 3H), 1.00–1.32 (m, 12H), 1.39 (m, 1H), 1.52 (m, 1H), 1.99 (m, 2H), 2.55 (m, 1H), 2.72 (m, 1H), 2.90 (m, 1H), 3.05–3.18 (m, 2H), 3.27 (m, 1H), 3.56 (m, 1H), 3.77–3.95 (m, 2H), 4.45–4.60 (m, 3H), 7.10–7.55 (m, 8H, 2H D$_2$O, exchangeable), 7.65–8.10 (m, 10H, 2H D$_2$O, exchangeable), 8.36 (d, J=7.2 Hz, 1H D$_2$O, exchangeable), 12.44 (br s, 1H, D$_2$O exchangeable). Anal Calc for C$_{43}$H$_{51}$N$_5$O$_8$0.8CF$_3$CO$_2$H: C, 62.50; H, 6.09; N, 8.17; Found: C, 62.30; H, 6.01; N, 8.40

EXAMPLE 39

Ctp-Tpp-Asp-α-Nal-NH$_2$

To a mixture of Ctp-OH (24 mg, 0.10 mmol), TFA.Tpp-Asp(β-OBn)-α-Nal-NH$_2$ (67 mg, 0.10 mmol) and Bop-Cl (31 mg, 0.12 mmol) in methylene chloride (2 mL)/DMF (0.5 mL) was added diisopropylethylamine (31 mg, 0.24 mmol) at 0° C. under nitrogen. After stirring overnight at ambient temperature, the reaction mixture was worked up in a similar manner to those described in Example 36b. The product was hydrogenated and purified in a similar manner as those described in Example 36b to give 32 mg of the title compound as a white solid, mp 185°-190° C. (dec). MS (FAB+) m/e 695 (M+H)+, 713 (MH+H$_2$O)+. High resolution MS(CI) m/e 695.3198 ((M+H)+, for C$_{38}$H$_{43}$N$_6$O$_7$, calcd 695.3193). $^1$H NMR (DMSO-d$_6$, 300 MHz) δ0.81 (m, 3H), 1.27 (m, 3H), 1.36–1.65 (m, 2H), 2.05 (m, 2H), 2.58 (m, 2H), 2.79 (dd, J=16.5, 6.3 Hz, 1H), 3.15–3.48 (m, 3H), 3.50–3.70 (m, 2H), 3.88 (m, 1H), 3.91 (d, J=6.0 Hz, 1H), 4.11 (m, 1H), 4.40 (m, 2H), 4.52 (m, 1H), 6.77 (d, J=7.5 Hz, 1H, 6.96 (t, J=7.5 Hz, 1H), 6.97 (d, J=6.0 Hz, 1H, D$_2$O exchangeable), 7.15 (2H, 1H D$_2$O exchangeable), 7.20–7.40 (m, 5H, 2H, D$_2$O exchangeable), 7.51 (m, 2H), 7.77 (d, J=7.8 Hz, 1H), 7.91 (m, 1H), 7.97 (d, J=8.4 Hz, 1H, D$_2$O exchangeable), 8.17 (m, 1H), 8.44 (m, 1H, D$_2$O exchangeable), 10.95 (m, 1H, D$_2$O exchangeable), 12.50 (br s, 1H, D$_2$O exchangeable).

EXAMPLE 40

Ctp-Tpp-Asp-β-Nal-NH$_2$

To a mixture of Ctp-OH (24 mg, 0.10 mmol), TFA.Tpp-Asp(β-OBn)-β-Nal-NH$_2$ (67 mg, 0.10 mmol) and Bop-Cl (31 mg, 0.12 mmol) in methylene chloride (2 mL)/DMF (0.5 mL) was added diisopropylethylamine (31 mg, 0.24 mmol) at 0° C. under nitrogen. After stirring overnight at ambient temperature, the reaction mixture was worked up in a similar manner to those described in Example 36b. The product was hydrogenated and purified in a similar manner as those described in Example 36b to give 23 mg of the title compound as a white solid, mp 185°-190° C. (dec). MS (FAB+) m/e 695 (M+H)+, 717 (M+Na)+. $^1$H NMR (DMSO-d$_6$, 300 MHz) δ0.80 (m, 3H), 1.19 (m, 3H), 1.32–1.62 (m, 2H), 1.98 (m, 2H), 2.50–2.75 (m, 3H), 3.03 (m, 2H), 3.20–3.45 (m, 2H), 3.50–3.70 (m, 3H), 3.82 (m, 1H), 3.91 (m, 1H), 4.12 (m, 1H), 4.40 (m, 2H), 4.52 (m, 1H), 6.77 (d, J=7.2 Hz, 1H), 6.95 (t, J=7.2 Hz, 1H), 6.96 (m, 1H, D$_2$O exchangeable), 7.17 (m, 2H, 1H D$_2$O exchangeable), 7.22 (d, J=8.1 Hz, 1H), 7.30–7.55 (m, 4H, 1H D$_2$O exchangeable), 7.65–7.89 (m, 5H, 1H D$_2$O exchangeable), 7.93 (m, 1H, D$_2$O exchangeable), 8.47–8.52 (m, 1H, D$_2$O exchangeable), 10.9–11.0 (m, 1H, D$_2$O exchangeable). Anal calc for C$_{38}$H$_{42}$N$_6$O$_7$ 0.9CF$_3$CO$_2$H: C, 59.95; H, 5.42; N, 10.54; Found: C, 59.59; H, 5.75; N, 10.86.

EXAMPLE 41

Ctp-Tpp-Asp-Cha-NH$_2$

41a: Tpp-Asp(OBn)-Cha-NH$_2$.TFA

The TFA salt of Asp(OBn)-Cha-NH$_2$ (95 mg, 0.19 mmol), N-BOC-trans-3-n-propyl-(L)-proline (50 mg, 0.19 mmol), 1-hydroxybenzotriazole hydrate (45 mg, 0.23 mmol), 1-(3-dimethylaminopropyl)-3-ethylcarbodiimide hydrochloride (EDCI) (45 mg, 0.23 mmol) and diisopropylethylamine (30 mg, 0.23 mmol) in methylene chloride (7 ml) were reacted under similar conditions to those described in Example 36a. The product was deprotected with TFA and isolated in a similar manner as in Example 36a to yield 66 mg of title compound as a white solid.

41b: Ctp-Tpp-Asp-Cha-NH$_2$

To a mixture of Ctp-OH (27 mg, 0.11 mmol), TFA.Tpp-Asp(OBn)-Cha-NH$_2$ (66 mg, 0.10 mmol) and Bop-Cl (32 mg, 0.13 mmol) in methylene chloride (5 mL)/DMF (1.5 mL) was added diisopropylethylamine (33 mg, 0.25 mmol) at 0° C. under nitrogen. After stirring overnight at ambient temperature, the reaction mixture was worked up in a similar manner to those described in Example 36b. The product was hydrogenated and purified in a similar manner as those described in Example 36b to give 22 mg of the desired product as a white solid, mp 145°-150° C. (dec). MS (FAB+) m/e 651 (M+H)+. $^1$H NMR (CD$_3$OD, 300 MHz) δ0.91 (m, 3H), 1.25–1.65 (m, 17H), 1.96–2.20 (m, 2H), 2.70–3.10 (m, 2H), 3.25 (m, 1H), 3.41 (m, 1H), 3.53 (m, 1H), 3.72 (d, J=7.5 Hz, 1H), 4.29 (q, J=7.8 Hz, 1H), 4.58–4.70 (m, 1H), 4.74–4.95 (m, 2H), 5.13 (s, 2H), 7.28–7.39 (m, 5H). Anal calc for C$_{34}$H$_{46}$N$_6$O$_7$ 1.5CF$_3$CO$_2$H 1.3 H$_2$O: C, 52.58; H, 5.98; N, 9.94; Found: C, 52.39; H, 5.73; N, 10.33.

EXAMPLE 42

Ctp-(1,4-thiazane-3-carbonyl)-Asp-Phe-NH$_2$

42a: BOC-1,4-Thiazane-3-Carboxylic Acid

A heterogeneous suspension of thiazane-3-carboxylic acid (J. F. Carson, F. F. Wong, *J. Org. Chem.*, 1964, 29, 2203) (0.28 g, 1.88 mmol) and BOC-ON [2-(tert-butoxycarbonyloxyimino)-2-phenylacetronitrile] (0.70 g, 2.84 mmol) and TEA (0.29 g, 2.87 mmol) in acetone (5 mL) and water (5 mL) was rapidly stirred at ambient temperature. The mixture was diluted with water, washed several times with ether then acidified with 1M HCl and extracted several times with methylene chloride. The organic phase was washed with brine and dried over sodium sulfate. Evaporation of the solvent in vacuo yielded 0.39 g (84% yield) of a white solid. MS (EI) m/e 247 M+. $^1$H NMR(300 MHz, CDCl$_3$) δ1.47 (br s, 9H), 2.46 (br t, 1H), 2.72 (br t, 1H), 2.92 (dd, J=14 Hz, 5 Hz, 1H), 3.05-3.37 (m, 2H), 4.19-4.42 (m, 1H), 5.10,5.32 (s, 1H).

42b: BOC-(1,4-Thiazane-3-carbonyl)-Asp(OBn)-Phe-NH$_2$

To a solution of Example 42a (0.130 g, 0.27 mmol) in methylene chloride (5 mL) was added NMM (30 mg, 0.29 mmol), Asp(OBn)-PheNH$_2$ hydrochloride (50 mg, 0.20 mmol) and HOBt (30 mg, 0.22 mmol). The solution was cooled to 0° C. and DCC (45 mg, 0.22 mmol) was added to form a milky suspension. The reaction was allowed to warm to ambient temperature and stand for 18 hours. The mixture was diluted with ethyl acetate, filtered and the solution was washed with 1M HCl, saturated bicarbonate solution and brine. After drying over sodium sulfate, the solvent was removed in vacuo and the residue was chromatographed on silica gel eluting with ethyl acetate:hexane to yield 104 mg (87%) of the title compound as a white solid. MS(FAB) m/e 599 (M+H)+. NMR(DMSO-d$_6$, 300 MHz) δ1.49 (s, 9H), 2.34-2.45 (m, 1H), 2.60-2.86 (m, 4H), 2.92-3.24 (m, 5H), 4.63 (q, 1H), 4.72-4.81 (m, 1H), 4.88 (br s, 1H), 5.08 (dd, 2H), 5.28 (br s, 1H), 6.98 (br d, 1H), 7.08-7.42 (m, 9H).

42c: (1,4-Thiazane-3-Carbonyl)-Asp(OBn)-Phe-NH$_2$ hydrochloride

A solution of compound of Example 42b (450 mg, 0.75 mmol) in HCl/acetic acid (20 mL) was stirred at ambient temperature for 4 hours. The addition of ether precipitated the salt which was collected, washed with fresh ether and dried to yield 390 mg (100% yield) of a white solid. MS(FAB+) m/e 499 (M+H)+. $^1$H NMR(DMSO-d$_6$, 300 MHz) δ2.56-3.22 (m, 10H), 3.93 (br s, 1H), 4.35-4.44 (m, 1H), 4.60-4.68 (m, 1H), 5.11 (s, 2H), 7.15-7.46 (m, 10H).

42d: Ctp-(1,4-thiazane-3-carbonyl)-Asp(OBn)-Phe-NH$_2$

To a homogeneous solution of Ctp-OH (66 mg, 0.27 mmol, from Example 1c) in DMF (1 mL) and methylene chloride (7 mL) cooled to 0° C. were added compound of Example 42c (173 mg, 0.32 mmol), diisopropylethylamine (119 mg, 0.92 mmol) and BOP-Cl (76 mg, 0.29 mmol). The solution was allowed to stand at 0° C. for 18 hours then diluted with 25% isopropanol in chloroform, washed with 1M HCl, saturated bicarbonate solution and brine. After drying over sodium sulfate, the solvent was removed in vacuo to yield a sludge that was chromatographed on silica (Chromatatron) using methanol in chloroform to yield a white solid. MS (FAB+) m/e 725 (M+H)+. $^1$H NMR(DMSO-d$_6$, 300 MHz, partial spectrum due to H$_2$O interference) δ2.57-2.90 (m, 3H), 2.90-3.07 (m, 4H), 3.70-3.87 (m, 2H), 3.96-4.05 (m, 1H), 4.12-4.20 (m, 1H), 4.36-4.44 (m, 1H), 4.65-4.84 (m, 3H), 4.96-5.09 (m, 2H), 6.89 (d, 1H), 6.97 (t, J=7 Hz, 1H), 7.04 (d, 1H), 7.07-7.42 (m, ca. 12H), 7.85 (d, 1H), 8.18 (d, 1H).

42e: Ctp-(1,4-thiazane-3-carbonyl)-Asp-Phe-NH$_2$

The compound of Example 42d (55 mg) was treated with 10% Pd-C (50 mg) in methanol (5 mL) in the presence of cyclohexadiene (0.15 mL). The suspension was stirred at ambient temperature for 24 hours at which time an additional quantity of catalyst (50 mg) and cyclohexadiene were added (0.15 mL). After stirring an additional 24 hours, the catalyst was filtered, the solvent removed in vacuo and the residue chromatographed on reverse phase HPLC using acetonitrile and 0.1% TFA. The fractions were collected and lyopholyzed to yield a white, flocculent solid. MS(FAB−) m/e 633 (M—H)−. Anal. calcd for C$_{31}$H$_{34}$N$_6$O$_7$S.3CF$_3$CO$_2$H: C, 45.50; H, 3.82; N, 8.60. Found: C, 45.46; H, 3.02; N 9.17.

EXAMPLE 43

Ctp-Pip-Asp-Phe-NH$_2$

43a: Cbz-Asp(O-t-Bu)-Phe-NH$_2$

To a −10° C. solution of Cbz-Asp(O-t-Bu) (2.5 g, 4.95 mmol) in THF (40 mL) were added NMM (0.52 g, 5.18 mmol) followed by isobutylchloroformate (0.705 g, 5.16 mmol) to form a white precipitate. The suspension was stirred for 4 minutes and a solution of Phe-NH$_2$ (0.81 g, 4.94 mmol) in DMF (10 mL) and water (5 mL) were added. The solution was stirred at −15° C. for additional 10 minutes then allowed to warm to ambient temperature. After 6 hours, the solution was diluted with ethyl acetate, washed with 1M HCl, saturated bicarbonate solution and brine. After drying over anhydrous sodium sulfate, the solvent was removed in vacuo to yield 2.07 g (89% yield) of the title compound as a white solid which was recrystallied from ethyl acetate. MS(FAB+) m/e 470 (M+H+). $^1$H NMR (300 MHz,CDCl$_3$) δ1.41 (s, 9H), 2.67 (dd, J=6 and 15 Hz, 1H), 2.80 (dd, 1H), 3.03-3.22 (m, 2H), 4.42 (m, 2H), 4.64 (m, 2H), 5.17 (dd, 2H), 7.15-7.40 (m, 10H).

43b: Asp(O-t-Bu)-Phe-NH$_2$ Acetate

A mixture of compound of Example 43a (1.20 g, 2.56 mmol) and 0.60 g 10% Pd-C in methanol (60 mL) was stirred under one atmosphere of hydrogen gas for one hour. The catalyst was filtered, washed with fresh methanol followed by acetic acid then evaporated to a yield 0.89 g (100% yield) of a white solid. MS(FAB+) m/e 336 (M+H)+. $^1$H NMR (300 MHz, DMSO-d$_6$) δ1.38 (s, 9H), 1.95 (s, 3H), 2.18 (dd, J=8 Hz and 15 Hz, 1H), 2.45 (dd, 1H), 2.84 (dd, 1H), 3.00 (dd, 1H), 3.44 (m, 1H), 4.42 (m, 1H), 7.12-7.29 (m, 5H).

43c: Cbz-Pip

To a 0° C. suspension of pipecolic acid (0.15 g, 1.16 mmol) and potassium carbonate (4.64 mmol) in water (5 mL) and THF (5 mL) was added benzyl chloroformate (0.24 g, 1.41 mmol). The mixture was rapidly stirred for one hour then allowed to warm to ambient temperature. After 6 hours, the reaction was diluted with water and washed with ether. The aqueous layer was acidified and extracted with methylene chloride. The organic phase was washed with brine then dried over sodium sulfate. The solvent was evaporated and the residue recrystallized from hexane-ethyl acetate to yield 0.23 g (75% yield) of the title compound as a white solid. MS(CI) m/e 264 (M+H)+. $^1$H NMR (300 MHz, CDCl$_3$) δ1.24-1.80 (m, 5H), 2.26 (br t, 1H), 2.93-3.14 (m, 1H), 4.00–4.19 (m, 1H), 4.87–5.05 (m, 1H), 5.15 (br s, 2H), 7.27–7.41 (m, 5H).

43d: Cbz-Pip-Asp(O-t-Bu)-Phe-NH$_2$

To a solution of Cbz-Pip (0.18 g, 0.68 mmol) in THF (20 mL) at −10° C. were added NMM (73 mg, 0.72 mmol), followed by isobutyl chloroformate (98 mg, 0.72 mmol) to form a white suspension that was stirred for 3 minutes. To the suspension was added a solution of the compound of Example 43b (284 mg, 0.72 mmol) and NMM (73 mg) in THF (3 mL) and DMF (2 mL). The solution was stirred at −10° C. for 15 minutes, then allowed to warm to ambient temperature. After 4 hours, the THF was removed in vacuo and the residue diluted with ethyl acetate, washed with 1M HCl, saturated bicarbonate solution and brine. The solvent was dried over anhydrous sodium sulfate, filtered and then evaporated. The resulting solid was chromatographed (silica, methanol-chloroform) to yield 400 mg of a white solid. MS(FAB+) m/e 581 (M+H)+. $^1$H NMR (300 MHz, CDCl$_3$) δ1.25–1.70 (m, 6H), 1.40 (s, 9H), 2.13 (br d, 1H), 2.62–2.73 (m, 2H), 3.13 (br s, 2H), 4.57–4.68 (br m, 3H), 5.16 (s, 2H), 7.16–7.40 (m, 5H).

43e: Pip-Asp(O-t-Bu)-Phe-NH$_2$ Acetate

A mixture of the compound of Example 43d (400 mg) and 10% Pd-C (200 mg) in methanol (15 mL) was hydrogenated under an atmosphere of hydrogen gas. After one hour, the catalyst was filtered, rinsed with fresh methanol and acetic acid and evaporated in vacuo to yield 328 mg of the title compound as a white solid. MS(CI) m/e 447 (M+H)+. $^1$H NMR(300 MHz,DMSO-d$_6$) δ1.20–1.58 (m, 2H), 1.34 (s, 9H), 1.63–1.73 (m, 2H), 2.39–2.62 (m, 2H), 2.77–3.11 (m, 4H), 4.31–4.41 (m, 1H), 4.49–4.58 (m, 1H), 7.08–7.42 (m, 4H), 7.81–7.93 (m, 1H).

43f: Ctp-Pip-Asp(O-t-Bu)-Phe-NH$_2$

A solution of Ctp-OH (50 mg, 0.21 mmol, prepared as in Example 1c), compound of Example 43e (115 mg, 0.23 mmol), diisopropylethylamine (89 mg, 0.69 mmol), and BOP-Cl (58 mg, 0.23 mmol) in methylene chloride (6 mL) and DMF (2 mL) was stirred at 0° C. for 36 hours. The mixture was diluted with ethyl acetate, washed with 1M HCl, saturated sodium bicarbonate solution and brine. The solvent was dried over sodium sulfate then evaporated in vacuo. The residue was chromatographed (silica, methanol-chloroform) to give 72 mg (52% yield) of the title compound as a white solid. MS(FAB−) m/e 671 (M−H)−. $^1$H NMR (300 MHz, CDCl$_3$) δ1.35–1.76 (m, 6H), 1.43 (s, 9H), 2.12 (br d, 1H), 2.66 (dd, 1H), 2.87 (dd, 1H), 3.04–3.22 (m, 2H), 3.25–3.49 (m, 2H), 3.50 (dd, 1H), 3.71–3.85 (m, 3H), 4.22 (d, 1H), 4.60–4.70 (m, 2H), 5.04 (br s, 1H), 6.89 (d, 1H), 7.03–7.34 (m, 9H), 8.25 (br s, 1H).

43g: Ctp-Pip-Asp-Phe-NH$_2$

To a solution of the compound of Example 43f (37 mg) in acetic acid (5 mL) was bubbled in a stream of hydrogen chloride gas for 30 minutes. The acetic acid was removed in vacuo, the residue dissolved in water and acetone and lyophilized. The resulting solid was chromatographed (silica gel, acetic acid-water-pyridine-ethyl acetate) to yield 28 mg of a white flocculent solid after lyophilization. MS(FAB+) m/e 617 (M+H)+. $^1$H NMR (300 MHz, DMSO-d$_6$) δ1.23–1.67 (m, 6H), 2.14 (br d, 1H), 2.65 (dd, 1H), 2.77–2.90 (m, 2H), 3.06 (dd, 1H), 3.24–3.40 (m, 2H), 3.75–4.05 (m, 2H), 4.31–4.40 (br m, 1H), 4.50–4.86 (m, 3H), 5.08 (br s, 1H), 6.83 (d, 1H), 7.00 (t, J=7 Hz, 1H), 7.18–7.32 (m, 8H). Anal calc for C$_{32}$H$_{36}$N$_6$O$_7$.1.5H$_2$O: C, 59.71; H, 6.11; N, 13.06. Found: C, 59.62; H, 5.76; N, 12.90.

Example 44

BOC-Trp-(1,4-thiazepine-3-carbonyl)-Asp-Phe-NH$_2$

44a: S-(3-Hydroxypropyl)cysteine

The compound was prepared in a similar manner to that described by J. F. Carson, et al, *J. Org. Chem.*, 1964, 29, 2203. To a solution of sodium (6.44 g, 0.281 mol) in liquid ammonia (300 mL) was added cysteine (15.0 g, 62.5 mmol) over a 30 minutes period until permanent discharge of blue. Bromopropanol (15,8 mL, 0.175 mol) was added dropwise over 1 hour. The ammonia was allowed to evaporate and the resulting solid was dissolved in 1M HCl and passed through a column of Dowex 50 (H+) (5×30 cm) eluting with 1N ammonium hydroxide. Lyopholyzation yielded 21.3 g of the title compound as a white solid. MS(CI) m/e 180 (M+H)+. $^1$H NMR (DMSO-d$_6$, 300 MHz) δ1.70–2.00 (m, 3H), 2.70 (t, J=7.5 Hz, 2H), 3.00–3.21 (m, 3H), 3.58–3.84 (m, 3H), 3.93 (dd, 1H).

44b: BOC-1,4-Thiazepine-3-carboxylic acid

The compound from Example 44a (5.0 g, 27.9 mmol) was dissolved in concentrated HCl (400 mL) and heated at 90° C. for 16 hours. The mixture was evaporated to a white solid to which a solution of sodium bicarbonate (5.8 g, 70 mmol) in 1:1 ethanol:water (200 mL) was added then refluxed for 17 hours. Di-t-butyl-dicarbonate (9.6 mL, 42 mmol) was added to the cooled solution and allowed to stand for 16 hours. The volume of the reaction was then reduced to 100 mL, acidified with 1M phosphoric acid and extracted with 25% isopropanol-chloroform. The combined organic phase was washed with brine, dried over sodium sulfate and evaporated to a residue, which was chromatographed on silica gel eluting with methanol-chloroform to yield 0.91 g of the title compound as a white solid. MS(CI) m/e 262 (M+H)+. $^1$H NMR (DMSO-d$_6$, 300 MHz) δ1.46–1.51 (s, 9H), 1.78–2.05 (m, 2H), 2.50–2.62 (m, 2H), 2.68–2.78 (m, 1H), 2.80–3.00 (m, 1H), 3.20–3.25 (m, 1H), 3.75–3.80 (m, 1H), 4.68–4.85 (m, 1H).

44c: BOC-1,4-Thiazepine-3-carbonyl-Asp(OBn)-Phe-NH$_2$

The compound was prepared in a similar manner to that described for Example 43b. MS(CI) m/e 613 (M+H)+. $^1$H NMR (DMSO-d$_6$, 300 MHz) δ1.34–1.45 (m, 9H), 1.62–1.80 (m, 1H), 1.88–1.96 (m, 1H), 2.40–2.52 (m, 2H), 2.58–2.65 (m, 3H), 2.78–3.18 (m, 3H), 3.42–3.47 (m, 1H), 3.63–3.84 (m, 1H), 4.31–4.45 (m, 1H), 4.48–4.50 (m, 1H), 4.58–4.66 (m, 1H), 5.07 (s, 2H), 7.13–7.38 (m, 10H), 7.78–7.84 (dd, 1H), 8.15 (d, 1H), 8.54–8.65 (dd, 1H).

44d: BOC-Trp-(1,4-thiazepine-3-carbonyl)-Asp(OBn)-Phe-NH$_2$

The peptide of Example 44c (120 mg, 0.20 mmol) was treated with a solution of HCl in acetic acid (3 mL) for 1 hours. The solution was then frozen and lyophylized to yield 108 mg of a white solid that was then allowed to react in a manner similar to that described for Example 43d. Chromatography (silica gel, methanol-chloroform) yield 58 mg of a white solid. MS(FAB+) m/e 799 (M+H)+. $^1$H NMR (DMSO-d$_6$, 300 MHz) δ1.14 (s, 2H), 1.26–1.34 (s, 9H), 1.71–2.12 (m, 3H), 2.45–3.27 (m, 8H), 3.41–3.50 (m, 1H), 4.32–4.70 (m, 3H), 4.90–5.18 (m, 3H), 6.95–7.40 (m, 15H), 7.50 (d, 1H), 7.90 (t, 1H), 8.15 (d, 1H), 10.83 (m, 1H).

44e: BOC-Trp-(1,4-thiazepine-3-carbonyl)-Asp-Phe-NH₂

A solution of the peptide of Example 19 (50 mg, 0.063 mmol), 10% palladium on barium sulfate (80 mg) and 1,4-cyclohexadiene (2 mL) in methanol (3 mL) was stirred at 50° C. for 24 hours. The catalyst was filtered, washed with fresh methanol and the filtrate was evaporated in vacuo to a residue. Chromatography (silica gel, pyridine-acetic acid-water-ethyl acetate) followed by lyopholyzation of the residue upon evaporation yielded 21 mg of the title compound as a white solid. MS(FAB+) m/e 704 (M+H)+. ¹H NMR (DMSO-d₆, 300 MHz) δ1.30 (s, 9H), 1.80–2.10 (m, 3H), 2.39–3.30 (m, 10H), 3.62–3.75 (m, 1H), 3.98–4.50 (m, 2H), 4.65–4.80 (m, 1H), 4.90–5.00 (m, 1H), 6.05–6.13 (m, 1H), 6.75–7.25 (m, 9H), 7.35 (d, 1H), 7.55 (d, 1H), 7.80–7.96 (m, 1H), 10.55–10.61 (m, 1H). Anal calc for $C_{35}H_{44}N_6O_8S \cdot 1.5\ H_2O$: C 57.12, H, 6.44, N 11.42; found: C 56.92, H, 6.12, N 11.05.

EXAMPLE 45

2-[3-(1H-indol-3-ylmethyl)-2,5-dioxo-1-piperazinyl]-valeryl-Asp-Phe-NH₂

45a: Nva-N-(carbomethoxymethyl) benzyl ester

To a solution of norvaline benzyl ester hydrochloride (1.00 g, 4.11 mmol) in acetonitrile (30 mL) were added diisopropylethylamine (55 g, 4 mmol), potassium carbonate (1.6 g) and methyl bromoacetate (0.71 g, 4.65 mmol). The heterogeneous mixture was stirred at ambient temperature for 18 hours at which time an additional portion of bromoacetate was added (0.32 g, 2.11 mmol) and sodium iodide (63 mg). The mixture was allowed to stand an additional 18 hours at ambient temperature then diluted with ethyl acetate and washed with water and brine. After drying over sodium sulfate, the solvent was removed in vacuo and the oily residue chromatographed (silica gel, hexane-ethyl acetate) to yield 0.91 g (84% yield) of the title compound as a clear, colorless oil. MS(CI) m/e 280 (M+H)+. ¹H NMR (300 MHz, CDCl₃) d 0.90 (t, J=7 Hz, 3H), 1.32–1.45 (m, 2H), 1.57–1.76 (m, 2H), 3.31–3.48 (m, 3H), 3.70 (s, 3H), 5.16 (s, 2H), 7.32–7.40 (m, 5H).

45b: Cbz-D-Trp-Nva-N-(carbomethoxymethyl) benzyl ester

A solution of the compound of Example 46a (0.70 g, 2.51 mmol), Cbz-D-Trp (1.27 g, 3,75 mmol), diisopropylethylamine (1.06 g, 8.2 mmol) and BOP-Cl (1.15 g, 4.52 mmol) in methylene chloride (40 mL) and DMF (5 mL) was allowed to stand at 0° C. for three days. The mixture was diluted with ethyl acetate, washed with saturated bicarbonate solution and dried over sodium sulfate. The solvent was removed in vacuo and the residue chromatographed (on silica gel, eluting with ethyl acetate hexane) to yield 0.17 g of the title compound as a clear, colorless oil. MS (FAB+) m/e 600 (M+H)+. ¹H NMR (300 MHz, CDCl₃) δ0.78–0.92 (m, 3H), 1.19–1.45 (m, 2H), 1.55–1.85 (m, 4H), 3.08–3.85 (m, 3H), 3.55, 3.70 (s, 3H), 4.02 (dd, 1H), 4.94–5.12 (m, 4H), 6.98–7.68 (m, 16H).

45c: 2-[3-(1H-indol-3-ylmethyl)-2,5-dioxo-1-piperazinyl]valeric acid

A solution containing the compound of Example 45b (0.16 g) and 10% Pd-C (80 mg) in methanol (25 mL) was hydrogenated under a balloon of hydrogen gas. After 3 hours, the catalyst was filtered, washed with fresh methanol and evaporated to a glassy solid that was chromatographed (on silica gel, eluting with pyridine-acetic acid-water-ethyl acetate) to yield 75 mg of a white, flocculent solid after lyophilyzation.

45d: 2-[3-(1H-indol-3-ylmethyl)-2,5-dioxo-1-piperazinyl]valeryl-Asp(OBn)-Phe-NH₂

A solution of acid of Example 45c (60 mg, 0.17 mmol), TFA-Asp(OBn)-Phe-NH₂ (110 mg, 0.18 mmol), diisopropylethylamine (24 mg, 0.19 mmol), HOBt (47 mg, 0.35 mmol) and EDCI (35 mg, 0.18 mmol) in methylene chloride (20 mL) and DMF (5 mL) was stirred at ambient temperature for 18 hours. The mixture was diluted with ethyl acetate and washed with 1M phosphoric acid, saturated sodium bicarbonate solution and brine. The solvent was dried over sodium sulfate and evaporated to a residue that was chromatographed (silica gel, methanol-chloroform) to yield 114 mg of a white solid. MS(FAB+) m/e 695 (M+H)+. ¹H NMR (300 MHz, DMSO-d₆) δ0.75–0.90 (m, 3H), 0.96–1.19 (m, 2H), 1.41–1.70 (m, 2H), 2.38–2.66 (m, 2H), 2.74–3.20 (m, 4H), 3.28–3.58 (m, 2H), 4.10 (br s, 1H), 4.25–4.85 (m, 4H), 5.07 (br s, 1H), 5.72 (br m, 2H), 6.90–7.55 (m, 16H).

45e: 2-[3-(1H-indol-3-ylmethyl)-2,5-dioxo-1-piperazinyl]valeryl-Asp-Phe-NH₂

A solution of the peptide of Example 45d (101 mg, 0.15 mmol) and 10% Pd-C (50 mg) in methanol (15 mL) was hydrogenated under a balloon of hydrogen gas. After 2 hours, the catalyst was filtered, washed with fresh methanol and evaporated to a residue that was purified by preparative reverse phase HPLC (C-18, acetonitrile-water) and lyopholyzed to yield 40 mg of a white flocculent product. MS(FAB+) m/e 605 (M+H)+. ¹H NMR (DMSO-d₆, 500 MHz) δ0.79 (t, J=7 Hz, 3H), 1.03 (br q, 2H), 1.42–1.51 (m, 1H), 1.53–1.62 (m, 1H), 2.42–2.52 (m, 2H), 2.65 (dd, J=6 Hz, J=16 Hz, 1H), 2.82–2.88 (m, 1H), 3.03 (dd, 1H), 3.11 (d, 2H), 4.08–4.13 (m, 1H), 4.33–4.40 (m, 1H), 4.45–4.51 (m, 1H), 4.64–4.71 (m, 1H), 6.95 (t, J=7 Hz, 1H), 7.04 (t, 1H), 7.08–7.36 (m, ca.10H), 7.51 (d, 1H), 7.78 (d, 1H), 8.23 (d, 1H). Anal calc for $C_{31}H_{35}N_6O_7 \cdot 1.5H_2O$: C, 58.94; H, 6.22; N, 13.30. Found: C, 59.66; H, 5.36; N, 13.08.

EXAMPLE 46

2-[3-(1H-indol-3-ylmethyl)-2,5-dioxo-1-piperazinyl]isocaproyl-Asp-Phe-NH₂

46a: Leu-N-(carbomethoxymethyl) Benzyl Ester

The compound was prepared in a manner similar to that described in Example 45a. MS(CI) m/e 294 (M+H)+. ¹H NMR (300 MHz, CDCl₃) δ0.82–0.90 (m, 3H), 1.23–1.34 (m, 4H), 1.59–1.66 (m, 2H), 3.29–3.37 (m, 1H), 3.35 (d, J=17 Hz, 1H), 3.45 (d, 1H), 3.71 (s, 3H), 5.17 (d, 2H), 7.32–7.42 (m, 5H).

46b: Cbz-D-Trp-Leu-N-(carbomethoxymethyl) Benzyl Ester

The title compound was prepared in a manner similar to that described in Example 45b. MS(CI) m/e 614 (M+H)+. ¹H NMR (300 MHz, CDCl₃) δ0.78–0.89 (m, 6H), 1.03–1.35 (m, 3H), 3.05–3.40 (m, 2H), 3.55, 3.70 (s, 3H), 4.00–4.25 (m, 2H), 4.55 (br t, 1H), 4.72–5.15 (m, 6H), 5.46–5.56 (m, 1H), 6.98–7.40 (m, 16H).

46c: 2-[3-(1H-indol-3-ylmethyl)-2,5-dioxo-1-piperazinyl]isocaproic acid

The title compound was prepared in a manner similar to that described in Example 45c. MS(CI) m/e 358 (M+H)+. ¹H NMR (300 MHz, DMSO-d₆) δ0.78–0.86 (m, 3H), 0.93–1.29 (m, 4H), 1.52–1.67 (m, 1H), 1.74–1.87 (m, 1H), 3.13 (d, 2H), 3.60 (br s, 2H), 4.12 (br t, 1H), 4.52–4.60 (m, 1H), 6.90–7.16 (m, 3H), 7.32 (d, 1H), 7.52 (d, 1H).

46d: 2-[3-(1H-indol-3-ylmethyl)-2,5-dioxo-1-piperazinyl]isocaproyl-Asp(OBn)-Phe-NH$_2$ The title compound was prepared in a manner similar to that described in Example 45d. MS(FAB+) m/e 708 (M+H)+. $^1$H NMR (300 MHz, DMSO-d$_6$) δ0.76–1.28 (m, 8H), 1.40–1.70 (m, 2H), 2.52–2.63 (dd, 1H), 2.74–3.15 (m, 5H), 4.10 (br t, 1H), 4.34–4.42 (m, 1H), 4.52–4.62 (m, 2H), 5.08 (s, 2H), 6.93 (t, J=7 Hz, 1H), 7.02 (t, 1H), 7.08–7.39 (m, 13H), 7.50 (d, 1H), 7.80 (d, 1H), 8.18–8.32 (m, 2H).

46e: 2-[3-(1H-indol-3-ylmethyl)-2,5-dioxo-1-piperazinyl]isocaproyl-Asp-Phe-NH$_2$ The title compound was prepared in a manner similar to that described for Example 45e. MS(FAB+) m/e 691 (M+H)+. $^1$H NMR (DMSO-d$_6$, 300 MHz) δ0.77–0.88 (m, 3H), 0.94–1.06 (m, 2H), 1.14–1.31 (m, 3H), 1.41–1.52 (m, 1H), 1.55–1.69 (m, 1H), 2.52–2.69 (m, 1H), 2.80–2.96 (m, 1H), 2.99–3.18 (m, 3H), 4.08–4.18 (m, 1H), 4.31–4.41 (m, 1H), 4.43–4.53 (m, 1H), 4.65–4.75 (m, 1H), 6.89–7.58 (m, ca. 12H), 8.15–8.36 (m, 3H). Anal Calcd for C$_{32}$H$_{38}$N$_6$O$_7$ H$_2$O: C, 60.37; H, 6.33; N, 13.20. Found: C, 60.54; H, 5.87; N, 12.96.

EXAMPLE 47

2-[3-(1H-indol-3-ylmethyl)-2,5-dioxo-1-piperazinyl]-caproyl-Asp-Phe-NH$_2$

47a: Nle-N-(carbomethoxymethyl) Benzyl Ester

The title compound was prepared in a manner similar to that described for Example 45a. MS(CI) m/e 294 (M+H)+. $^1$H NMR (300 MHz, CDCl$_3$) δ0.86 (t, 3H), 1.23–1.35 (m, 4H), 1.61–1.77 (m, 2H), 3.30–3.48 (m, 3H), 3.71 (s, 3H), 5.17 (dd, 2H), 7.32–7.40 (m, 5H).

47b: Cbz-D-Trp-Nle-N-(carbomethoxymethyl) Benzyl Ester

The title compound was prepared in a manner similar to that described for Example 45b. MS(CI) m/e 614 (M+H)+. $^1$H NMR (300 MHz, CDCl$_3$) δ0.78–0.81 (m, 3H), 1.04–1.36 (m, 4H), 1.57–1.90 (m, 2H), 3.07–3.41 (m, 4H), 3.69 (s, 3H), 3.75 (d, J=18 Hz, 1H), 4.20 (d, 1H), 4.55 (br t, 1H), 4.86 (d, J=13 Hz, 1H), 4.95–5.14 (m, 4H), 5.46–5.60 (m, 1H), 6.95–7.40 (m, 14H), 7.57–7.70 (m, 2H), 7.82 (br s, 1H), 7.95 (br s, 1H).

47c: 2-[3-(1H-indol-3-ylmethyl)-2,5-dioxo-1-piperazinyl]caproic acid

The title compound was prepared in a similar manner to that described for Example 45c. MS(CI) m/e 358 (M+H)+. $^1$H NMR (300 MHz, DMSO-d$_6$) δ0.72–0.89 (m, 3H), 0.95–1.31 (m, 4H), 1.53–1.68 (m, 1H), 1.72–1.86 (m, 1H), 3.12–3.18 (m, 2H), 3.58 (d, 2H), 4.13 (br t, 1H), 4.53–4.64 (m, 1H), 6.96 (t, J=7 Hz, 1H), 7.05 (t, 1H), 7.12 (s, 1H), 7.32 (d, J=7 Hz, 1H), 7.52 (d, 1H), 8.18 (br s, 1H).

47d: 2-[3-(1H-indol-3-ylmethyl)-2,5-dioxo-1-piperazinyl]caproyl-Asp(OBn)-Phe-NH$_2$ The title compound was prepared in a similar manner to that described for Example 45d. MS(CI) m/e 709 (M+H)+. $^1$H NMR (300 MHz, CDCl$_3$) δ0.88 (t, J=7 Hz, 3H), 1.00–1.13 (m, 2H), 1.13–1.36 (m, 3H), 2.74 (dd, J=16 and 6 Hz, 1H), 2.85 (dd, 1H), 3.08–3.27 (m, 3H), 3.37 (dd, J=18 and 5 Hz, 1H), 3.57 (d, J=17 Hz, 1H), 3.86 (d, 1H), 4.17 (br t, 1H), 4.25–4.31 (m, 1H), 4.53 (q, 1H), 4.64 (q, 1H), 5.04 (d, J=12 Hz, 1H), 5.09 (d, 1H), 7.00–7.41 (m, 16 Hz), 7.59 (d, J=8 Hz, 1H).

47e: 2-[3-(1H-indol-3-ylmethyl)-2,5-dioxo-1-piperazinyl]caproyl-Asp-Phe-NH$_2$

The title compound was prepared in a similar manner to that described for Example 45e. MS(FAB+) m/e 691 (M+H)+. $^1$H NMR (300 MHz, DMSO-d$_6$) δ0.81 (t, J=7 Hz, 3H), 0.92–1.06 (m, 2H), 1.13–1.28 (m, 2H), 1.39–1.51 (m, 1H), 1.52–1.67 (m, 1H), 2.38–2.65 (m, 2H), 2.80–2.90 (m, 1H), 3.02–3.15 (m, 2H), 3.42–3.57 (m, 2H), 4.07–4.15 (m, 1H), 4.19–4.29 (m, 1H), 4.41–4.51 (m, 1H), 4.66–4.74 (m, 1H), 6.91–7.53 (m, 12H). Anal Calcd for C$_{32}$H$_{38}$N$_6$O$_7$.H$_2$O: C 60.36, H 6.33, N 13.20; found: C 60.29, H 6.41, N 12.82.

EXAMPLE 48

2-[3-(2-Naphthylmethyl)-2,5-dioxo-1-piperazinyl]isocaproyl-Asp-Phe-NH$_2$

48a: Cbz-D-Trp-β-Nal-N-(carbomethoxymethyl) Benzyl Ester

The title compound was prepared in a manner similar to that described for Example 45a. MS(CI) m/e 625 (M+H)+. $^1$H NMR (CDCl$_3$, 300 MHz) δ0.71–0.96 (m, 8H), 1.24–1.38 (m, 1H), 2.95–3.38 (m, 2H), 3.62–3.80 (m, 5H), 4.80–5.18 (m, 4H), 5.25–5.48 (m, 2H), 7.18–7.82 (m, 18H).

48b: 2-[3-(2-Naphthylmethyl)-2,5-dioxo-1-piperazinyl]isocaproic acid

The title compound was prepared in a manner similar to that described for compound of Example 45b. MS(CI) m/e 369 (M+H)+. $^1$H NMR (DMSO-d$_6$, 300 MHz) δ0.82 (t, 6H), 1.35–1.38 (m, 1H), 1.61–1.75 (m, 2H), 3.11–3.75 (m, 4H), 4.25–4.40 (m, 1H), 4.78–4.85 (m, 1H), 7.33–7.48 (m, 3H), 7.70 (s, 1H), 7.78–7.89 (m, 3H), 8.41 (s, 1H).

48c: 2-[3-(2-Naphthylmethyl)-2,5-dioxo-1-piperazinyl]isocaproyl-Asp(OBn)-Phe-NH$_2$ To a 0° C. solution containing the compound of Example 48b (37 mg, 0.102 mmol) in methylene chloride (10 mL) were added TFA.Asp(β-OBn)-Phe-NH$_2$ (67 mg, 0.112 mmol), HOBt (33 mg, 0.21 mmol), EDCI (21 mg, 0.12 mmol) and N-methylmorpholine (25 mL, 0.22 mmol). The reaction mixture was stirred at 0° C. for 1 hour, warmed to ambient temperature and stirred for an additional 16 hours. Upon dilution with methylene chloride (100 mL), the reaction mixture was washed with 1M H$_3$PO$_4$ (3×), saturated sodium bicarbonate solution (3×) and brine. After drying over sodium sulfate, the solvent was evaporated in vacuo and the residue chromatographed on silica gel (eluting with methanol:chloroform) to yield 61 mg of the title compound as a white solid. MS(FAB+) m/e 720 (M+H)+. $^1$H NMR (DMSO-d$_6$, 300 MHz) δ0.81–0.92 (m, 6H), 1.24–1.65 (m, 4H), 2.40–2.64 (m, 2H), 2.79–3.61 (m, 4H), 4.21–4.44 (m, 3H), 4.50 (d, 1H), 4.61–4.71 (m, 1H), 4.96–5.14 (m, 3H), 7.15–7.47 (m, 16H), 7.65 (br s, 1H), 7.75–7.85 (m, 3H), 8.26–8.40 (m, 1H), 8.84 (m, 1H).

48d: 2-[3-(2-Naphthylmethyl)-2,5-dioxo-1-piperazinyl]isocaproyl-Asp-Phe-NH$_2$

To a solution containing 5% palladium-on-carbon (20 mg) and 1,4-cyclohexadiene (1 mL) in methanol (2 mL) was added the compound from Example 48c (30 mg, 0.042 mmol). The reaction mixture was stirred 17 hours after which time the catalyst was filtered off and the solvent evaporated in vacuo. The residue was chromatographed on silica gel (eluting with ethyl acetate:water:pyridine:acetic acid) to yield, after lyopholyzation, 15 mg of a white flocculent solid. MS(FAB+) m/e 630 (M+H)+. $^1$H NMR (DMSO-d$_6$, 300 MHz) δ0.80 (t, 6H), 1.24–1.61 (m, 3H), 2.77–2.90 (m, 2H), 3.05–3.64 (m, 4H), 4.05 (s, 2H), 4.19–4.25 (m, 1H), 4.30–4.38 (m, 1H), 4.41–4.48 (m, 1H), 4.85–4.91 (m, 1H), 7.18–7.35 (m, 8H), 7.45–7.51 (m, 2H), 7.70 (s, 2H), 7.82–7.89 (m, 3H), 8.26–8.38 (m, 2H), 12.00 (br s, 1H). Anal calc for $C_{34}H_{39}N_5O_7 \cdot H_2O$: C, 63.04; H, 6.38; N, 10.81. Found: C, 62.78; H, 6.16; N, 10.64.

EXAMPLE 49

Alternative preparation of 4-Carboxy-6-oxo-3,4,5,6-tetrahydro-1H,5H-azocin[4,5,6-c,d]indole (Ctp-OH)

49a: Ethyl α-(hydroxyimino)-β-(4-(carboethoxymethyl)indol-3-yl)-propanoate

To a solution of 4-(carboethoxymethyl)indole (830 mg, 4.12 mmol) and ethyl bromopyruvate 2-oxime (866 mg, 4.12 mmol) in methylene chloride (40 mL) was added anhydrous $Na_2CO_3$ (2.40 g, 22.66 mmol) at room temperature. After stirring at room temperature for 16 hours, the mixture was filtered and concentrated to dryness. The residue was flash chromatographed on silica gel (eluting (10% $MeOH/CHCl_3$):hexane=1:1→2:1) to give 0.98 g of the title compound; TLC $R_f$=0.61 (10% $MeOH/CHCl_3$). MS(CI) m/e 333 $(M+H)^+$. $^1H$ NMR ($CDCl_3$, 300 MHz) δ8.17 (br s, —NH), 8.03 (br s, —OH), 7.26 (d, J=7.4 Hz, 1H), 7.12 (t, J=7.4 Hz, 1H), 6.98 (d, J=7.4 Hz, 1H) 6.92 (br s, 1H), 4.30 (s, 2H), 4.28 (q, J=7.4 Hz, 2H), 4.18 (q, J=7.4 Hz, 2H), 4.13 (s, 2H), 1.30 (t, J=7.4 Hz, 3H), 1.25 (t, J=7.4 Hz, 3H).

49b: Ethyl α-(amino)-b-(4-(ethoxycarbonylmethyl)indol-3-yl)-propanoate

Aluminum strips (797 mg, 29.5 mmol) were amalgamated by immersing in a solution of $HgCl_2$ (216 mg, 0.80 mmol) in $H_2O$ (80 mL) for 15 seconds, then rinsed successively in EtOH and in ether, and added to a solution of the product of Example 58a (0.98 g, 2.95 mmol) in $THF/H_2O$ (10:1, 49.5 mL). After stirring for 3 hours, the mixture was dried with $Na_2SO_4$ and filtered through Celite ®. The filtrate was concentrated in vacuo to give 0.82 g of a yellow oil. TLC $R_f$=0.45 (10% $MeOH/CHCl_3$). MS(CI) m/e 319 $(M+H)^+$. $^1H$ NMR ($CDCl_3$, 300 MHz) δ8.12 (br m, indole —NH), 7.30 (dd, J=8.1, 0.9 Hz, 1H), 7.14 (t, J=8.1 Hz, 1H), 7.09 (br d, J=2.2 Hz, 2H), 4.03 (d, J=15.5 Hz, 1H), 3.50 (ddd, J=14.7, 4.8, 0.7 Hz, 1H) 3.25 (m, 1H), 3.00 (ddd, J=14.7, 8.5, 0.7 Hz, 1H), 1.25 (t, J=7.2 Hz, 3H), 1.26 (t, J=7.2 Hz, 3H).

49c: 4-Carboethoxy-6-oxo-3,4,5,6-tetrahydro-1H,5H-azocin[4,5,6-c,d]indole

A solution of the product of Example 49b (794 mg, 2.94 mmol) in o-xylene (50 mL) was heated at 145° C. for 3 days under nitrogen. The reaction mixture was filtered through a thin layer of silica (60 mm) and the filter cake was washed with 5% MeOH in $CHCl_3$. The filtrate was concentrated and the residue was taken up in $MeOH/CHCl_3$/toluene to precipitate the product. The first two crops provided 353 mg of the desired product as a yellow solid, m.p. 229°–230° C. TLC $R_f$=0.50 (10% $MeOH/CHCl_3$). MS(CI) m/e 273 $(M+H)^+$. $^1H$ NMR ($CDCl_3$, 300 MHz) δ7.24 (d, J=7.6 Hz, 1H), 7.12 (s, 1H), 7.01 (t, 1H), 6.87 (d, 1H), 4.47 (dd, J=9.9, 7.7 Hz, 1H), 4.28 (q, J=7.0 Hz, 2H), 4.20 (d, J=12.7 Hz, 1H), 3.76 (d, J=12.7 Hz, 1H), 3.55–3.65 (m, 2H), 1.34 (t, J=7.0 Hz, 3H). Anal. Calcd. for $C_{15}H_{16}N_2O_3 \cdot 1/5\ H_2O$: C, 65.30; H, 5.99; N, 10.15. Found: C, 65.35; H, 5.89; N, 10.09.

49d: 4-Carboxy-6-oxo-3,4,5,6-tetrahydro-1H,5H-azocin[4,5,6-c,d]indole (Ctp-OH)

To a solution of the product of Example 49c (40 mg, 0.147 mmol) in MeOH (1.5 mL) was added 2N NaOH (0.081 mL, 0.162 mmol) solution at room temperature. After stirring for 2 hours, the mixture was concentrated and the resulting residue was taken up in saturated $NaHCO_3$ solution and extracted with $CHCl_3$ (2×). The aqueous layer was acidified carefully with 4N HCl to pH 2 and then extracted with EtOAc (10×). The EtOAc extracts were dried over $Na_2SO_4$ and concentrated in vacuo to give 31 mg of the title compound as an off-white solid, m.p. 278°–280° C. (dec.). TLC $R_f$=0.14 ((pyridine/$H_2O$/HOAc=20:11:6-):EtOAc=1:3). MS(DCI/$NH_3$) m/e 245 $(M+H)^+$, 262 $(M+NH_4)^+$. Anal. Calcd. for $C_{13}H_{12}N_2O_3 \cdot 1/10$ EtOAc: C, 63.60; H, 5.10; N, 11.07. Found: C, 64.00; H, 5.41; N, 10.77.

EXAMPLE 50

Radioligand Binding in Guinea Pig Cerebral Cortical and Pancreatic Membrane Preparations 50a: Protocol CCK-8 (Asp-Tyr($SO_3H$)-Met-Gly-Trp-Met-Asp-Phe-$NH_2$), bestatin and phosphoramidon were purchased from Peptide International (Louisville, Ky.). EGTA, HEPES, BSA were purchased from Sigma Chemical Co. (St. Louis, Mo.). [$^{125}I$]-Bolton-Hunter CCK-8 (BH-CCK-8) (specific activity, 2200 Ci, mmol) was obtained from New England Nuclear (Boston, Mass.). Male guinea pigs, 250 to 325 g, were obtained from Scientific Small Animal Laboratory and Farm (Arlington Heights, Ill.). Collagenase, code CLSPA, was purchased from Worthington (Frehold, N.J.).

Cortical and pancreatic membranes were prepared as described (Lin and Miller; *J. Pharmacol. Exp. Ther.*, 1985, 232:775–780). In brief, pancreas and cortex were removed and rinsed with ice-cold saline. Visible fat and connective tissues were removed from the pancreas. Tissues were weighed and homogenized in approximately 25 mL of ice-cold 50 mM Tris-HCl buffer, pH 7.4 at 4° C. with a Brinkman Polytron for 30 seconds, setting 7. The homogenates were centrifuged for 10 minutes at 1075×g and the pellet was discarded. The supernatants were saved and centrifuged at 38,730×g for 20 minutes. The resultant pellets were rehomogenized in 25 mL of 50 mM Tris-HCl buffer with a Teflon-glass homogenizer, 5 up and down strokes. The homogenates were centrifuged again at 38,730×g for 20 minutes. The pellets were then resuspended in 20 mM HEPES, containing 1 mM EGTA, 118 mM NaCl, 4.7 mM KCl, 5 mM $MgCl_2$, 100 μM bestatin, 3 μM phosphoramidon, pH 7.4 at 22° C. with a Teflon-glass homogenizer, 15 up and down strokes. The resuspension volume used for the cortex was 15 mL per g of original wet weight and 60 mL per g for pancreas.

50b: Incubation Conditions

[$^{125}I$]Bolton-Hunter CCK-8 and test compounds were diluted with HEPES-EGTA-salt buffer (see above) containing 0.5% bovine serum albumin (BSA). To 1 mL Skatron polystyrene tubes were added 25 uL of test compounds, 25 uL of [$^{125}I$]BH-CCK8 and 200 uL of membrane suspension. The final BSA concentration was 0.1%. The cortical tissues (source of Type-B CCK receptors) were incubated at 30° C. for 150 minutes and pancreatic tissues (source of Type-A CCK receptors) were incubated at 37° C. for 150 minutes. Incubations were terminated by filtration using a Skatron Cell Harvester and SS32 microfiber filter mats. The specific binding of [$^{125}$I]BH-CCK-8, defined as the difference between binding in the absence and presence of 1 μM CCK-8, was 85–90% of total binding in cortex and 90–95% in pancreas. IC$_{50}$ values were determined from the Hill analysis. The results of these binding assays are shown in Table 1.

TABLE 1

| Compound of Example | IC$_{50}$ (nM)cortex (Type B) | IC$_{50}$ (nM)Pancreas (Type A) |
|---|---|---|
| 1 | 2.5 | 2,700 |
| 2 | 37.0 | 19,000 |
| 11 | 54.0 | 1,800 |
| 14 | 16.0 | >10,000 |
| 27 | 12.0 | 1,700 |
| 29 | 1.2 | 89,000 |
| 30 | 0.7 | 3,500 |
| 32 | 27.0 | 5,000 |
| 34 | 2.6 | 3,500 |
| 35 | 18.0 | 4,770 |
| 36 | 5.0 | 3,700 |
| 39 | 0.4 | 1,400 |
| 40 | 1.9 | 11,000 |
| 41 | 0.9 | 4,300 |
| 42 | 8.4 | 1,300 |
| 43 | 29.9 | 11,500 |
| 47 | 33.0 | >10,000 |

These results indicate that compounds of the invention possess high affinity and selectivity for the cortical (Type-B) CCK receptor.

EXAMPLE 51

[Ca$^{++}$]$_i$ Changes in NCl-H345 and H209 Cell Lines

Culture conditions were as described (D. G. Yoder, T. W. Moody, Peptides, 1987, 8:103, except that the medium was modified to RPMI 1640 with 2.5% fetal bovine serum (heat inactivated), 5 mg/l sodium selenite, 5 mg/l human transferrin, 5 mg/l insulin, penicillin (100 U/l) and streptomycin (100 mg/l). To measure intracellular Ca$^{++}$, cells were incubated with 1 μM indo-1/AM for 60 minutes at 37° C. The cells were then centrifuged at 750×g for 5 minutes and resuspended in 40 mL Buffer F (Dulbecco's phosphate buffered saline containing 0.1% glucose, pH 7.4). The cells were counted then twice washed by centrifugation. The final pellet was resuspended (approximately 1×10$^6$ cells/mL) in Buffer F. The cells were thermally equilibrated in a thermostated cuvette (37° C.) for 2 minutes prior to base-line fluorescence measurement. Fluorescence measurements were made with an SLM 8000C spectrofluorimeter equipped with magnetic microstirrer and polarizing filters. Measurements with indo-1-loaded cells were obtained at excitation wavelength of 350 nM and emission wavelength of 480 and 405 nM and the time interval for the measurements was 0.5 seconds. The test compounds were assayed at a single concentration (10$^{-5}$M) and compared to the response elicited by CCK-8 at 10$^{-6}$M to determine the % maximal response. Calibrations of [Ca$^{++}$]$_i$ were done as described (G. Grynkiewicz, M. Poenie, R. Y. Tsien, J. Biol. Chem., 1985, 260: 3440: [Ca$^{++}$]$_i$=K$_d$[(R−R$_{min}$)/(-R$_{max}$−R)](F$_{480min}$/F$_{480max}$) where R$_{min}$ and R$_{max}$ were the ratios (480/405) obtained in the presence of excess EGTA (10 mM) and digitonin (50 mM), respectively. F$_{480min}$ was the fluorescence value of the calcium-free dye at 480 nm, and F$_{480max}$ was the fluorescence value of the calcium-bound dye at 480 nm. K$_d$ is assumed to be 240 nM, and R is the ratio in the presence and the absence of CCK. Basal calcium levels were 147±3 nM (N=3) and the maximal levels of calcium stimulated with 100 nM CCK-8 were 357±30 nM (N=3). The results of these assays are shown in Table 2.

TABLE 2

| Compound of Example | Intrinsic Activity Relative to CCK-8 (%) |
|---|---|
| 5 | 96 |
| 26 | 104 |
| 30 | 103 |
| 34 | 100 |
| 39 | 109 |
| 40 | 100 |
| BOC-CCK-4 | 105 |
| CCK-8 (DS) | 53 |

The results indicate that compounds of this invention behave as agonists in stimulating calcium mobilization at CCK-B receptors on small cell lung cancer cell lines.

EXAMPLE 52

Response of VTA Neurons to Ethanol

Brain slices from Sprague-Dawley rats (100–200 g) containing the ventral tegmental area were prepared as previously described (Brodie and Dunwiddie, Brain Research, 1987, 425; 1061. Animals used in this study were treated in strict accordance with the NIH Guide for the Care and Use of Laboratory Animals. Coronal sections (400 μm thick) were cut and the tissue was place directly in the recording chamber. Small platinum weights were placed on the slice to increase the stability of recordings. The slice was covered with medium and a superfusion system then maintained the flow of medium at 2 mL/min; the temperature in the recording chamber was kept at 35° C. The composition of the artificial cerebrospinal fluid (aCSF) in these experiments was (in mM): NaCl 125, KCl 2.5, NaH$_2$PO$_4$ 1.25, MgSO$_4$ 2, NaHCO$_3$ 25, glucose 11, CaCl$_2$ 2; the aCSF was saturated with 95% O$_2$/5% CO$_2$. The flow rate was continuously monitored with a flowmeter and adjustable valves were used to keep the rate constant. The small volume chamber (about 300 microliters) used in this study permitted the rapid infusion and washout of drug solutions.

Ethanol and the CCK agonist compound were added to the aCSF in the fluid delivery tubing by means of a calibrated infusion pump from stock solutions 100 to 1000 times the desired final concentrations. Final concentrations were calculated from a aCSF flow rate, pump infusion rate and concentration of drug stock solution. Infusion of drug solutions never exceeded 2% of the flow rate of the aCSF and usually was kept below 1%. All drugs were dissolved in degassed distilled water; for concentrations above 30 mM, 95% EtOH was used in the pump. The pharmacologically active range for blood ethanol in the rat extends from 10–20 mM for mild motor deficits to 200 mM (lethal), and therefore these studies were generally limited to application of ethanol in the range of 20 to 200 mM. In practice, the concentration range of ethanol tested with the compound of Example 30 was 80 to 160 mM. Within this range, the percentage increase in ethanol potency produced by the CCK agonist was not significantly dependent upon ethanol concentration.

Extracellular recording electrodes were made from 1.5 mm diameter glass tubing; tip resistance of the microelectrodes ranged from 6–10 MOhm. At least one hour after preparation of the slice was allowed for equilibration. After this period, the electrode was lowered into the VTA under visual guidance. The VTA is clearly visible in fresh tissue as a grey area medial to the substantia nigra.

Frequency of firing was determined using a window discriminator and ratemeter, the output of which was fed to a chart recorder. In addition, an IBM-PC-based data acquisition system was used to calculate, display and store the frequency of firing over 5 seconds and 1 minute intervals. The protocol for administration of ethanol and the CCK agonist was as follows: Ethanol was added to the superfusate via a calibrated infusion pump and the magnitude of ethanol-induced excitation was measured. The ethanol infusion was halted, and the cell firing rate was allowed to return to pre-ethanol levels. The CCK agonist compound of Example 30 was then added to the superfusion medium via a calibrated infusion pump. At least 10 minutes after the initiation of the CCK agonist infusion, ethanol was infused at the same rate (in order to achieve the same concentration) as prior to the CCK agonist infusion. The increases in firing rate (as percentage of pre-ethanol firing rate) induced by ethanol before and after the CCK agonist infusion were compared and are summarized in Table 3.

TABLE 3

| Compound of Example 30 Concentration | % Increase in EtOH Potency | Number of Cells Tested |
|---|---|---|
| 50 nM | 6.8 | 5 |
| 100–250 nM | 12.6 | 5 |
| 400–500 nM | 24 | 3 |

These data in Table 3 demonstrate that the compound of Example 30 increases the excitatory effect of ethanol on VTA neurons.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

A—B—Y—Z        (I)

or a pharmaceutically-acceptable salt thereof, wherein
A is either

(a)

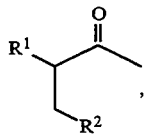

wherein
$R^1$ is selected from the group consisting of
  (i) hydrogen,
  (ii) halogen,
  (iii) hydroxy,
  (iv) $C_1$–$C_6$-alkoxy,
  (v) thio-$C_1$–$C_6$-alkoxy,
  (vi) amino,
  (vii) (N-protected)amino,
  (viii) $C_1$–$C_6$-alkylamino,
  (ix) (N-protected)-$C_1$–$C_6$-alkylamino, and
  (x) $R^5$—$R^4$—C(O)—N($R^3$)—, wherein
    $R^3$ is hydrogen or $C_1$–$C_6$-alkyl;

$R^4$ is $C_1$–$C_6$-alkylene or $C_2$–$C_6$-alkenylene; and
$R^5$ is phenyl or substituted phenyl;
$R^2$ is naphthyl, mono-substituted naphthyl, phenyl, mono-substituted phenyl, benzohet, or mono-substituted benzohet; or

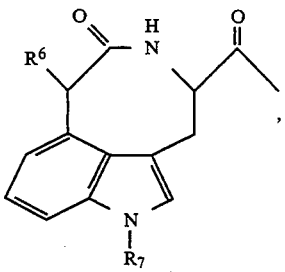

(b)

wherein
$R^6$ is selected from the group consisting of
  (i) hydrogen,
  (ii) hydroxy,
  (iii) halogen,
  (iv) $C_1$–$C_6$-alkyl,
  (v) amino,
  (vi) $C_1$–$C_6$-alkylamino, and
  (vii) di-$C_1$–$C_6$-alkylamino; and
$R^7$ is hydrogen, $C_1$–$C_6$-alkyl or $C_1$–$C_6$-alkanoyl;
B is either

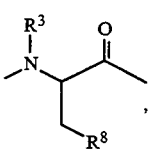

(a)

wherein
$R^3$ is as defined above; and
$R^8$ is $C_1$–$C_6$-alkyl or mono-substituted $C_1$–$C_4$-alkylene, wherein the substituent is $C_1$–$C_6$-alkoxy or thio-$C_1$–$C_6$-alkoxy; or

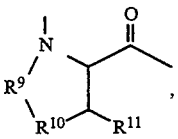

(b)

wherein
$R^9$ is $C_2$–$C_4$-alkylene;
$R^{10}$ is absent or is oxygen or sulfur; and
$R^{11}$ is hydrogen, $C_1$–$C_6$-alkyl, $C_1$–$C_6$-alkoxy, thio-$C_1$–$C_6$-alkoxy, or mono-substituted $C_1$–$C_4$-alkylene, wherein the substituent is $C_1$–$C_6$-alkoxy or thio-$C_1$–$C_6$-alkoxy;
Y is

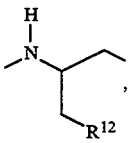

wherein $R^{12}$ is carboxy or tetrazolyl; and
Z is

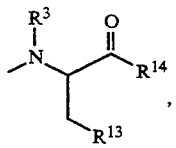
(1)

wherein
R³ is as defined above;
R¹³ is selected from the group consisting of
(i) $C_1$–$C_6$-alkyl,
(ii) cyclo-$C_3$–$C_8$-alkyl,
(iii) Het,
(iv) mono-substituted Het,
(v) naphthyl,
(vi) mono-substituted naphthyl,
(vii) phenyl,
(viii) mono-substituted phenyl,
(ix) benzohet, and
(x) mono-substituted benzohet; and
R¹⁴ is —NHR¹⁵, wherein R¹⁵ is hydrogen, hydroxy, methyl or amino;

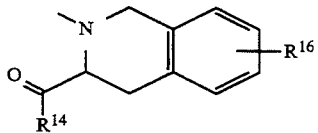
(2)

wherein
R¹⁴ is as defined above;
R¹⁶ is selected from the group consisting of
(i) hydrogen,
(ii) $C_1$–$C_6$-alkyl,
(iii) halogen,
(iv) halo-$C_1$–$C_6$-alkyl,
(v) $C_1$–$C_6$-alkoxy,
(vi) thio-$C_1$–$C_6$-alkoxy,
(vii) hydroxy,
(viii) $C_1$–$C_6$-alkoxycarbonyl,
(ix) carboxy,
(x) amino,
(xi) $C_1$–$C_6$-alkylamino,
(xii) di-$C_1$–$C_6$-alkylamino,
(xiii) nitro, and
(xiv) —OSO₃H; or

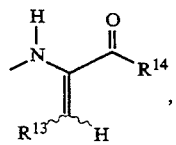
(3)

wherein R¹³ and R¹⁴ are as defined above;

with the proviso that when A is selected from either option (a) for A above where R¹ is amino, (N-protected)amino or R⁵—R⁴—C(O)—N(R³)—, then B must be selected from option (b) for B above or Z must be selected from options (2) or (3) for Z above.

2. A compound of claim 1, wherein B is selected from option (b) for B, or A is selected from option (b) for A.

3. A compound of claim 1, wherein A is selected from option (a), with R¹ being amino or (N-protected)amino and option (b) with R⁶ being hydrogen, and B is selected from option (b) with R¹⁰ being absent, and R¹¹ being $C_1$–$C_6$-alkyl.

4. A compound according to claim 1 which is selected from the group consisting of:
Ctp-Leu-Asp-Phe-NH₂;
BOC-Trp-Leu-Asp-Tiq-NH₂;
Ctp-Leu-Asp-(NMe)Phe-NH₂;
Ctp-Leu-Asp-(dehydro)Phe-NH₂;
BOC-Trp-Tpp-Asp-Phe-NH₂;
Ctp-Tpp-Asp-Phe-NH₂;
Ctp-Tpp-Asp-(NMe)Phe-NH₂;
Ctp-Cpp-Asp-Phe-NH₂;
BOC-Trp-Tpp-Asp-Trp-NH₂;
Ctp-Tpp-Asp-α-Nal-NH₂;
Ctp-Tpp-Asp-β-Nal-NH₂;
Ctp-Tpp-Asp-Cha-NH₂;
Ctp-(1,4-thiazane-3-carbonyl)-Asp-Phe-NH₂; and
Ctp-Pip-Asp-Phe-NH₂, or
a pharmaceutically-acceptable salt thereof.

5. Ctp-Tpp-Asp-Phe-NH₂.

6. A pharmaceutical composition for treating CCK type-B receptor-related disorders comprising a pharmaceutically-acceptable carrier and a therapeutically-effective amount of a compound of claim 1.

7. A method for mimicking the effects of CCK on CCK type-B receptor comprising administering to a human or other mammal in need of such treatment a therapeutically-effective amount of a compound of claim 1.

8. A method for treating schizophrenia, convulsions, neurodegeneration and Parkinson's disease comprising administering to a human or other mammal in need of such treatment a therapeutically-effective amount of a compound of claim 1.

9. A method for treating gastrointestinal and endocrine disorders comprising administering to a human or other mammal in need of such treatment a therapeutically-effective amount of a compound of claim 1.

10. A method for treating hemorrhagic shock comprising administering to a human or other mammal in need of such treatment a therapeutically-effective amount of a compound of claim 1.

11. A method for treating alcohol addiction comprising administering to a human or other mammal in need of such treatment a therapeutically-effective amount of a compound of claim 1.

* * * * *